US011014897B1

(12) United States Patent
Huang et al.

(10) Patent No.: US 11,014,897 B1
(45) Date of Patent: May 25, 2021

(54) SOLID FORMS COMPRISING A THIAZOLIDINONE COMPOUND, COMPOSITIONS AND METHODS OF USE THEREOF

(71) Applicant: Celgene Corporation, Summit, NJ (US)

(72) Inventors: Lianfeng Huang, Basking Ridge, NJ (US); Daozhong Zou, Raritan, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 16/653,643

(22) Filed: Oct. 15, 2019

Related U.S. Application Data

(60) Provisional application No. 62/746,422, filed on Oct. 16, 2018.

(51) Int. Cl.
| | | |
|---|---|---|
| *A61K 31/426* | (2006.01) | |
| *C07D 277/54* | (2006.01) | |
| *A61P 37/06* | (2006.01) | |
| *A61K 9/48* | (2006.01) | |
| *A61K 9/20* | (2006.01) | |

(52) U.S. Cl.
CPC .............. *C07D 277/54* (2013.01); *A61K 9/20* (2013.01); *A61K 9/48* (2013.01); *A61P 37/06* (2018.01)

(58) Field of Classification Search
None
See application file for complete search history.

(56) References Cited

U.S. PATENT DOCUMENTS

| | | | |
|---|---|---|---|
| 7,435,828 | B2 | 10/2008 | Binkert et al. |
| 8,263,780 | B2 | 9/2012 | Abele et al. |
| 8,273,779 | B2 | 9/2012 | Binkert et al. |
| RE43,728 | E | 10/2012 | Binkert et al. |
| 8,399,514 | B2 | 3/2013 | Lukashev et al. |
| 8,524,752 | B2 | 9/2013 | Binkert et al. |
| 8,785,484 | B2 | 7/2014 | Brossard et al. |
| 8,912,340 | B2 | 12/2014 | Abele et al. |
| 9,000,018 | B2 | 4/2015 | Binkert et al. |
| 9,062,014 | B2 | 6/2015 | Bonham et al. |
| 9,340,518 | B2 | 5/2016 | Herse |
| 2007/0134803 | A1 * | 6/2007 | Blatter .................. B01J 19/0046 436/96 |
| 2014/0303217 | A1 | 10/2014 | Brossard et al. |
| 2014/0316140 | A1 | 10/2014 | Brossard et al. |

FOREIGN PATENT DOCUMENTS

| | | |
|---|---|---|
| EP | 2 316 430 B1 | 6/2012 |
| WO | WO 2005/054215 A1 | 6/2005 |
| WO | WO 2005/123677 A1 | 12/2005 |
| WO | WO 2006/010379 A1 | 2/2006 |
| WO | WO 2006/010544 A2 | 2/2006 |
| WO | WO 2006/100633 A1 | 9/2006 |
| WO | WO 2006/100635 A2 | 9/2006 |
| WO | WO 2007/080542 A1 | 7/2007 |
| WO | WO 2008/029306 A2 | 3/2008 |
| WO | WO 2008/062376 A2 | 5/2008 |
| WO | WO 2008/097596 A2 | 8/2008 |
| WO | WO 2008/114157 A1 | 9/2008 |
| WO | WO 2009/024905 A1 | 2/2009 |
| WO | WO 2009/074950 A2 | 6/2009 |
| WO | WO 2009/115954 A1 | 9/2009 |
| WO | WO 2010/046835 A1 | 4/2010 |
| WO | WO 2011/007324 A1 | 1/2011 |
| WO | WO 2013/184888 A1 | 12/2013 |
| WO | WO 2014/027330 A1 | 2/2014 |
| WO | WO 2016/091996 A1 | 6/2016 |
| WO | WO 2016/092042 A1 | 6/2016 |
| WO | WO 2017/107972 A1 | 6/2017 |
| WO | WO 2018/167030 A1 | 9/2018 |
| WO | WO 2019/060147 A1 | 3/2019 |

OTHER PUBLICATIONS

Background Information for the October ACPS Meeting, FDA, 2002.*
B. Rodriquez-Spong et al. Advanced Drug Delivery Reviews, 2004, 56, pp. 241-274.*
Hilfiker, R. Polymorphism in the Pharmaceutical Industry, Wiley, 2006, 213-216.*
Boehler et al., "Absolute Bioavailability of Ponesimod, a Selective S1P 1 Receptor Modulator, in Healthy Male Subjects," *Eur J Drug Metab Pharmacokinet.*, 42(1):129-134 (2017).
Bolli et al., "2-imino-thiazolidin-4-one Derivatives as Potent, Orally Active S1P1 Receptor Agonists," J Med Chem.;53(10):4198-4211 (2010).
Brossard et al., "Multiple-dose Tolerability, Pharmacokinetics, and Pharmacodynamics of Ponesimod, an S1P1 Receptor Modulator: Favorable Impact of Dose Up-Titration," *J. Clin. Pharmacol.*, 54(2):179-188 (2014).
D'Ambrosio et al., *Immunopharmacol Immunotoxicol.* 37(1):103-109. (2015).
D'Ambrosio et al., "Ponesimod, a Selective S1P1 Receptor Modulator: A Potential Treatment for Multiple Sclerosis and Other Immune-Mediated Diseases," *Ther. Adv. Chronic. Dis.*,7(1):18-33 (2016).
Guerard et al., "Effect of Hepatic or Renal Impairment on the Pharmacokinetics, Safety, and Tolerability of Ponesimod, a Selective S1P1 Receptor Modulator," *Basic Clin. Pharmacol. Toxicol.*, 118(5):356-368 (2016).
Hoch et al., "Effect of Ponesimod, a Selective S1P1 Receptor Modulator, on the QT Interval in Healthy Individuals," *Basic Clin. Pharmacol. Toxicol.*, 116(5): 429-437 (2015).
Hoch et al., "Clinical Pharmacology of Ponesimod, a Selective S1P1 Receptor Modulator, After Uptitration to Supratherapeutic Doses in Healthy Subjects," *Eur. J. Pharm. Sci.*, 63:147-153 (2014).
Juif et al., "Biocomparisonof three formulations of the SIP receptor modulator ponesimod in healthy subjects," *Drugs R D.* 15(2):203-210 (2015).
Juif et al., "Clinical Pharmacology, Efficacy, and Safety Aspects of sphingosine-1-phosphate Receptor Modulators," *Expert Opin Drug Metab Toxicol.* 12(8):879-895 (2016).

(Continued)

*Primary Examiner* — Samantha L Shterengarts
(74) *Attorney, Agent, or Firm* — Jones Day

(57) ABSTRACT

Provided herein are formulations, processes, solid forms and methods of use relating to (Z)-5-((Z)-3-chloro-4-((R)-2,3-dihydroxypropoxy)benzylidene)-2-(propylimino)-3-(o-tolyl)thiazolidin-4-one.

20 Claims, 37 Drawing Sheets

(56) References Cited

OTHER PUBLICATIONS

Figure 1:
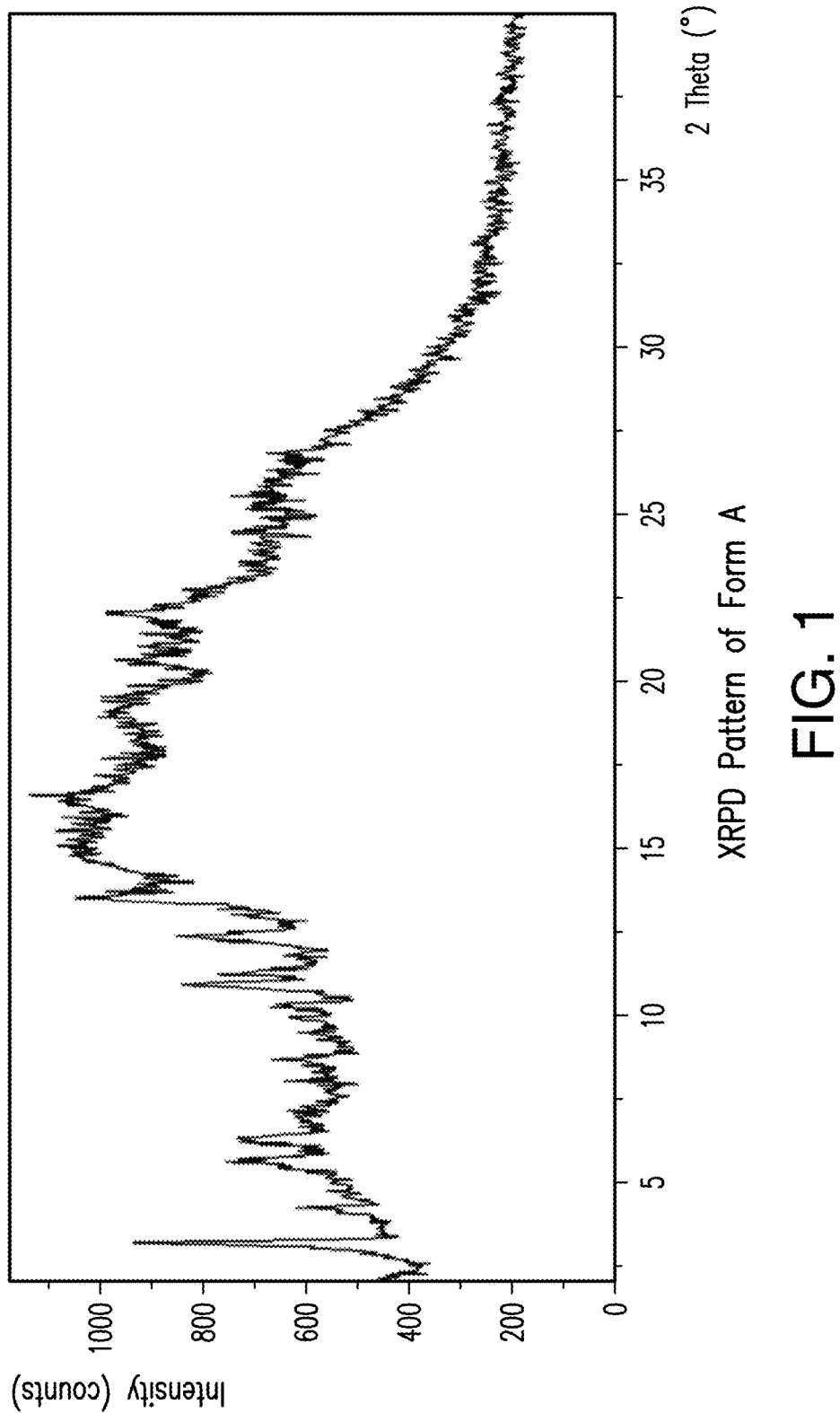

Juif et al., "Mitigation of Initial Cardiodynamic Effects of the S1P 1 Receptor Modulator Ponesimod Using a Novel Up-Titration Regimen," *J. Clin. Pharmacol.*, 57(3):401-410 (2017).
Jurcevic et al., "Effects of Multiple-Dose Ponesimod, a Selective S1P 1 Receptor Modulator, on Lymphocyte Subsets in Healthy Humans," *Drug Des. Devel Ther.*, 11:123-131 (2016).
Krause et al., "Population Pharmacokinetics and Pharmacodynamics of Ponesimod, a Selective S1P1 Receptor Modulator," *J Pharmacokinet Pharmacodyn.*, 41(3):261-278 (2014).
Lott et al., "Impact of Demographics, Organ Impairment, Disease, Formulation, and Food on the Pharmacokinetics of the Selective S1P 1 Receptor Modulator Ponesimod Based on 13 Clinical Studies," *Clin. Pharmacokinet.*, 56(4):395-408 (2017).
Lott et al., "Population Pharmacokinetics of Ponesimod and Its Primary Metabolites in Healthy and Organ-Impaired Subjects," *Eur J Pharm Sci.*,89:83-93 (2016).
Lott et al., Pharm Res.;34(3):599-609 (2017).
NCT01006265: Clinical Study to Evaluate the Efficacy, Safety, and Tolerability of ACT-128800 in Patients With Relapsing-remitting Multiple Sclerosis. https://clinicaltrials.gov/ct2/show/NCT01006265. First posted Nov. 1, 2009; last update posted Apr. 4, 2017; downloaded May 28, 2020.
NCT01093326: Clinical Study to Investigate the Long-term Safety, Tolerability, and Efficacy of Ponesimod in Patients With Relapsing-remitting Multiple Sclerosis. https://clinicaltrials.gov/ct2/show/NCT01093326?term=NCT01093326&draw=2&rank=1. Fist posted Mar. 25, 2010; last updated posted May 21, 2020; downloaded May 28, 2020.
NCT01755871: Long-term Effect of Fingolimod on Circulating Immunocompetent Mononuclear Cells in Patients With Multiple Sclerosis (terminated). https://clinicaltrials.gov/ct2/show/NCT01755871?term=NCT01755871&draw=2&rank=1. First posted Dec. 24, 2012; Last Update Posted Jun. 9, 2016; downloaded May 28, 2020.
NCT02029482: Study to Investigate the Safety, Tolerability, Pharmacokinetics, and Pharmacodynamics of ACT-128800 in Healthy Subjects. https://clinicaltrials.gov/ct2/show/NCT02029482?term=NCT02029482&draw=2&rank=1. First Posted Jan. 8, 2014; Last Update Posted Jan. 8, 2014; downloaded May 28, 2020.
NCT02068235: Study to Investigate the Absolute Bioavailability of a Single Oral Dose of Ponesimod in Healthy Male Subjects. https://clinicaltrials.gov/ct2/show/NCT02068235?term=NCT02068235&draw=2&rank=1. First Posted Feb. 21, 2014; Last Update Posted May 21, 2015; downloaded May 28, 2020.
NCT02126956: Mass Balance, Pharmacokinetics, and Metabolism of 14C-labeled ACT-128800 Administered to Healthy Male Subjects. https://clinicaltrials.gov/ct2/show/NCT02126956?term=NCT02126956&draw=2&rank=1. First Posted Apr. 30, 2014; Late Update Posted Apr. 30, 2014; downloaded May 28, 2020.
NCT02136888: Study of the Electrocardiographic Effects of Ponesimod in Healthy Male and Female Subjects. https://clinicaltrials.gov/ct2/show/NCT02136888?term=NCT02136888&draw=2&rank=1. First Posted May 13, 2014; Last Update Posted May 13, 2014; downloaded May 28, 2020.
NCT02223832: Study to Evaluate the Pharmacokinetics, Tolerability, and Safety of ACT-128800 in Japanese and Caucasian Healthy Male and Female Subjects. https://clinicaltrials.gov/ct2/show/NCT02223832?term=NCT02223832&draw=2&rank=1. First Posted Aug. 22, 2014; Last Update Posted Aug. 22, 2014; downloaded May 22, 2020.
NCT02425644: Oral Ponesimod Versus Teriflunomide in Relapsing MUltiple Sclerosis (Optimum). https://clinicaltrials.gov/ct2/show/NCT02425644?term=NCT02425644&draw=2&rank=1. First Posted Apr. 24, 2015; Last Update Posted May 27, 2020; downloaded May 28, 2020.
NCT02461134: Clinical Study to Investigate the Biological Activity, Safety, Tolerability, and Pharmacokinetics of Ponesimod in Subjects With Symptomatic Chronic GVHD (terminated). https://clinicaltrials.gov/ct2/show/NCT02461134?term=NCT02461134&draw=2&rank=1. First Posted Jun. 3, 2015; Last Update Posted May 9, 2018; downloaded May 28, 2020.
NCT02907177: Clinical Study to Compare the Efficacy and Safety of Ponesimod to Placebo in Subjects With Active Relapsing Multiple Sclerosis Who Are Treated With Dimethyl Fumarate (Tecfidera®). https://clinicaltrials.gov/ct2/show/NCT02907177?term=NCT02907177&draw=2&rank=1. First Posted Sep. 20, 2016; Last Update Posted Apr. 6, 2020; downloaded May 28, 2020.
Olsson et al., "Oral Ponesimod in Relapsing-Remitting Multiple Sclerosis: A Randomised Phase II Trial," *Neuro.l Neurosurg. Psychiatry.*, 85(11):1198-1208 (2014).
Piali et al., "The Selective Sphingosine 1-phosphate Receptor 1 Agonist Ponesimod Protects Against Lymphocyte-Mediated Tissue Inflammation," *J. Pharmacol. Exp. Ther.*, 337(2):547-556 (2011).
Rey et al., "Desensitization by Progressive Up-Titration Prevents First-Dose Effects on the Heart: Guinea Pig Study With Ponesimod, a Selective S1P1 Receptor Modulator," *PLoS One.*, 8(9):e74285 (2013).
Reyes et al., "Effects of Ethnicity and Sex on the Pharmacokinetics and Pharmacodynamics of the Selective sphingosine-1-phosphate Receptor 1 Modulator Ponesimod: A Clinical Study in Japanese and Caucasian Subjects," *Pharmacology*, 94(5-6): 223-229 (2014).
Reyes et al., "Mass Balance, Pharmacokinetics and Metabolism of the Selective S1P1 Receptor Modulator Ponesimod in Humans," *Xenobiotica.*, 45(2):139-149 (2015).
Scherz et al. "Three Different Up-Titration Regimens of Ponesimod, an S1P1 Receptor Modulator, in Healthy Subjects," *J. Clin. Pharmacol.*, 55(6):688-697 (2015).

* cited by examiner

PLM Image of Form A

DSC and TGA of Form B

PLM Image of Form B

PLM Image of Form C

DSC and TGA of Form D

PLM Image of Form D

DSC and TGA of Form E

PLM Image of Form E

FT-Raman Spectrum of Form F

DSC and TGA of Form F

PLM Image of Form F

DSC and TGA of Form G

PLM Image of Form G

PLM Image of Form H

SOLID FORMS COMPRISING A THIAZOLIDINONE COMPOUND, COMPOSITIONS AND METHODS OF USE THEREOF

This application claims priority to U.S. Provisional Application No. 62/746,422, filed Oct. 16, 2018, the entirety of which is incorporated herein by reference.

1. FIELD

Provided herein are solid forms comprising (Z)-5-((Z)-3-chloro-4-((R)-2,3-dihydroxypropoxy)benzylidene)-2-(propylimino)-3-(o-tolyl)thiazolidin-4-one. Pharmaceutical compositions comprising such solid forms and methods of use of such solid forms for treating, preventing, and managing various disorders are also provided herein.

2. BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune or chronic inflammatory diseases include Graves' disease, Type 1 diabetes, multiple sclerosis, inflammatory bowel disease, systemic lupus, polymyositis, dermatomyositis, lupus nephritis, rheumatoid arthritis, and psoriasis.

Multiple Sclerosis ("MS") is an autoimmune disease of the central nervous system, characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

There is a need in the art for novel drug products for the treatment of MS and other autoimmune diseases of the central nervous systems. Alternative solid forms of pharmaceutical compounds have emerged as a possible approach to modulate or enhance the physical and chemical properties of drug products. The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solid forms include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

3. SUMMARY

Provided herein are solid forms comprising Compound 1 (e.g., crystalline forms, amorphous forms, polymorphs or mixtures thereof):

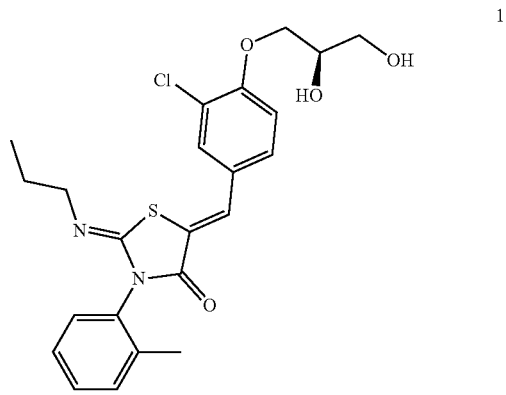 [SMILES: CCC/N=C1\S/C(=C\c2ccc(OC[C@H](O)CO)c(Cl)c2)C(=O)N1c1ccccc1C]

having the chemical name (Z)-5-((Z)-3-chloro-4-((R)-2,3-dihydroxypropoxy)benzylidene)-2-(propylimino)-3-(o-tolyl)thiazolidin-4-one (also known as ponesimod). The solid forms also include solid forms comprising a tautomer of Compound 1. Also provided herein are methods of preparing, isolating, and characterizing the solid forms.

In one embodiment, the solid form is Form A, Form B, Form C, Form D, Form E, Form F, Form G, Form H, or Form I, as described herein.

In another embodiment, provided herein are pharmaceutical compositions comprising one or more of the solid forms described herein. In certain embodiments, the solid form is no less than 95% pure. In certain embodiments, the pharmaceutical composition further comprises a second solid form described herein. In certain embodiments, the pharmaceutical composition further comprises an amorphous form of Compound 1. In certain embodiments, the pharmaceutical composition further comprises a pharmaceutically acceptable excipient or carrier. In certain embodiments, the pharmaceutical composition is a single unit dosage form. In certain embodiments, the pharmaceutical composition is a tablet. In certain embodiments, the pharmaceutical composition is a capsule.

In another embodiment, provided herein is a method of treating multiple sclerosis, wherein the method comprises administering to a patient in need thereof a therapeutically effective amount of a solid form described herein. In another embodiment, provided herein is a method of treating multiple sclerosis, wherein the method comprises administering to a patient in need thereof a therapeutically effective amount of a pharmaceutical composition described herein. In one embodiment, the multiple sclerosis is relapsing multiple sclerosis. In one embodiment, the multiple sclerosis is relapsing-remitting multiple sclerosis.

In another embodiment, provided herein is a method of treating psoriasis, wherein the method comprises administering to a patient in need thereof a therapeutically effective amount of a solid form described herein. In another embodiment, provided herein is a method of treating psoriasis, wherein the method comprises administering to a patient in need thereof a therapeutically effective amount of a pharmaceutical formulation described herein. In one embodiment, the psoriasis is moderate to severe chronic plaque psoriasis.

In another embodiment, provided herein is a method of treating polymyositis, wherein the method comprises administering to a patient in need thereof a therapeutically effective amount of a solid form described herein. In another embodiment, provided herein is a method of treating polymyositis, wherein the method comprises administering to a patient in need thereof a therapeutically effective amount of a pharmaceutical formulation described herein.

4. BRIEF DESCRIPTION OF THE DRAWINGS

FIG. 1 provides a representative X-ray powder diffraction (XRPD) pattern of Form A of Compound 1.

Figure 2:
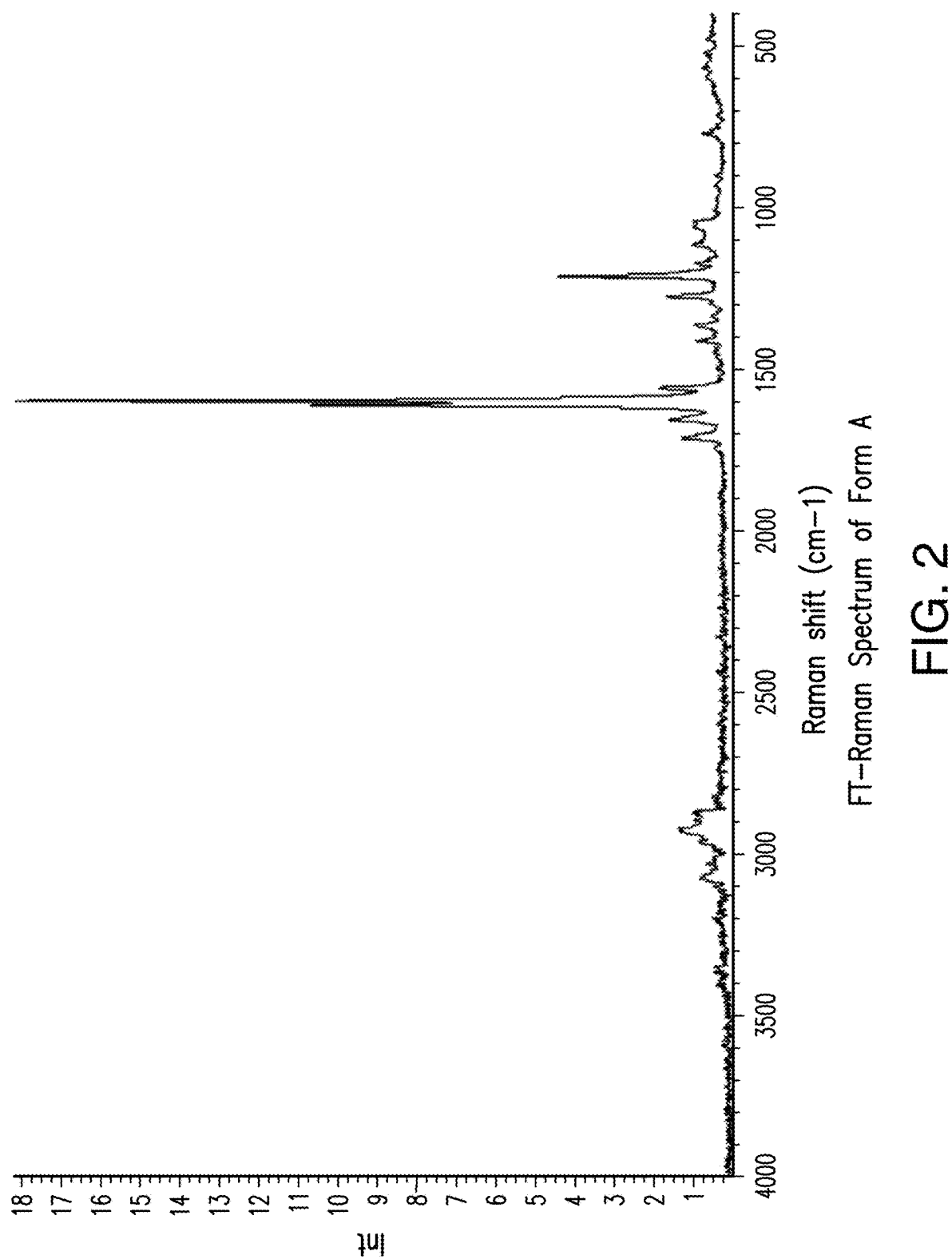

FIG. 2 provides a representative FT-Raman spectrum of Form A of Compound 1.

Figure 3:
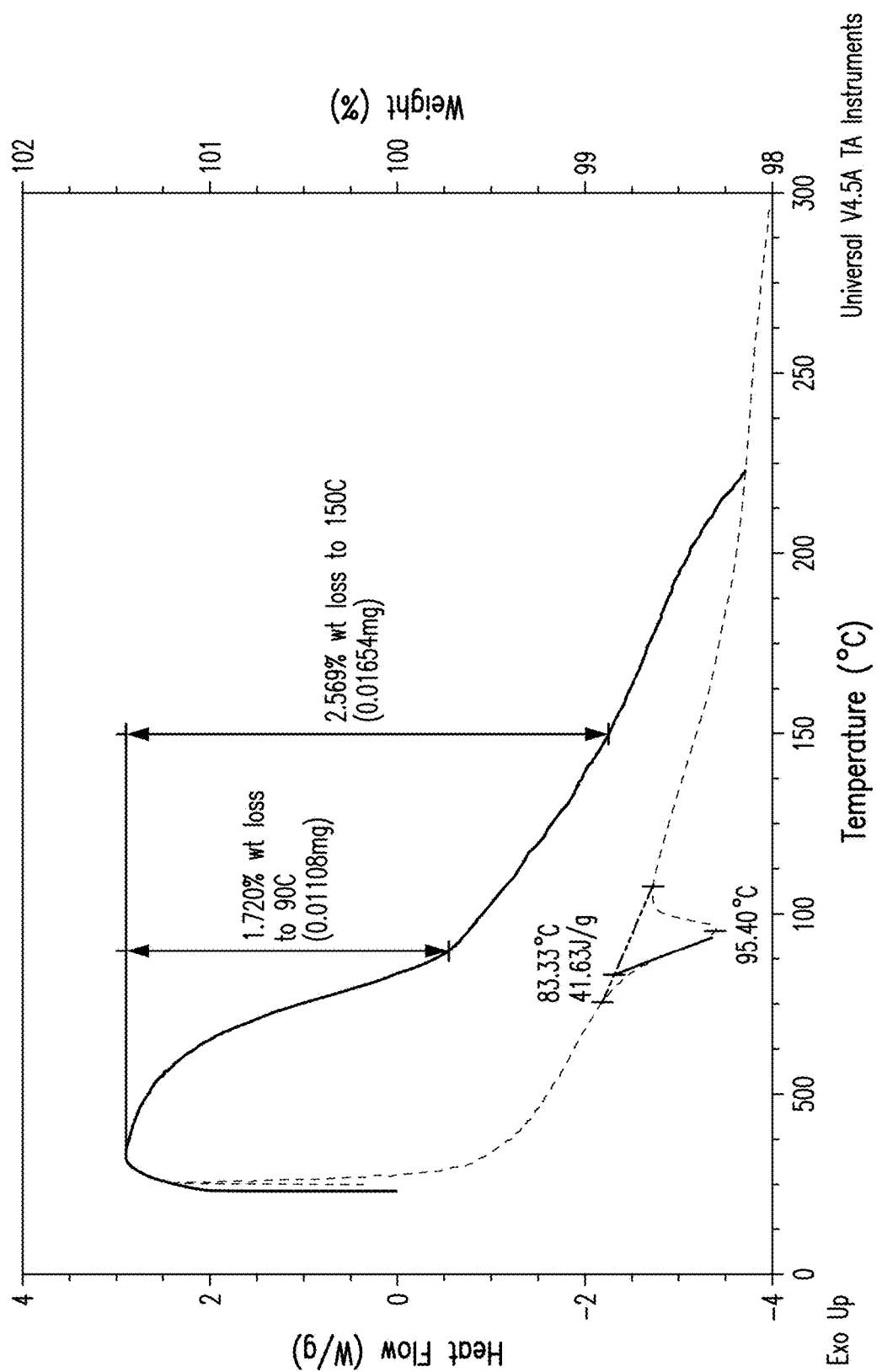

FIG. 3 provides representative differential scanning calorimetry (DSC) and thermal gravimetric analysis (TGA) thermograms of Form A of Compound 1.

Figure 4:
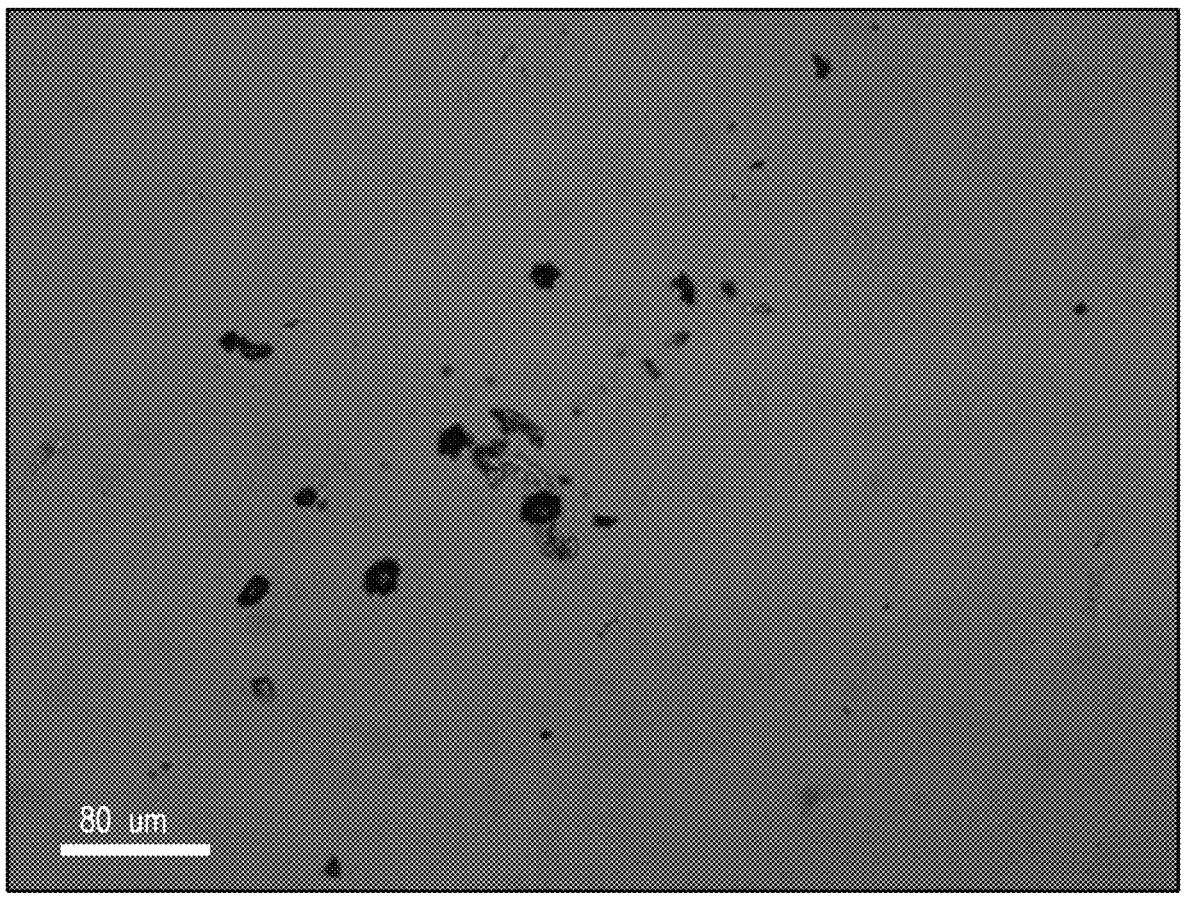

FIG. 4 provides a representative polarized light microscopy (PLM) image of Form A of Compound 1.

Figure 5A:
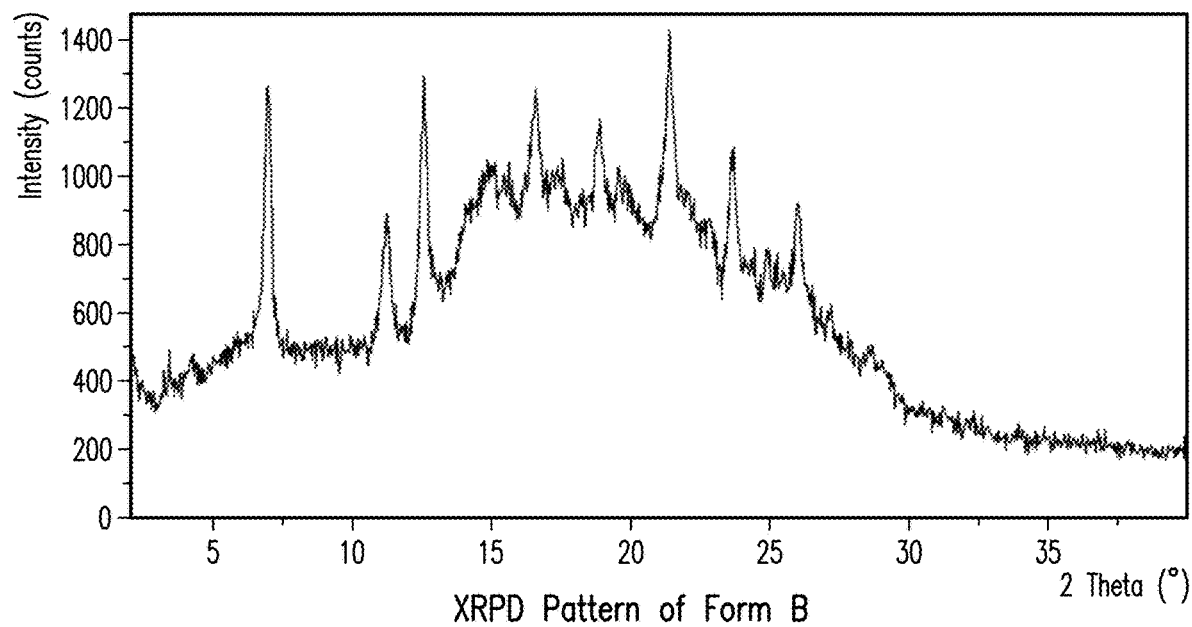
Figure 5B:
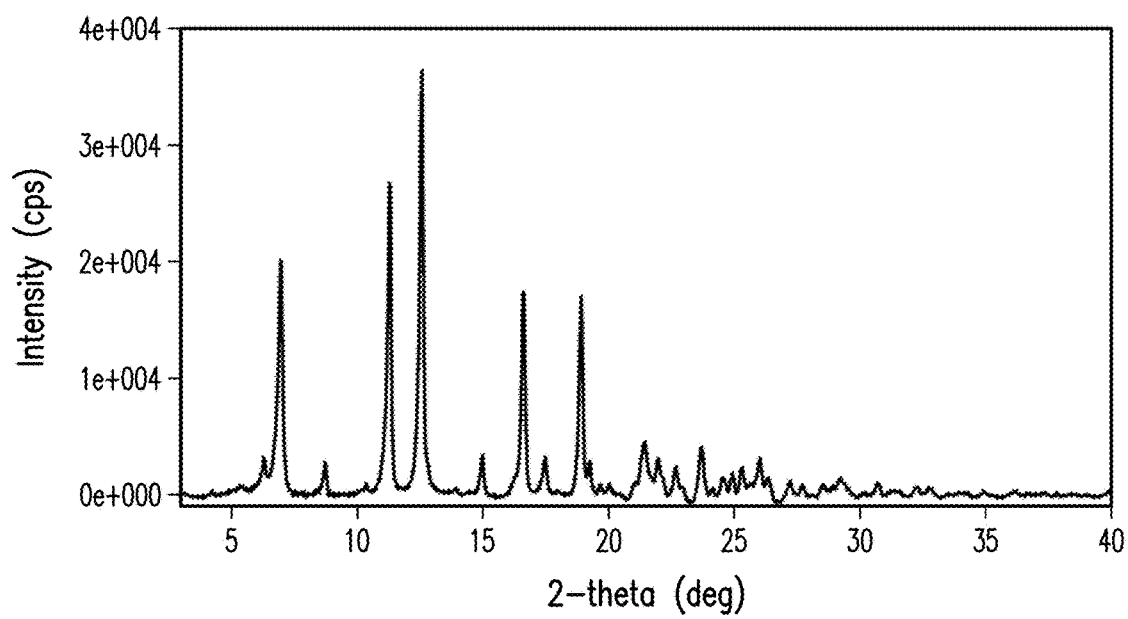

FIG. 5A provides a representative XRPD pattern of Form B of Compound 1; FIG. 5B provides another representative XRPD pattern of Form B of Compound 1.

Figure 6:
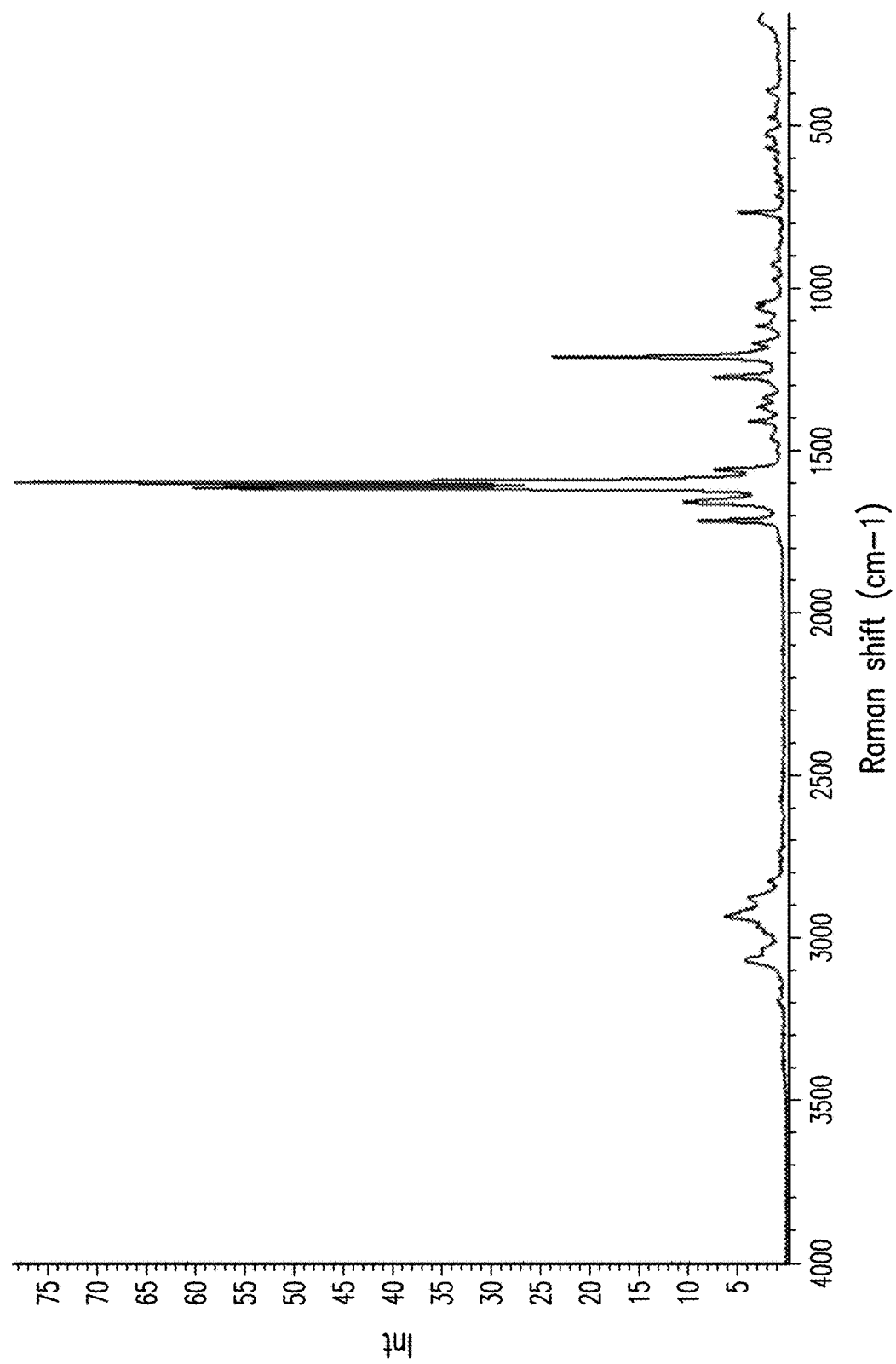

FIG. 6 provides a representative FT-Raman spectrum of Form B of Compound 1.

Figure 7A:
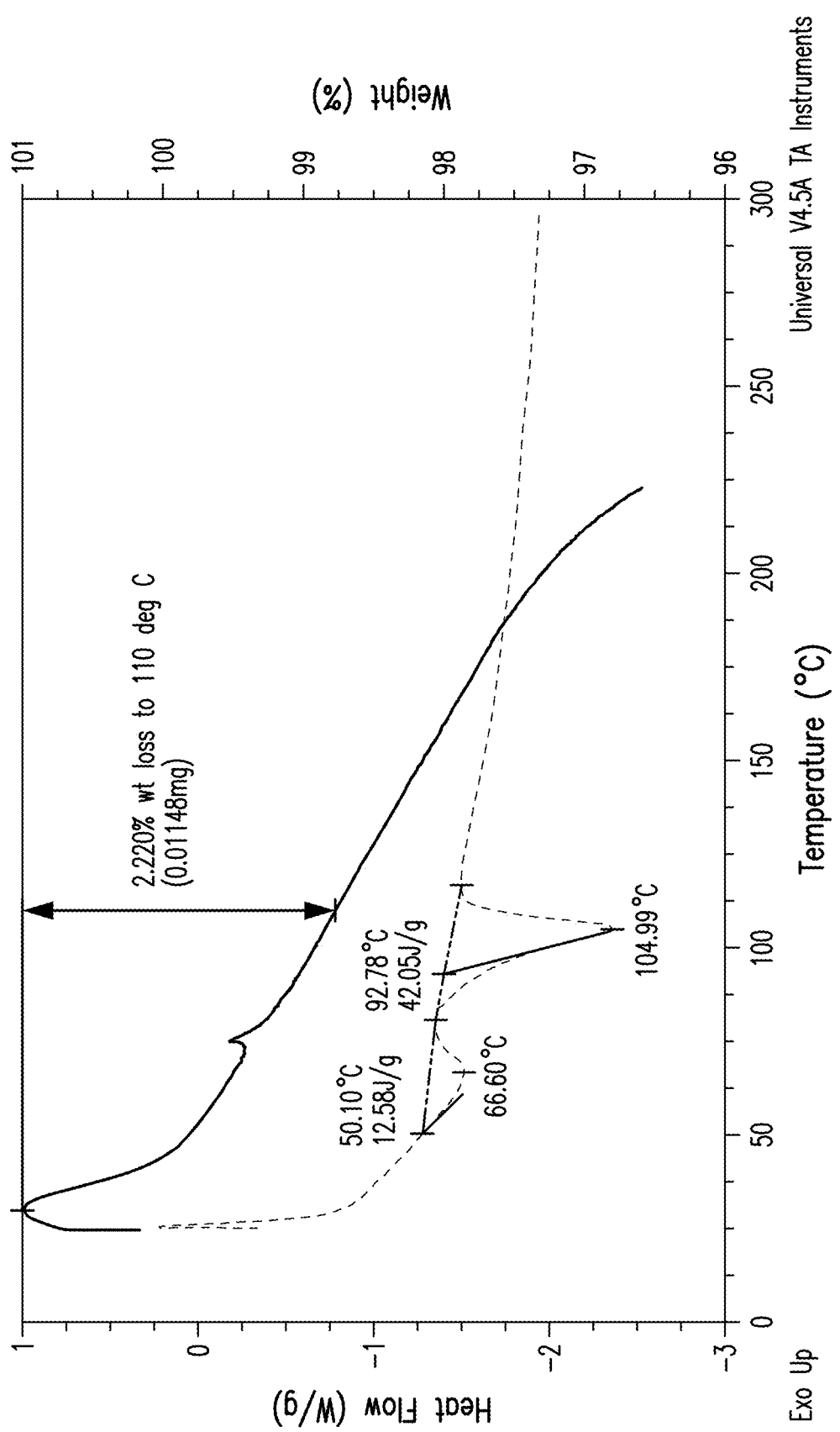
Figure 7B:
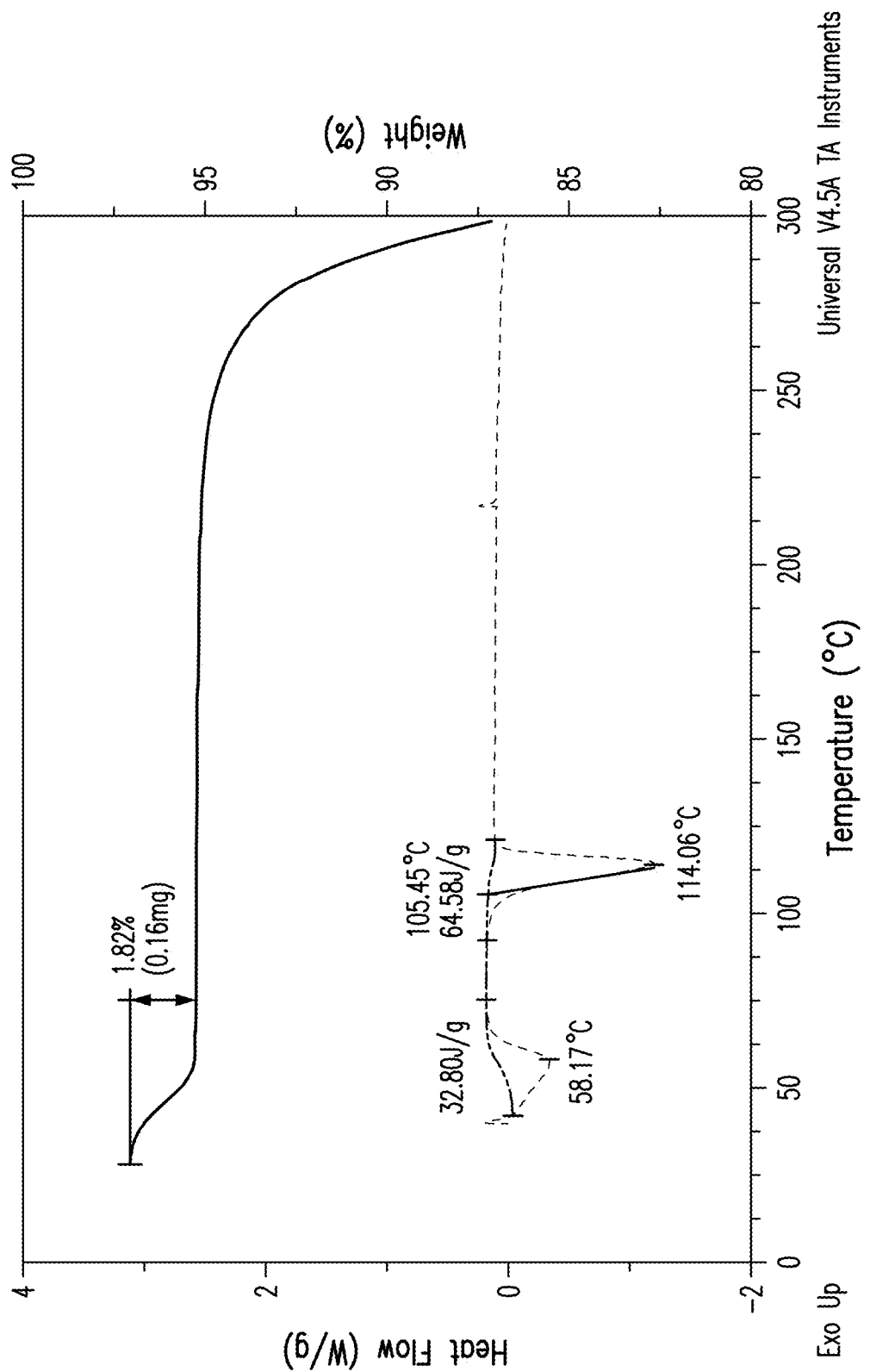
Figure 7C:
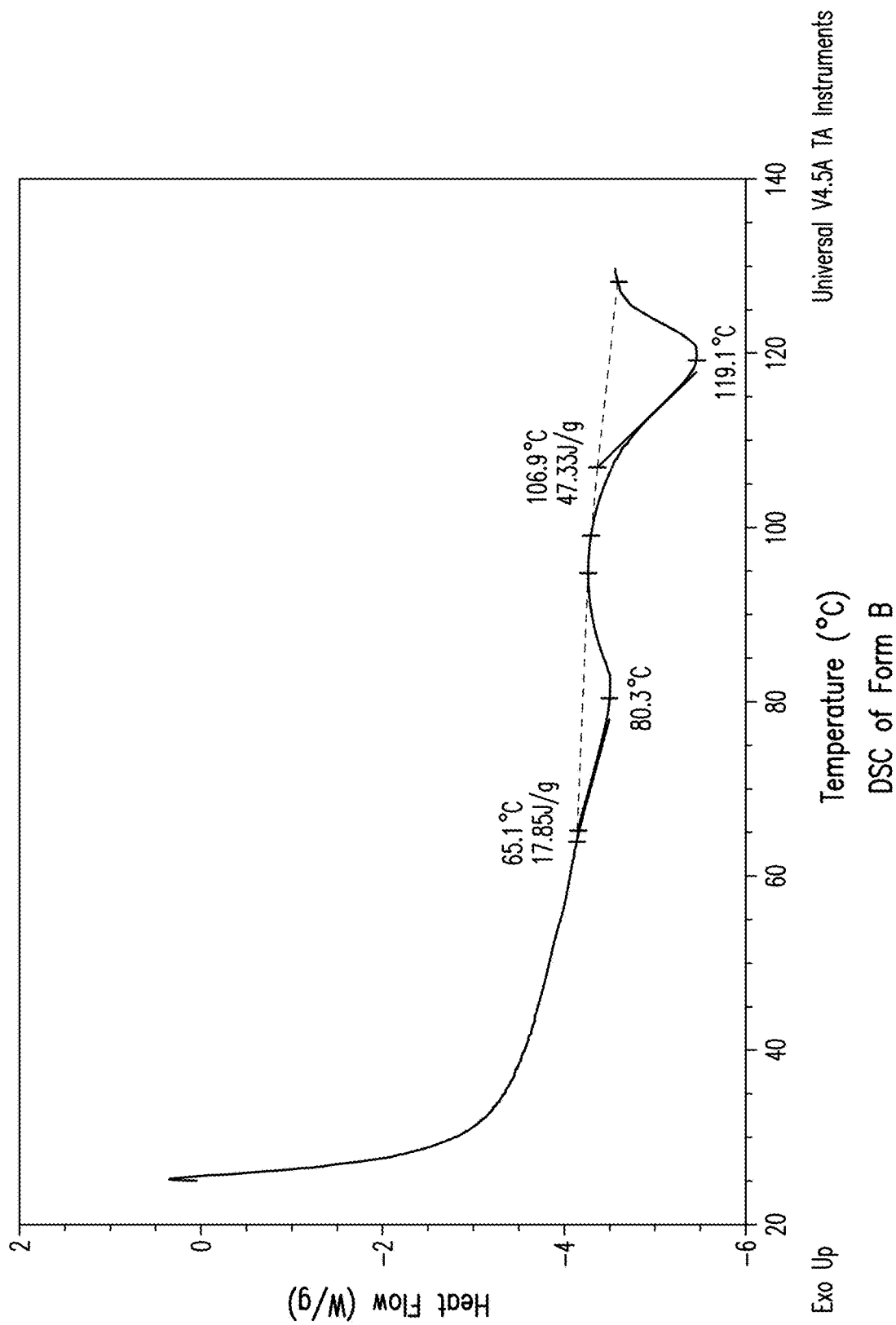

FIG. 7A provides representative DSC and TGA thermograms of Form B of Compound 1; FIG. 7B provides another representative DSC and TGA thermograms of Form B of Compound 1; and FIG. 7C provides another representative DSC thermogram of Form B of Compound 1.

Figure 8:
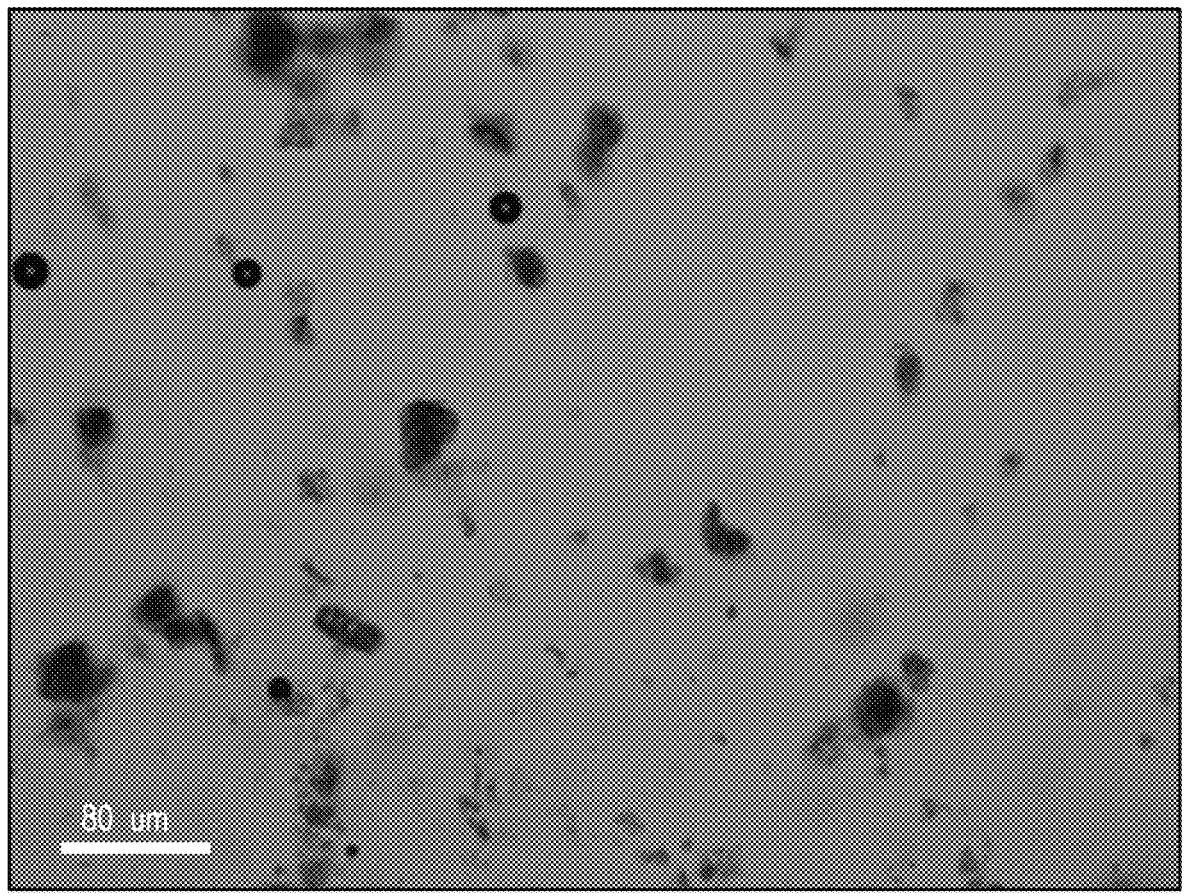

FIG. 8 provides a representative PLM image of Form B of Compound 1.

Figure 9:
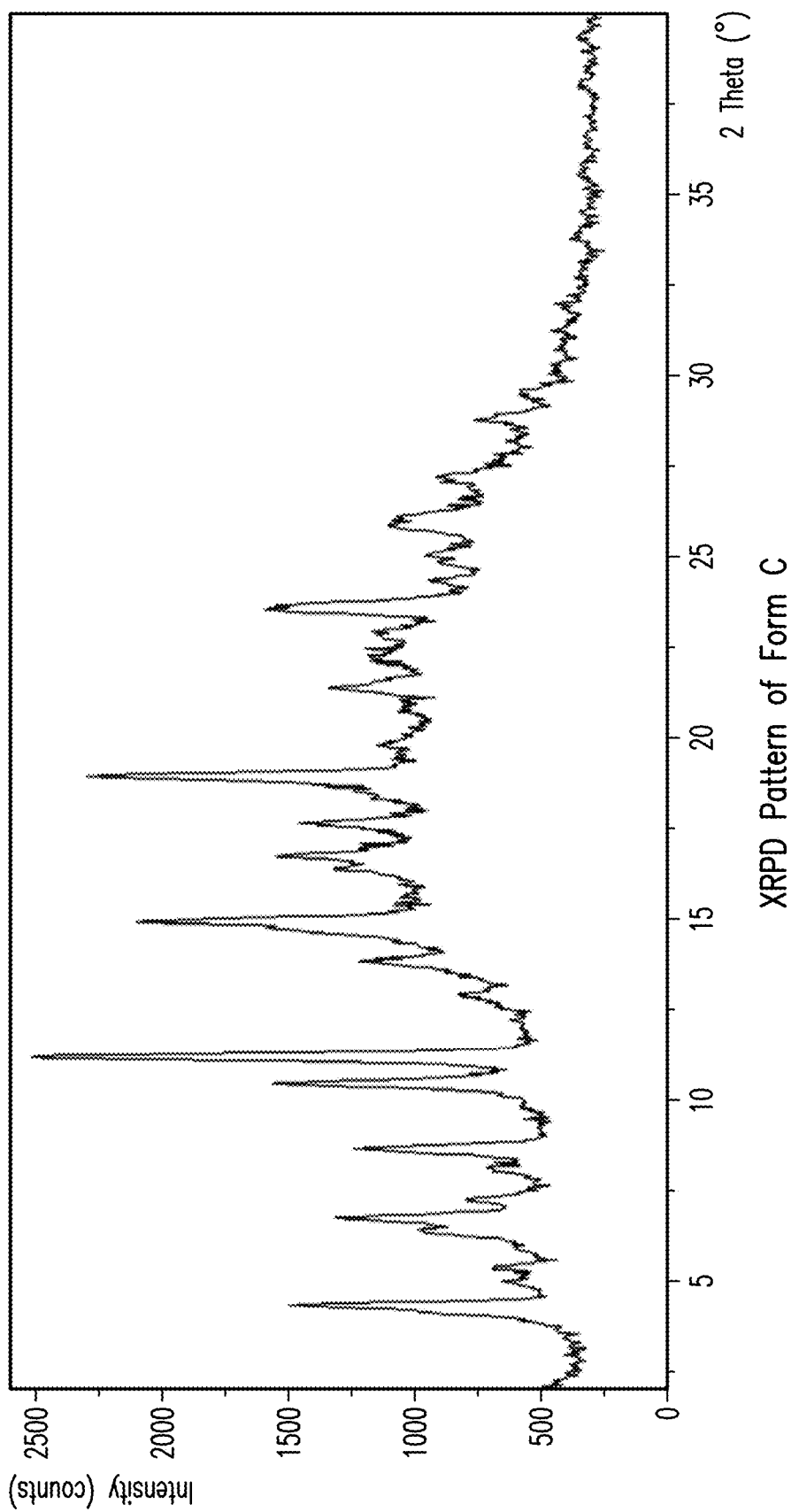

FIG. 9 provides a representative XRPD pattern of Form C of Compound 1.

Figure 10:
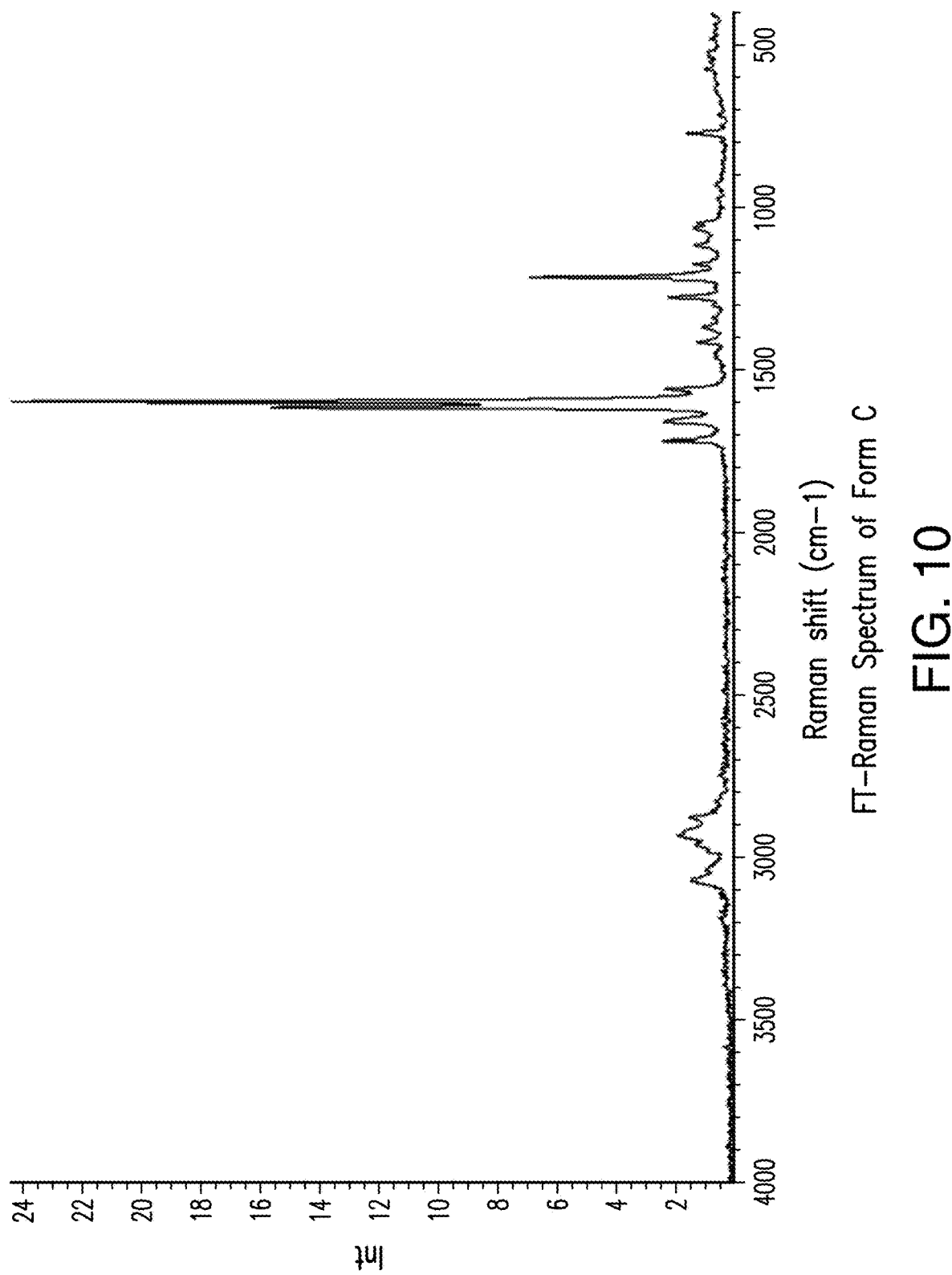

FIG. 10 provides a representative FT-Raman spectrum of Form C of Compound 1.

Figure 11:
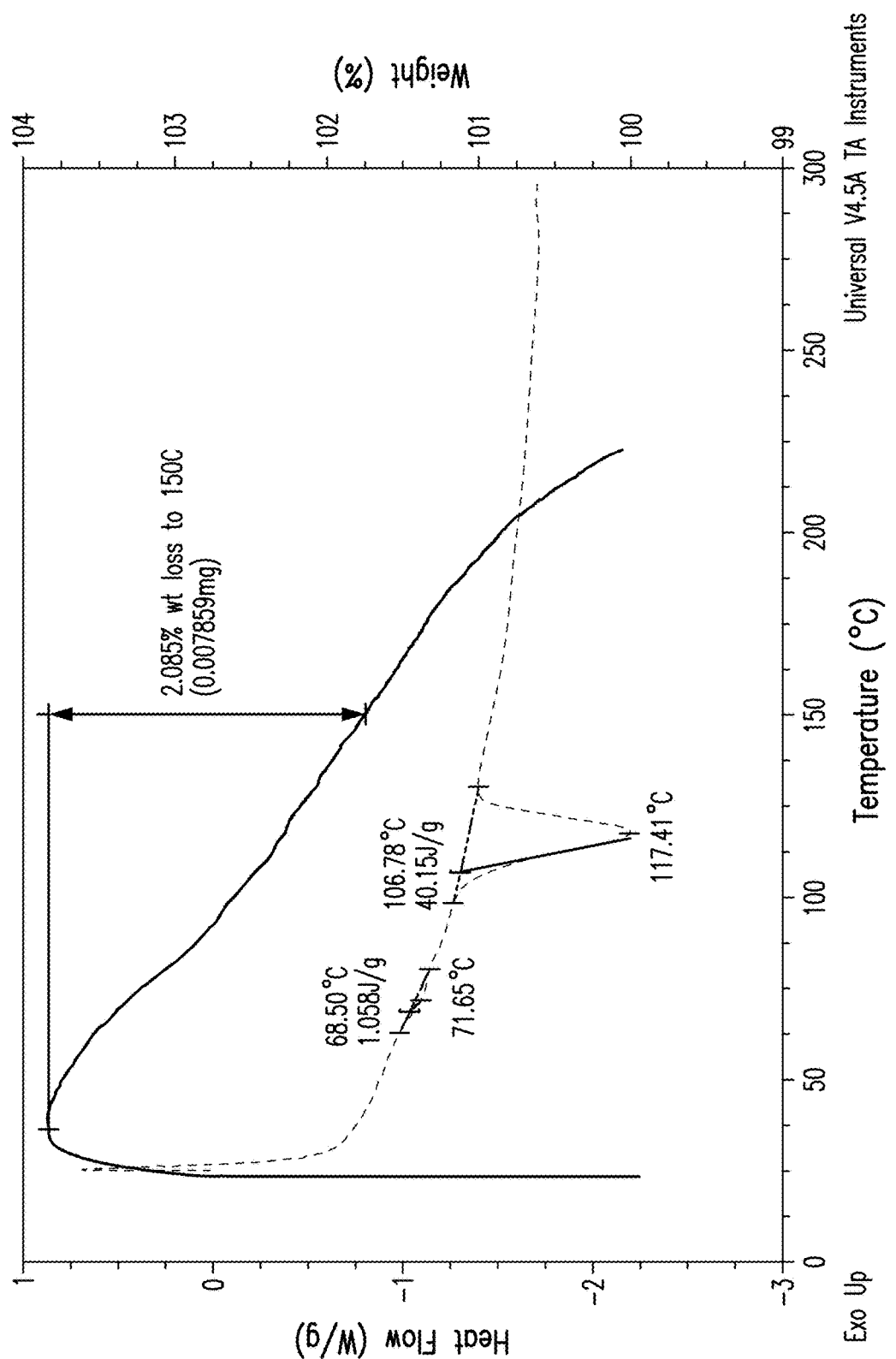

FIG. 11 provides representative DSC and TGA thermograms of Form C of Compound 1.

Figure 12:
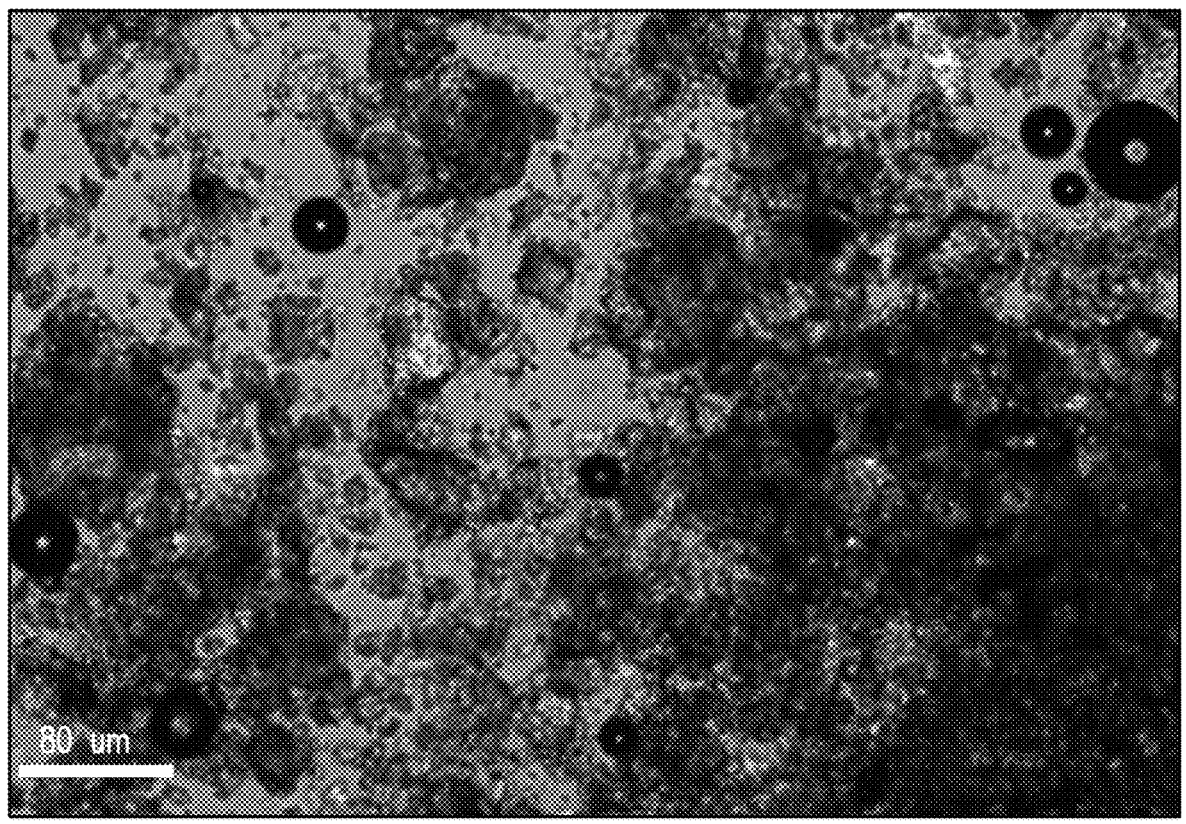

FIG. 12 provides a representative PLM image of Form C of Compound 1.

Figure 13:
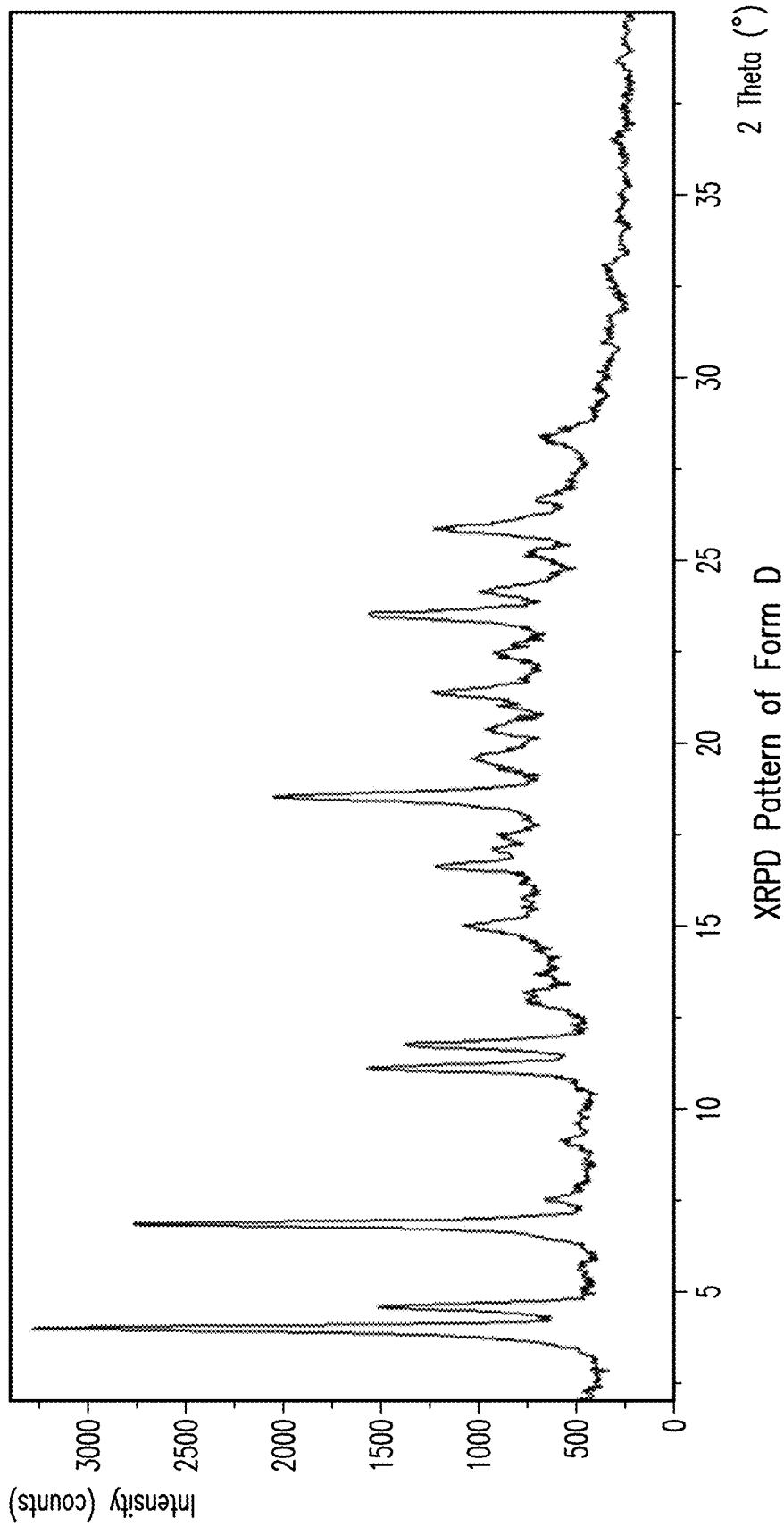

FIG. 13 provides a representative XRPD pattern of Form D of Compound 1.

Figure 14:
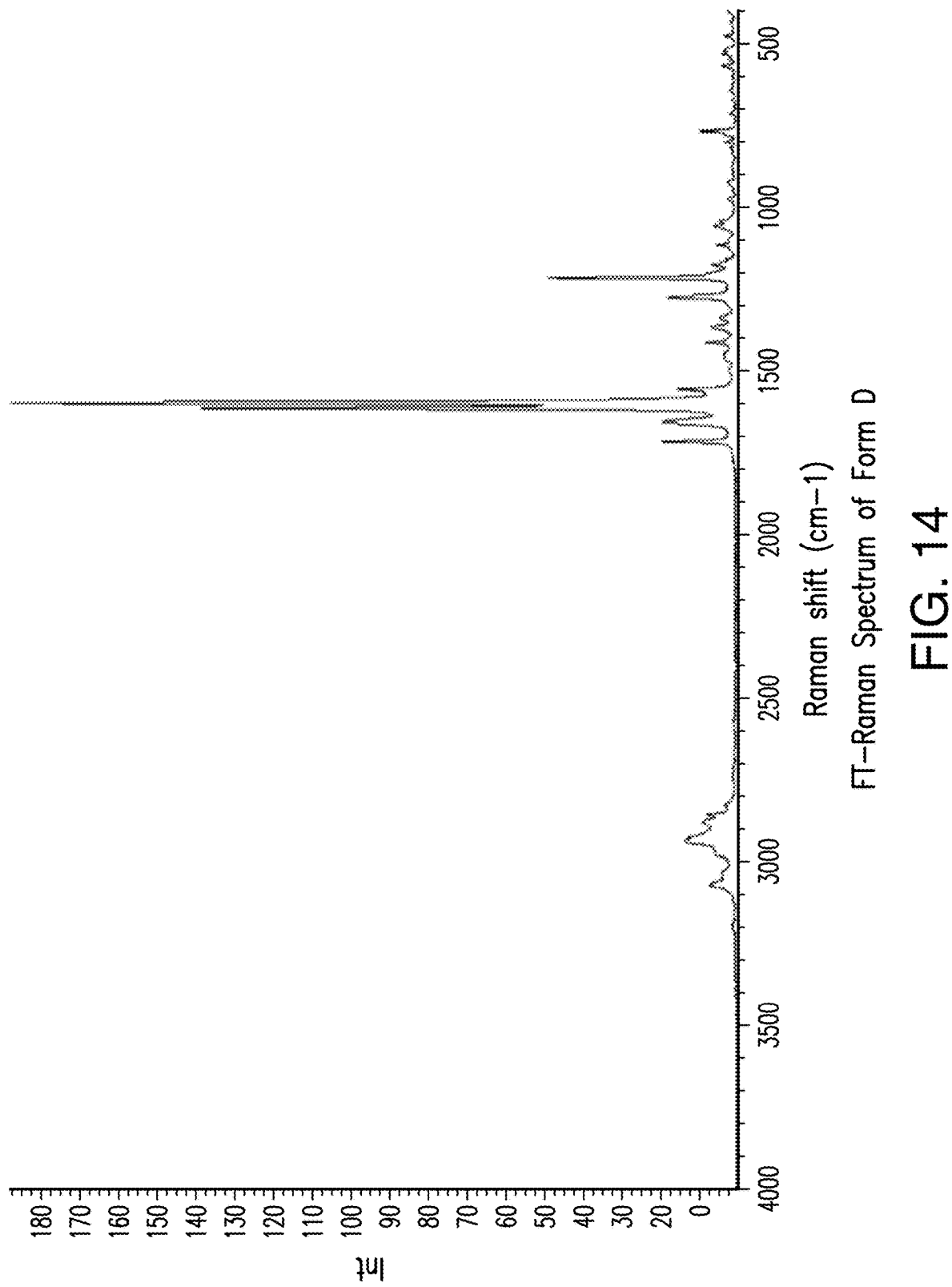

FIG. 14 provides a representative FT-Raman spectrum of Form D of Compound 1.

Figure 15:
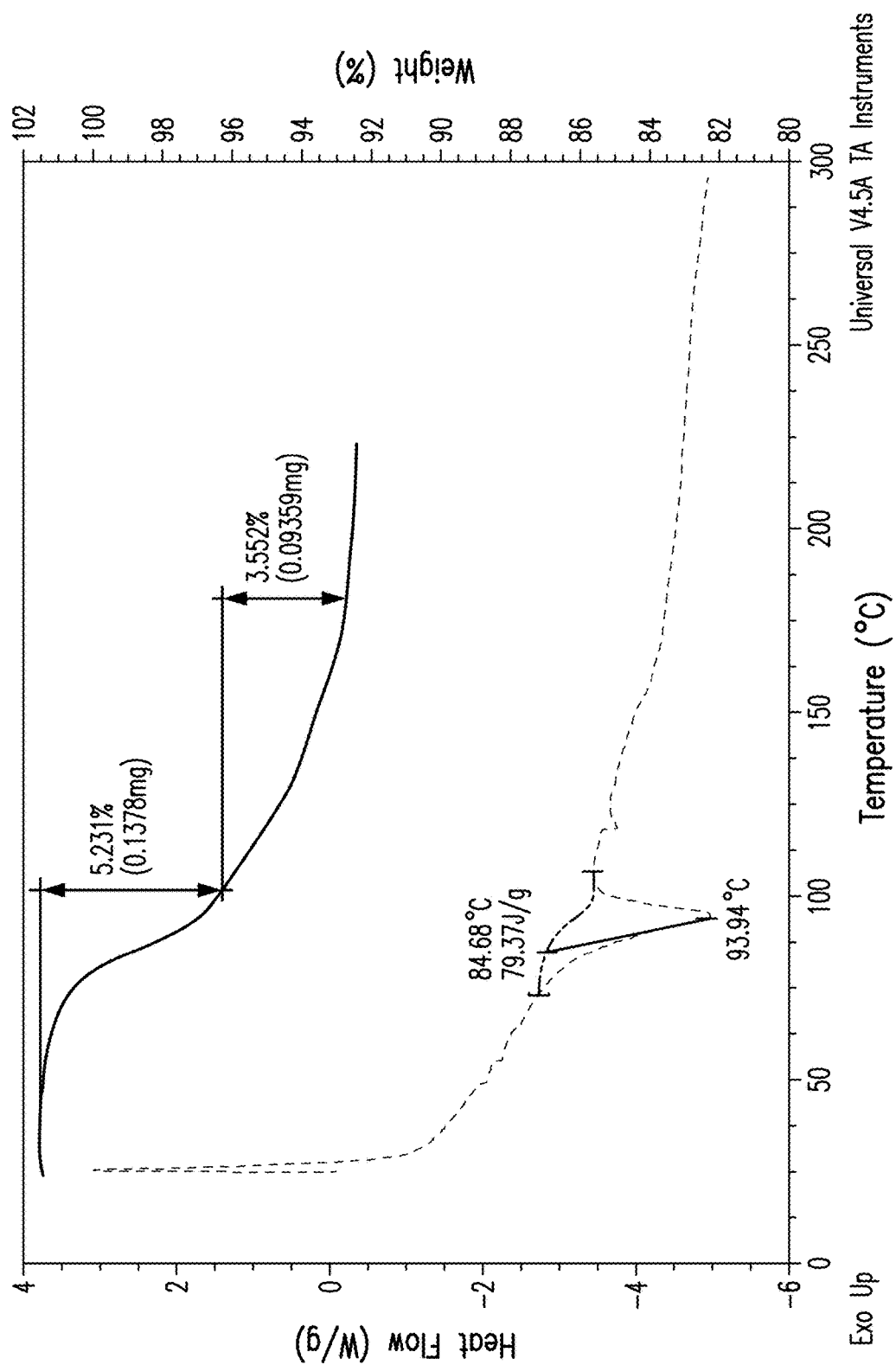

FIG. 15 provides representative DSC and TGA thermograms of Form D of Compound 1.

Figure 16:
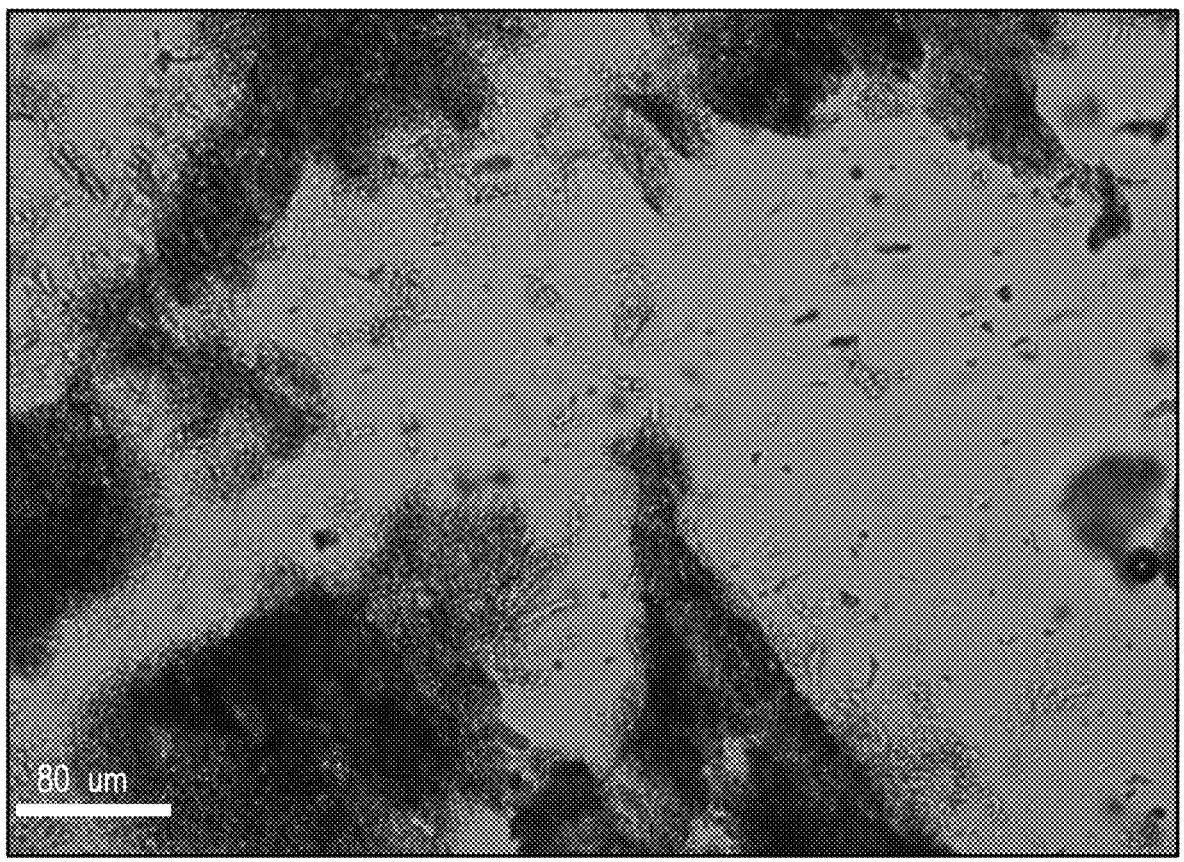

FIG. 16 provides a representative PLM image of Form D of Compound 1.

Figure 17:
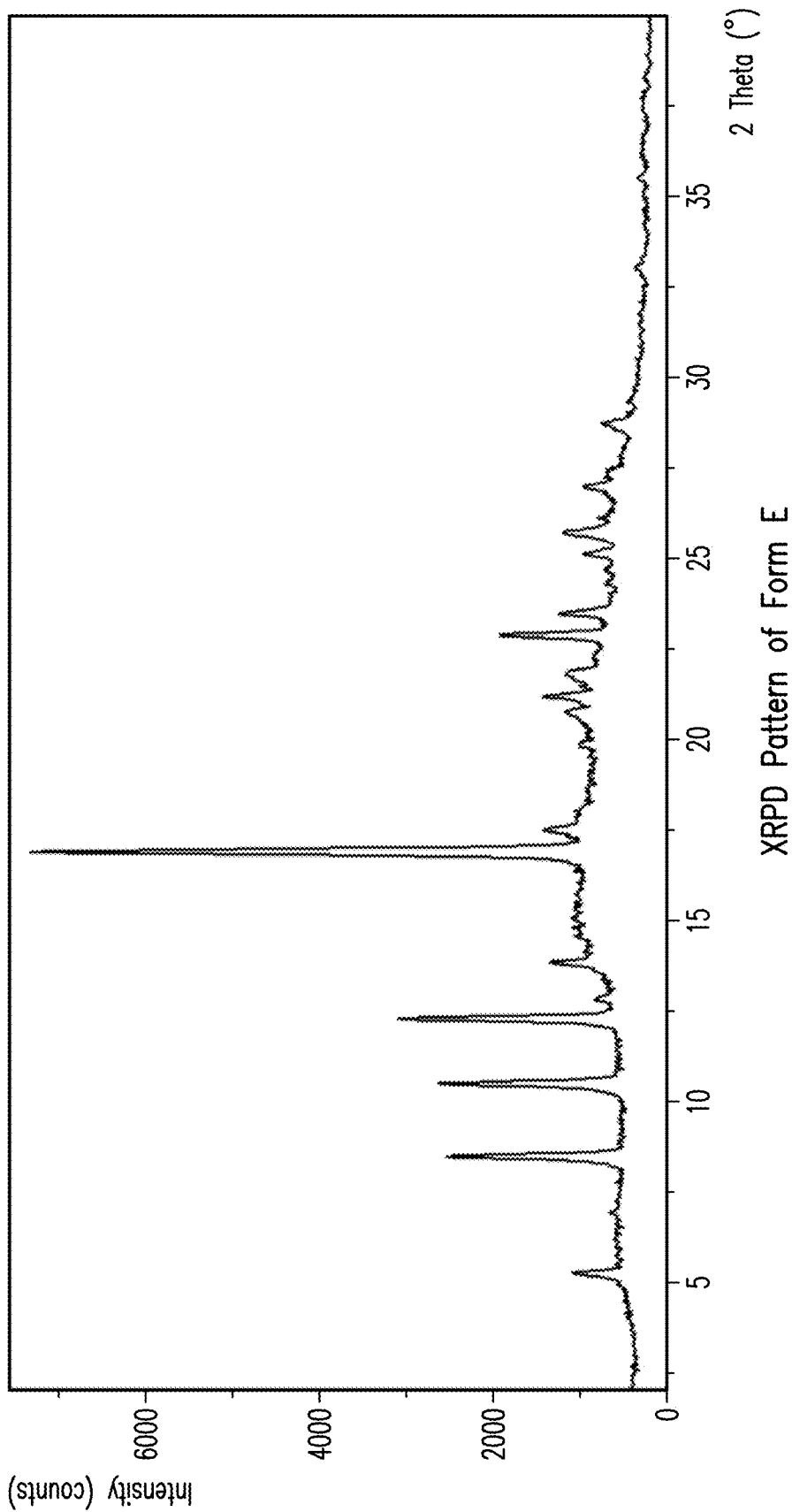

FIG. 17 provides a representative XRPD pattern of Form E of Compound 1.

Figure 18:
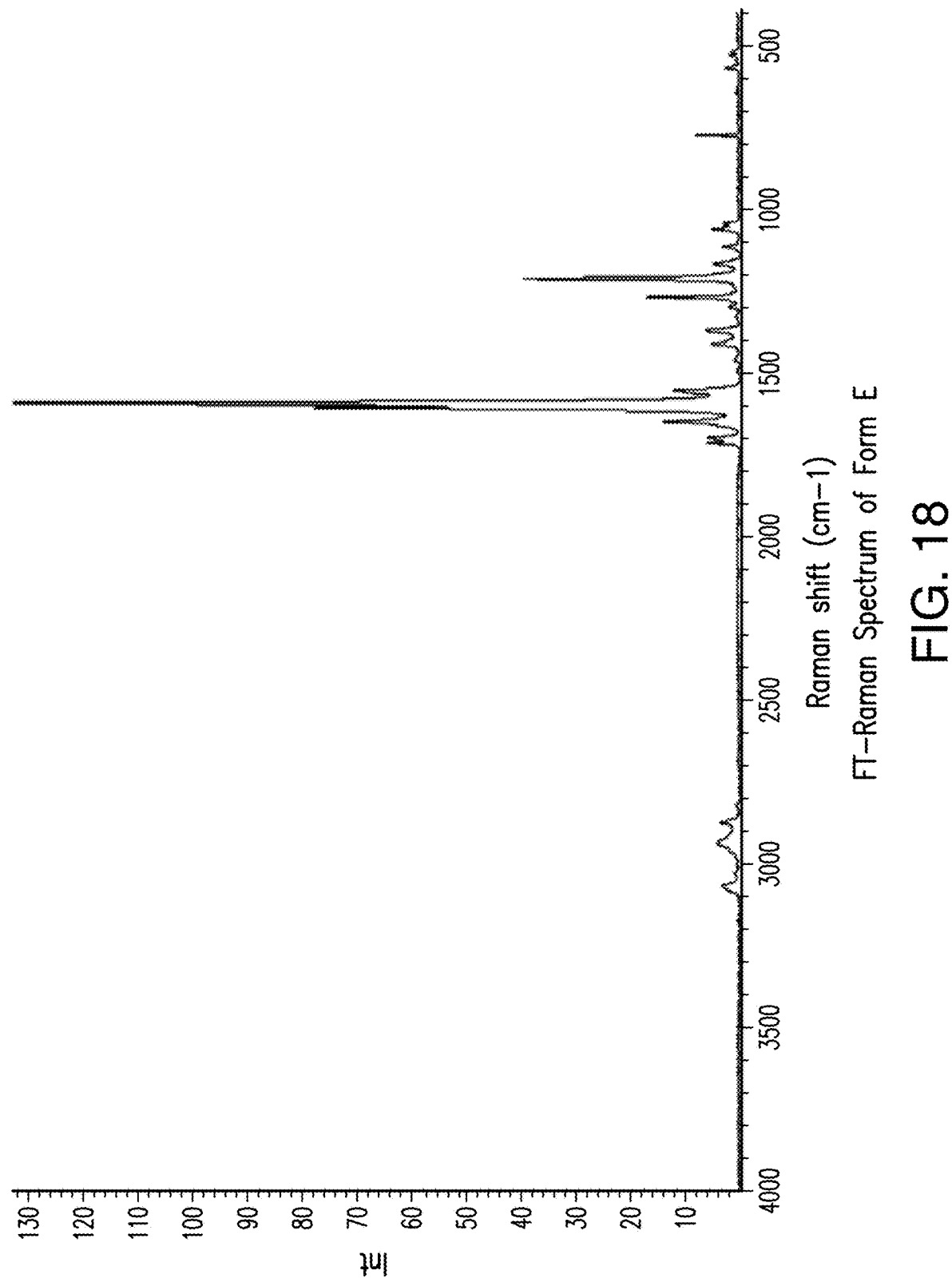

FIG. 18 provides a representative FT-Raman spectrum of Form E of Compound 1.

Figure 19:
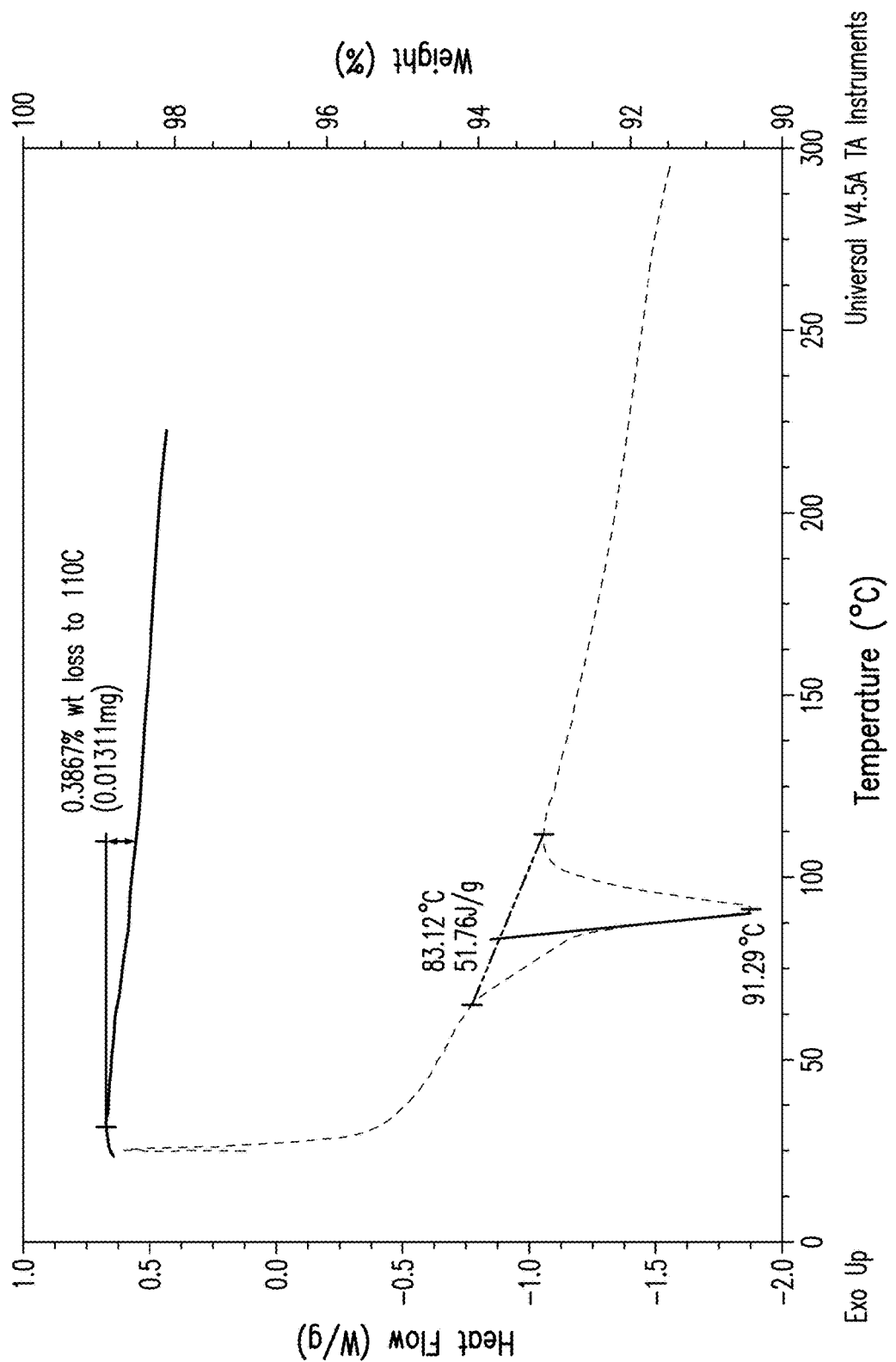

FIG. 19 provides representative DSC and TGA thermograms of Form E of Compound 1.

Figure 20:
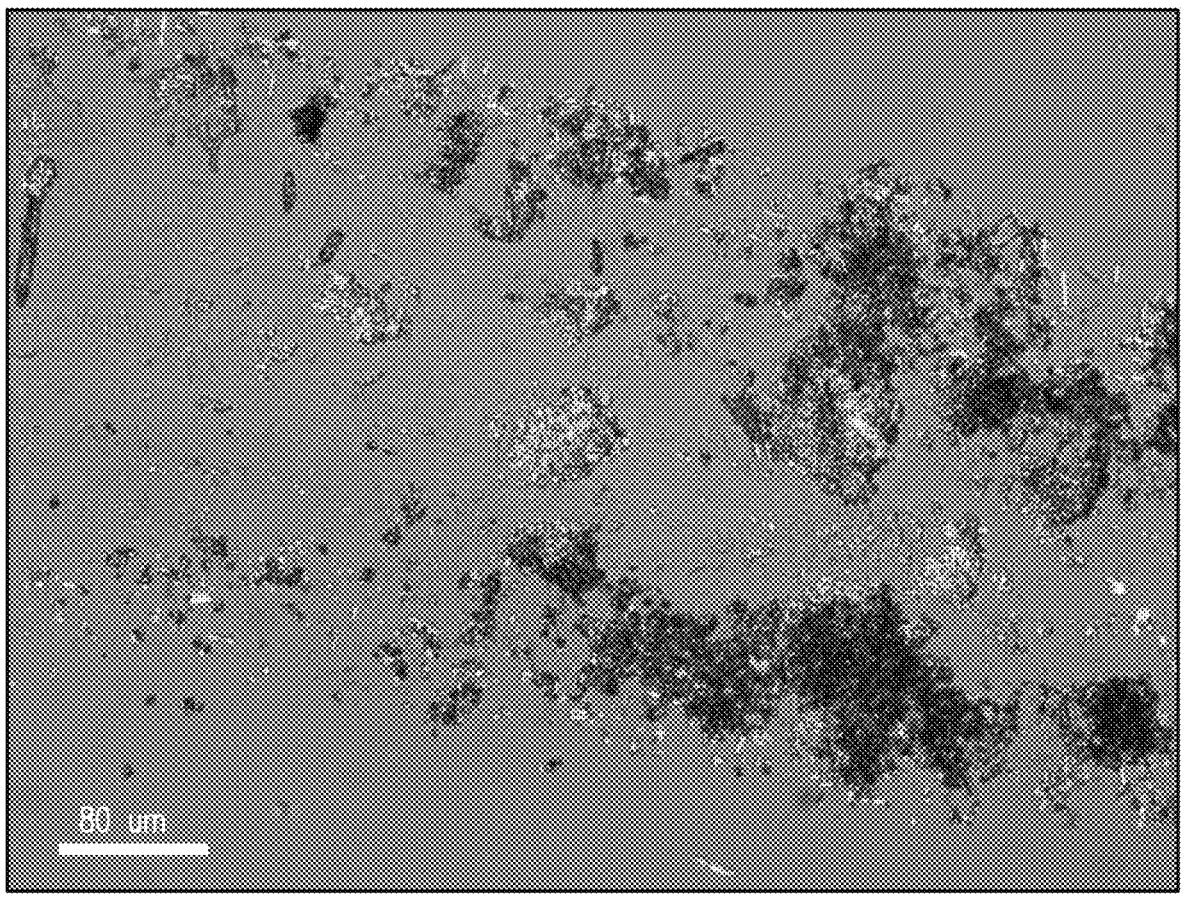

FIG. 20 provides a representative PLM image of Form E of Compound 1.

Figure 21:
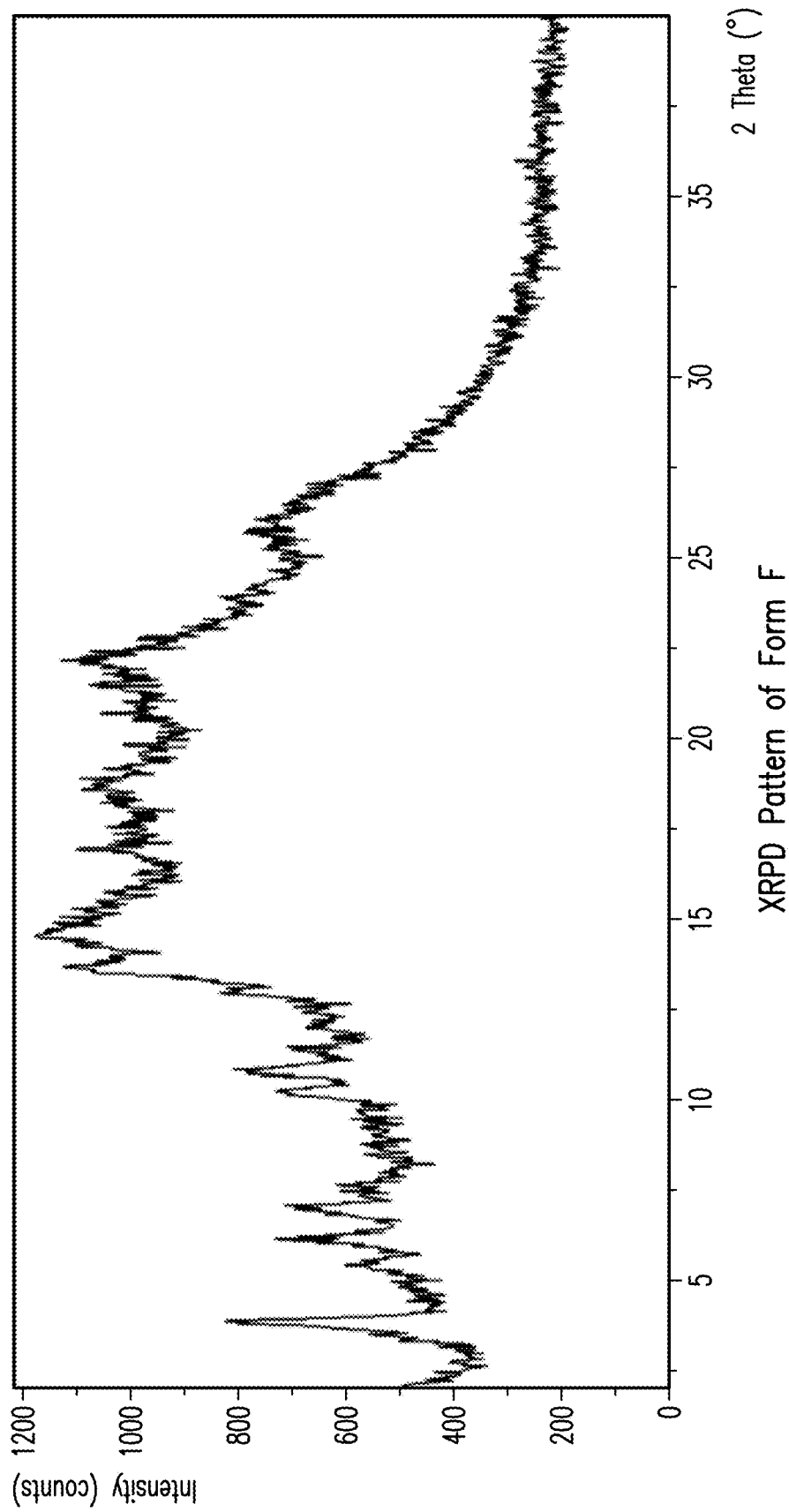

FIG. 21 provides a representative XRPD pattern of Form F of Compound 1.

Figure 22:
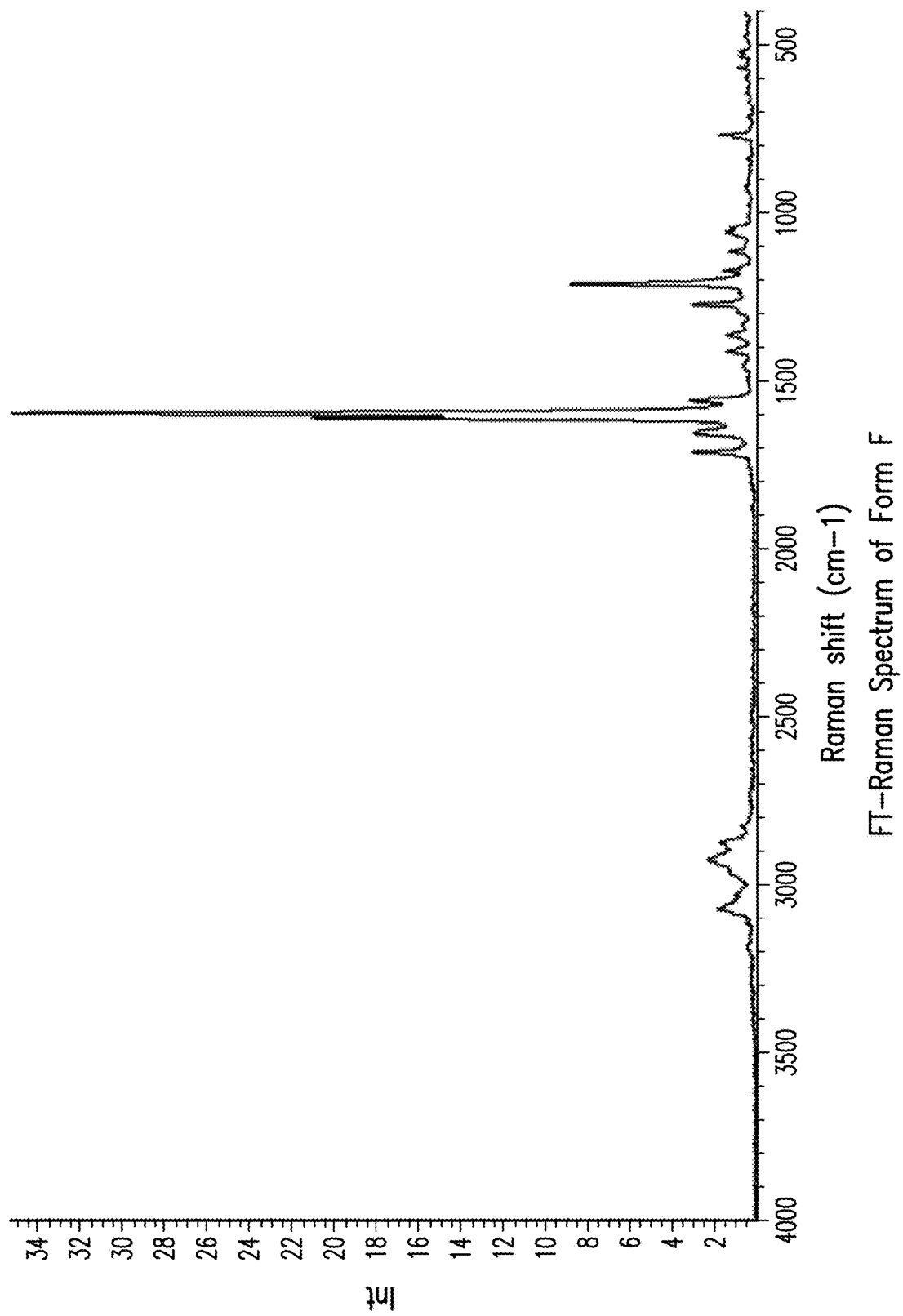

FIG. 22 provides a representative FT-Raman spectrum of Form F of Compound 1.

Figure 23:
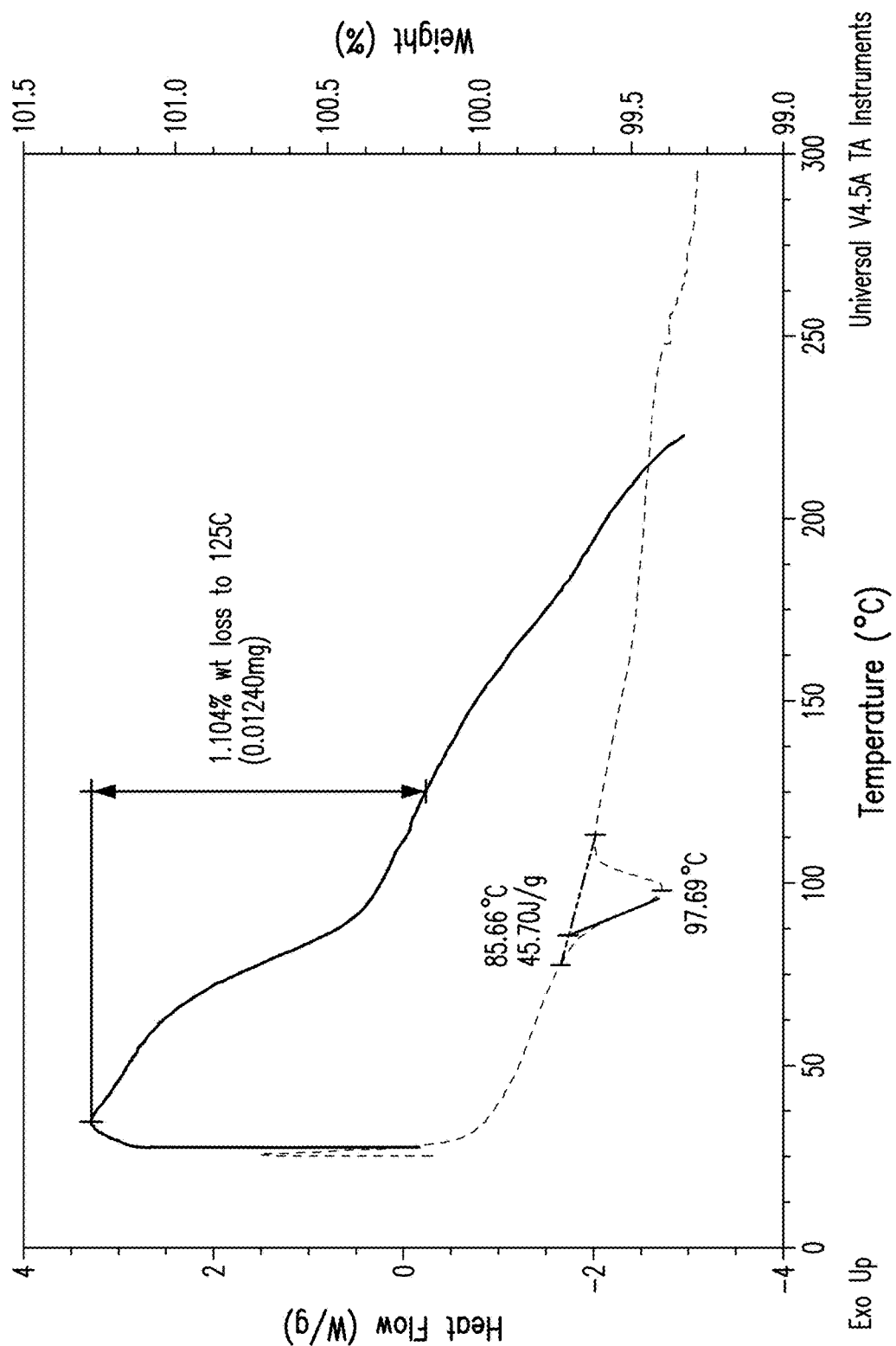

FIG. 23 provides representative DSC and TGA thermograms of Form F of Compound 1.

Figure 24:
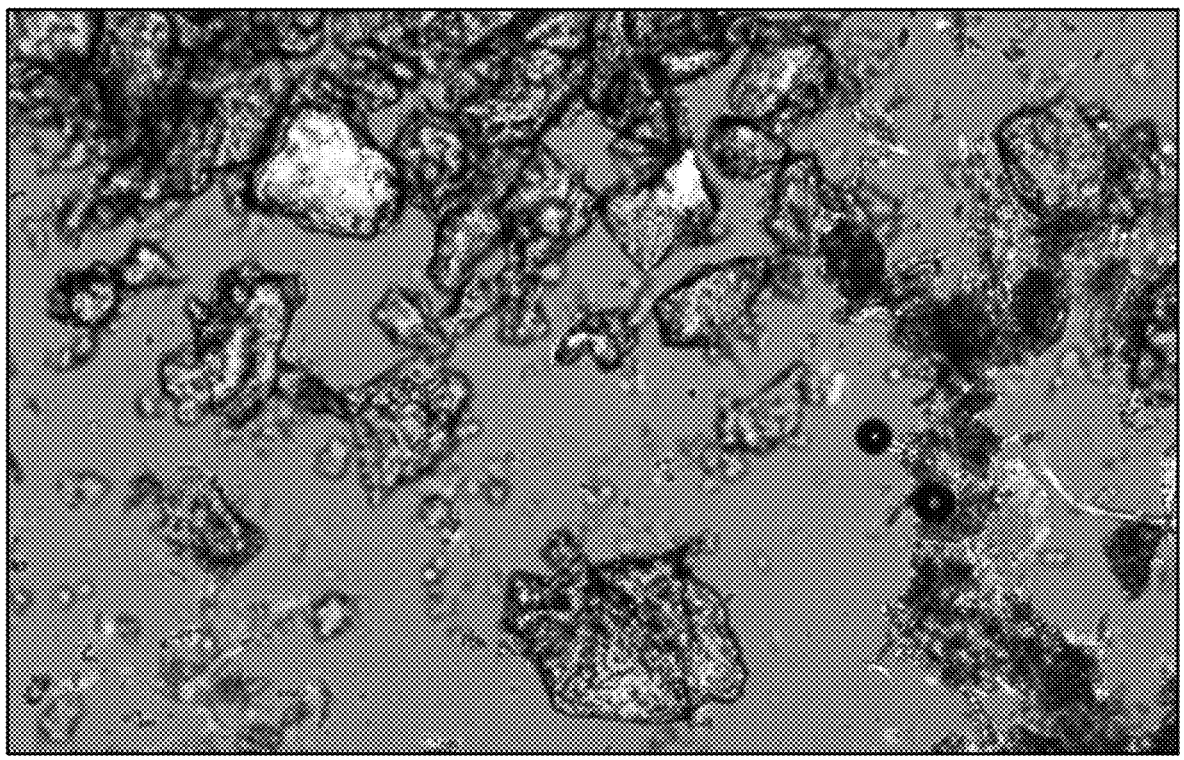

FIG. 24 provides a representative PLM image of Form F of Compound 1.

Figure 25:
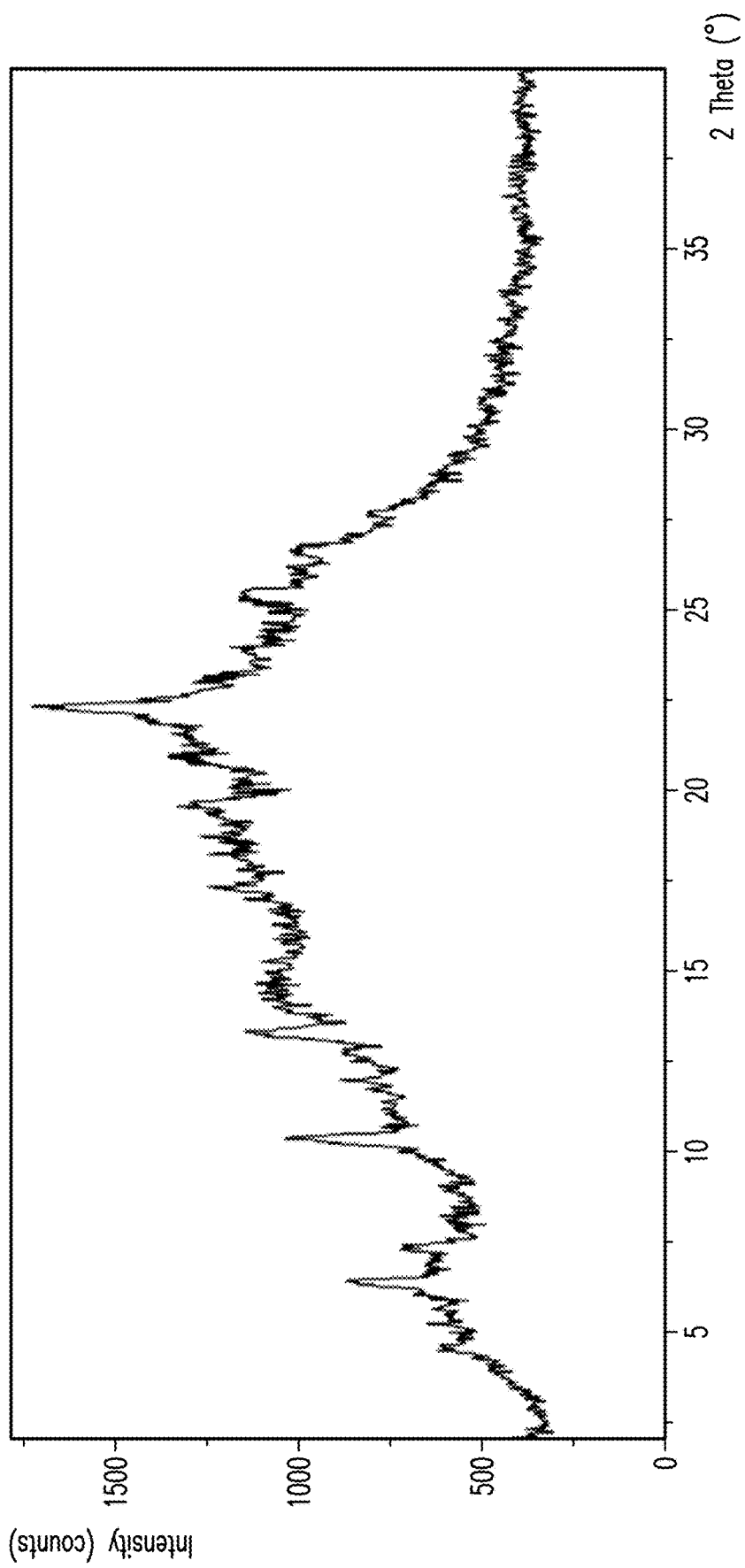

FIG. 25 provides a representative XRPD pattern of Form G of Compound 1.

Figure 26:
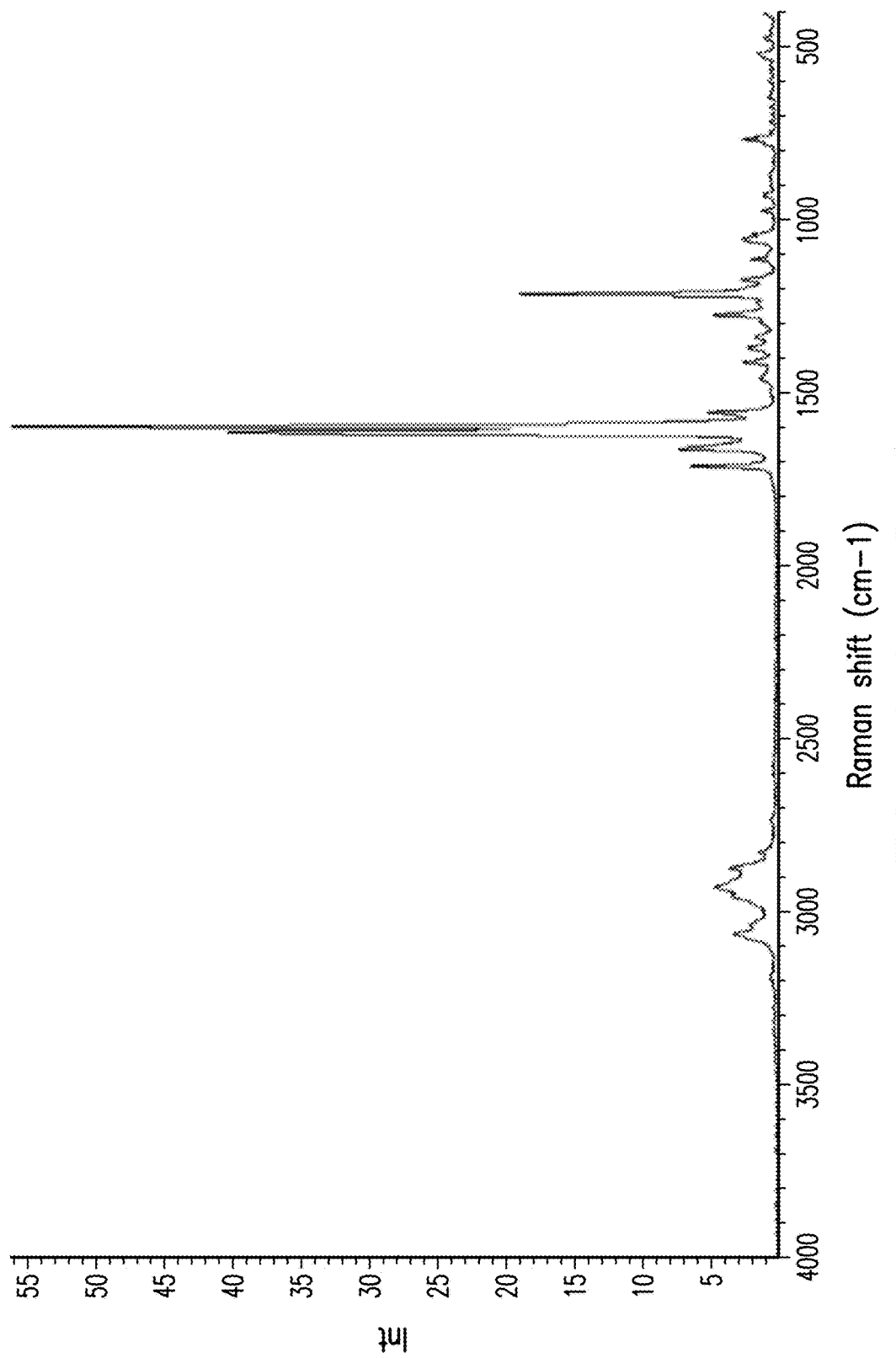

FIG. 26 provides a representative FT-Raman spectrum of Form G of Compound 1.

Figure 27:
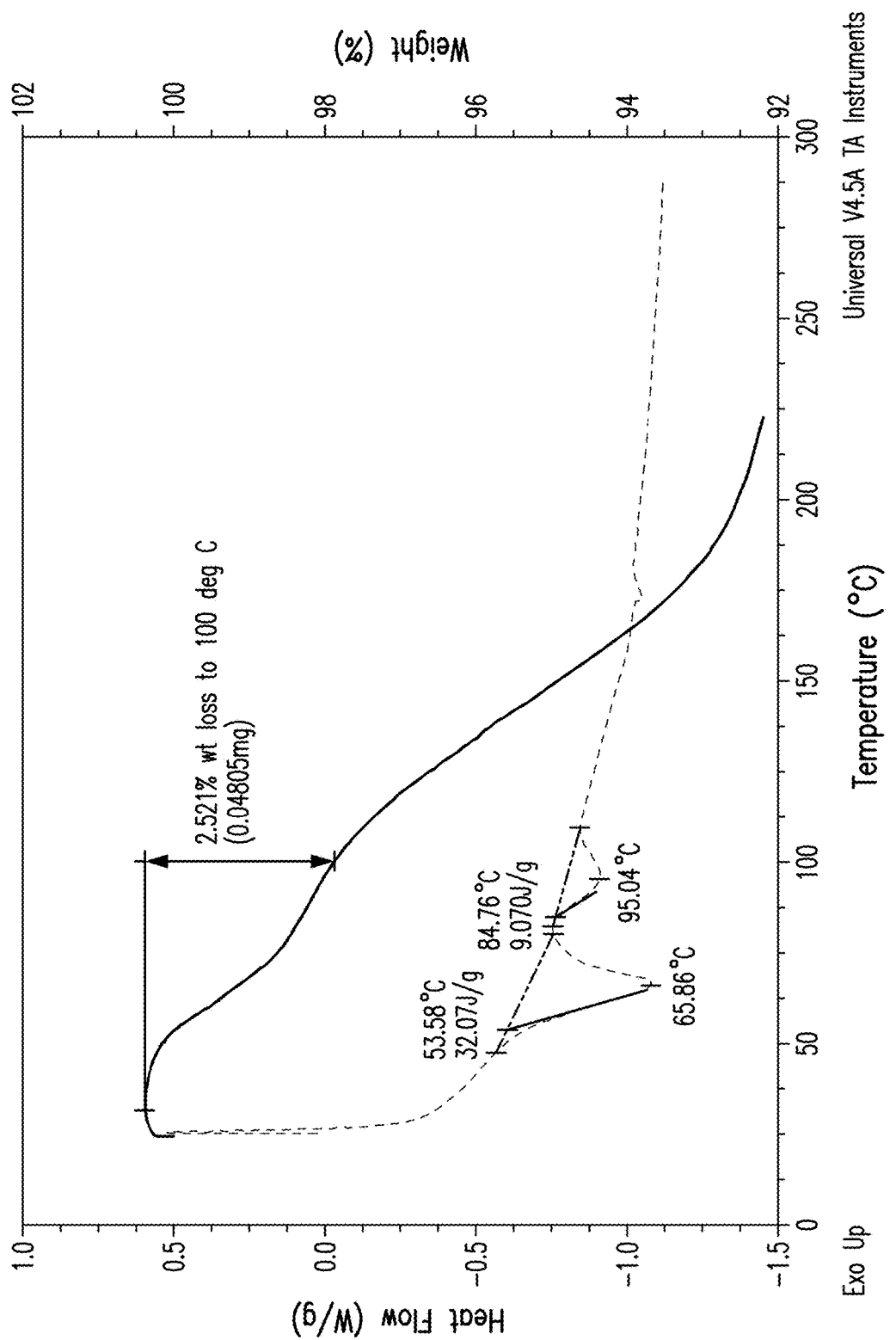

FIG. 27 provides representative DSC and TGA thermograms of Form G of Compound 1.

Figure 28:
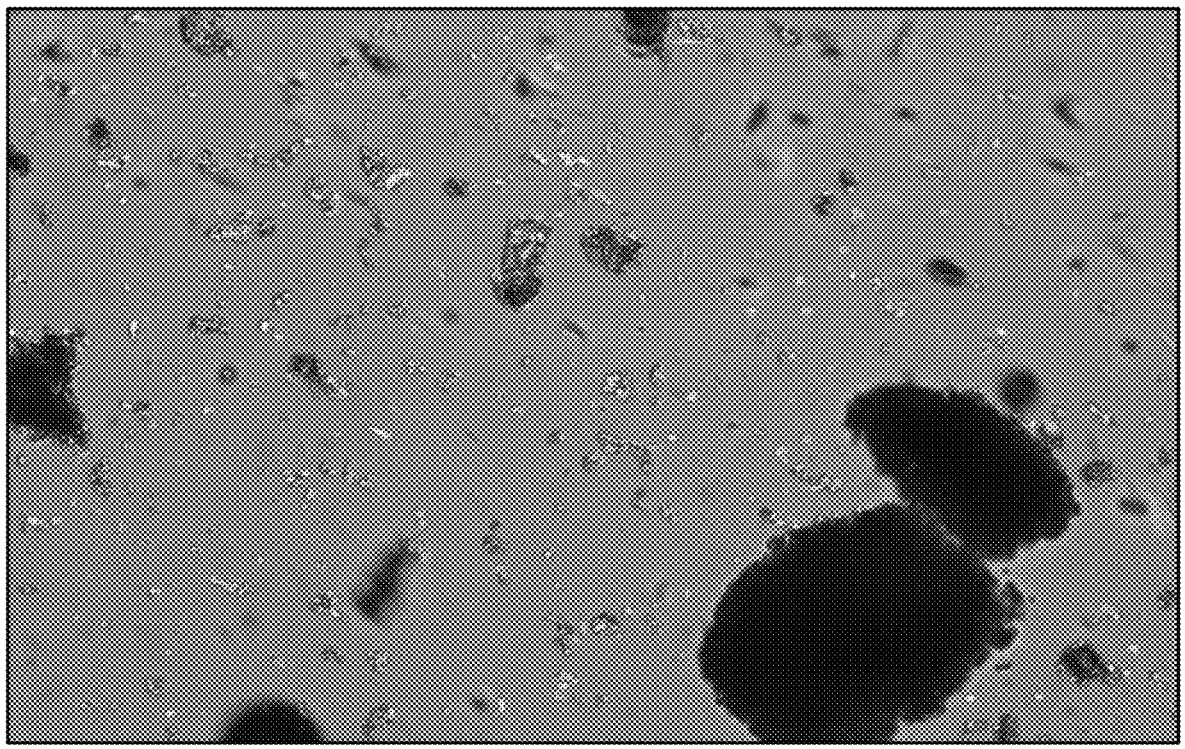

FIG. 28 provides a representative PLM image of Form G of Compound 1.

Figure 29:
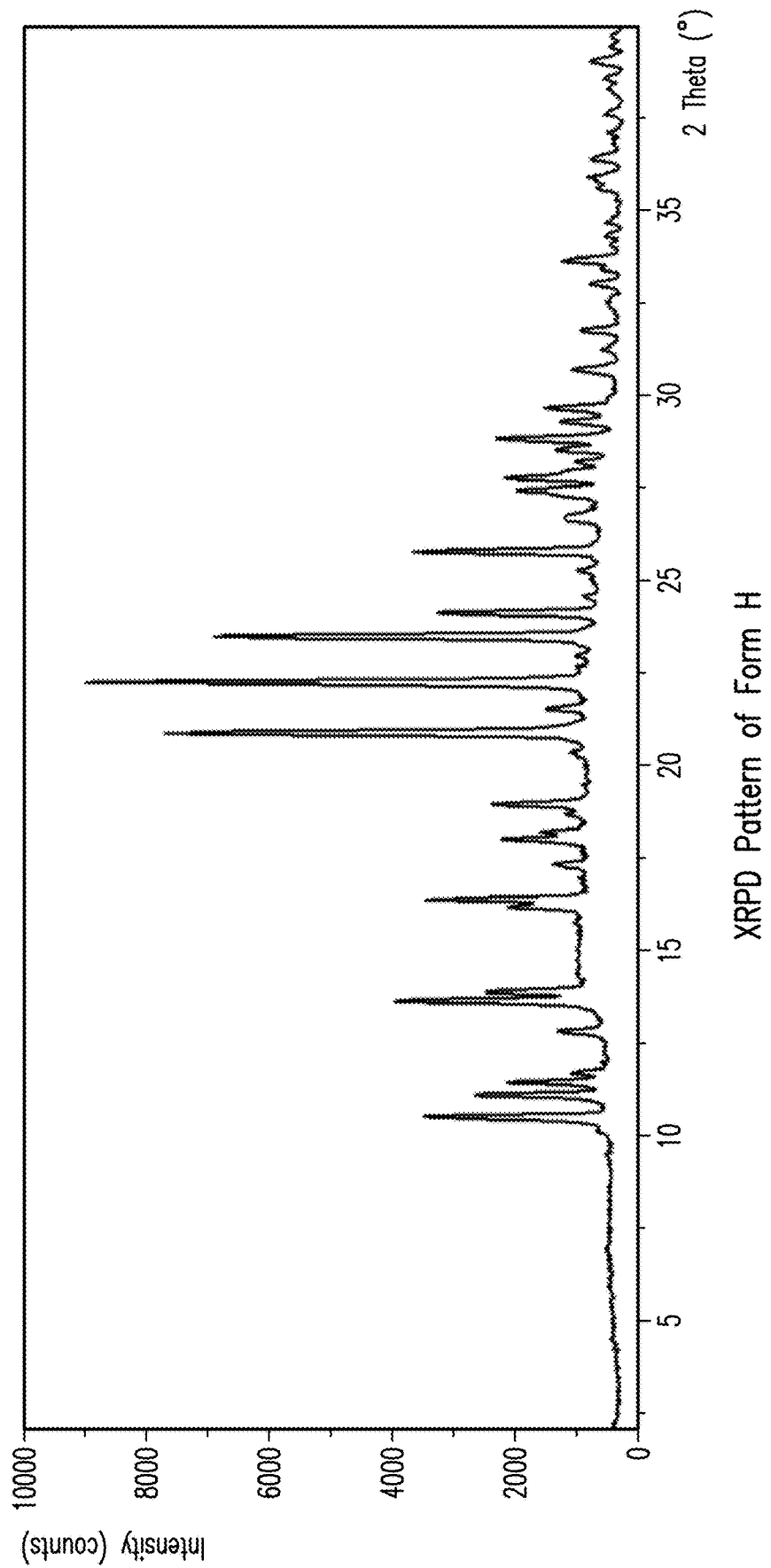

FIG. 29 provides a representative XRPD pattern of Form H of Compound 1.

Figure 30:
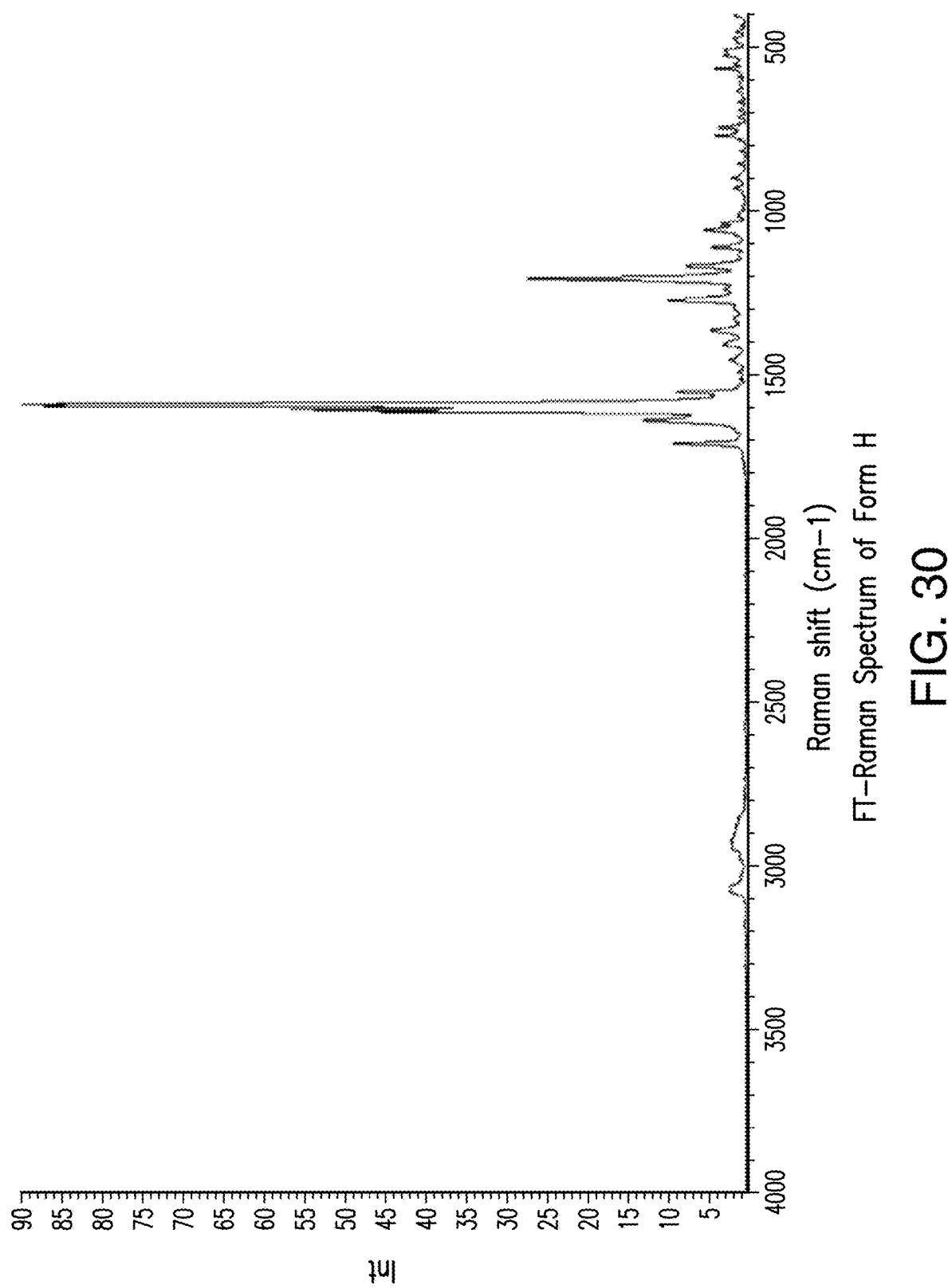

FIG. 30 provides a representative FT-Raman spectrum of Form H of Compound 1.

Figure 31:
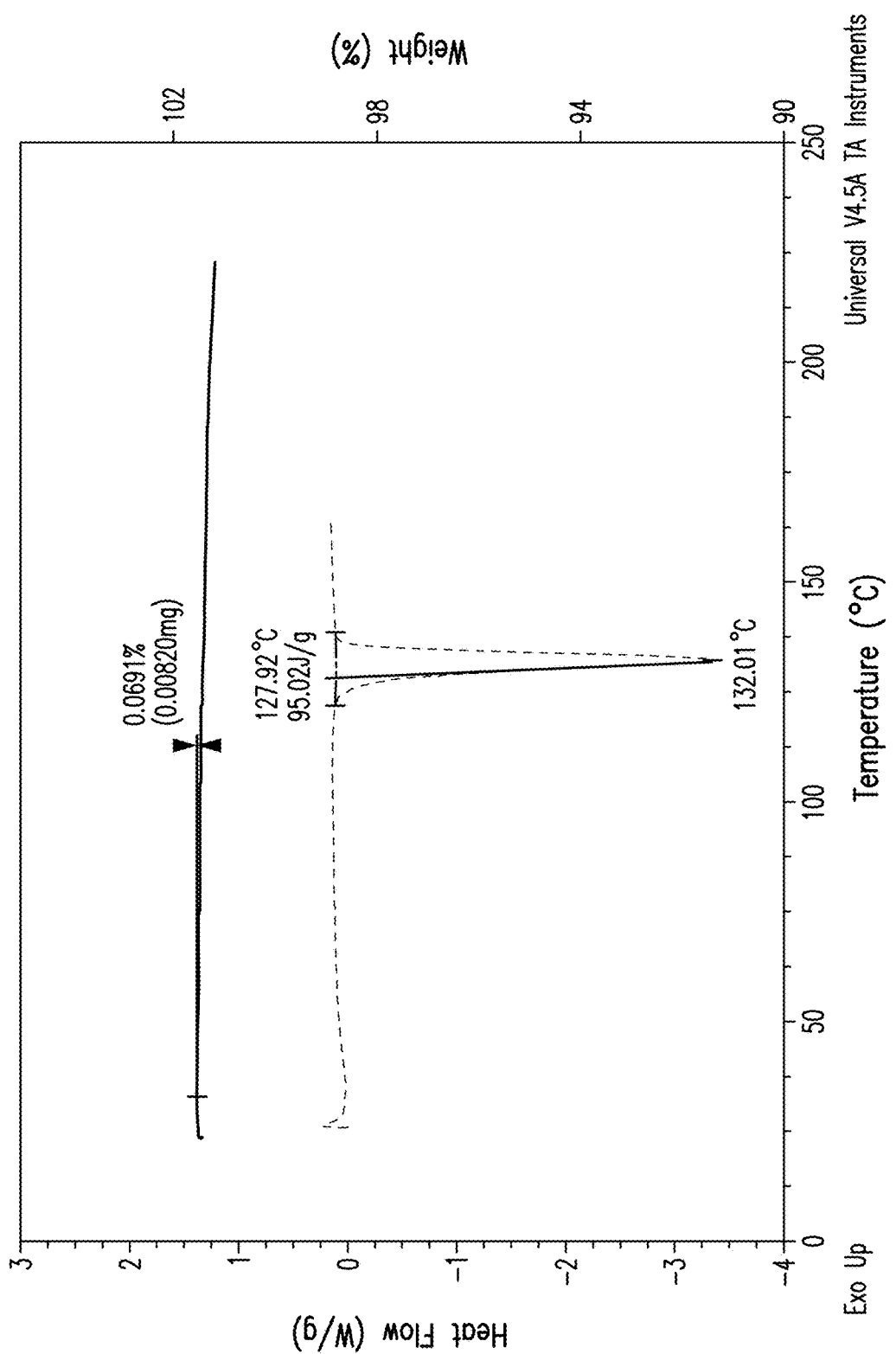

FIG. 31 provides representative DSC and TGA thermograms of Form H of Compound 1.

Figure 32:
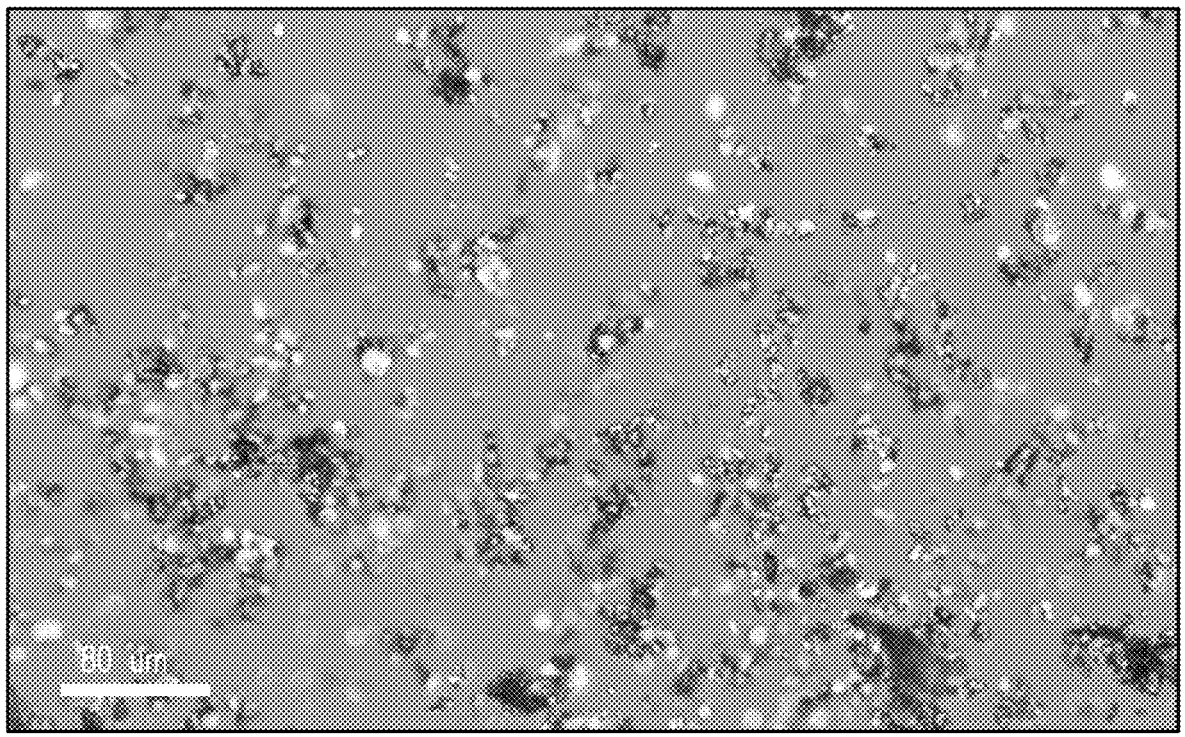

FIG. 32 provides a representative PLM image of Form H of Compound 1.

Figure 33:
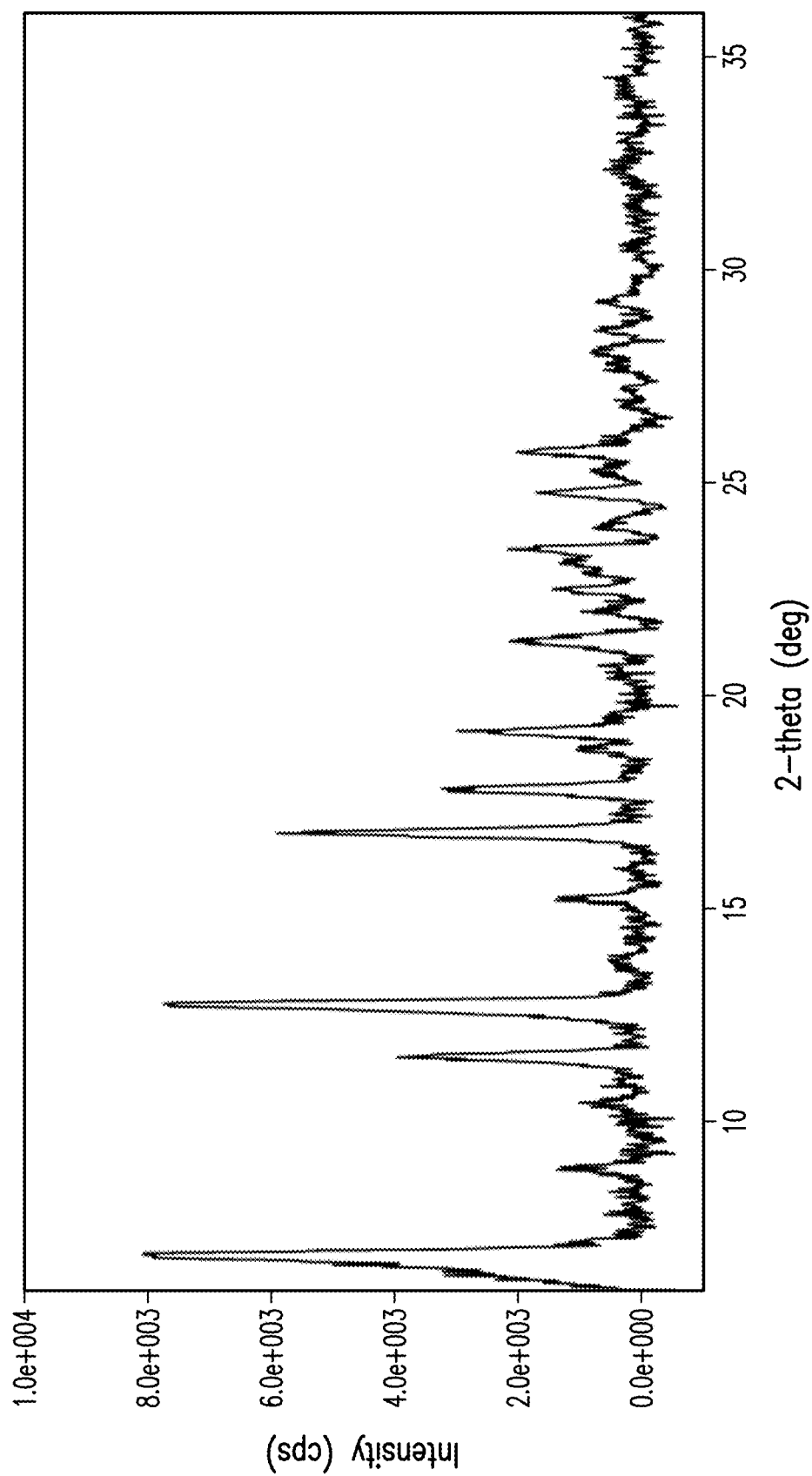

FIG. 33 provides a representative XRPD pattern of Form I of Compound 1.

Figure 34:
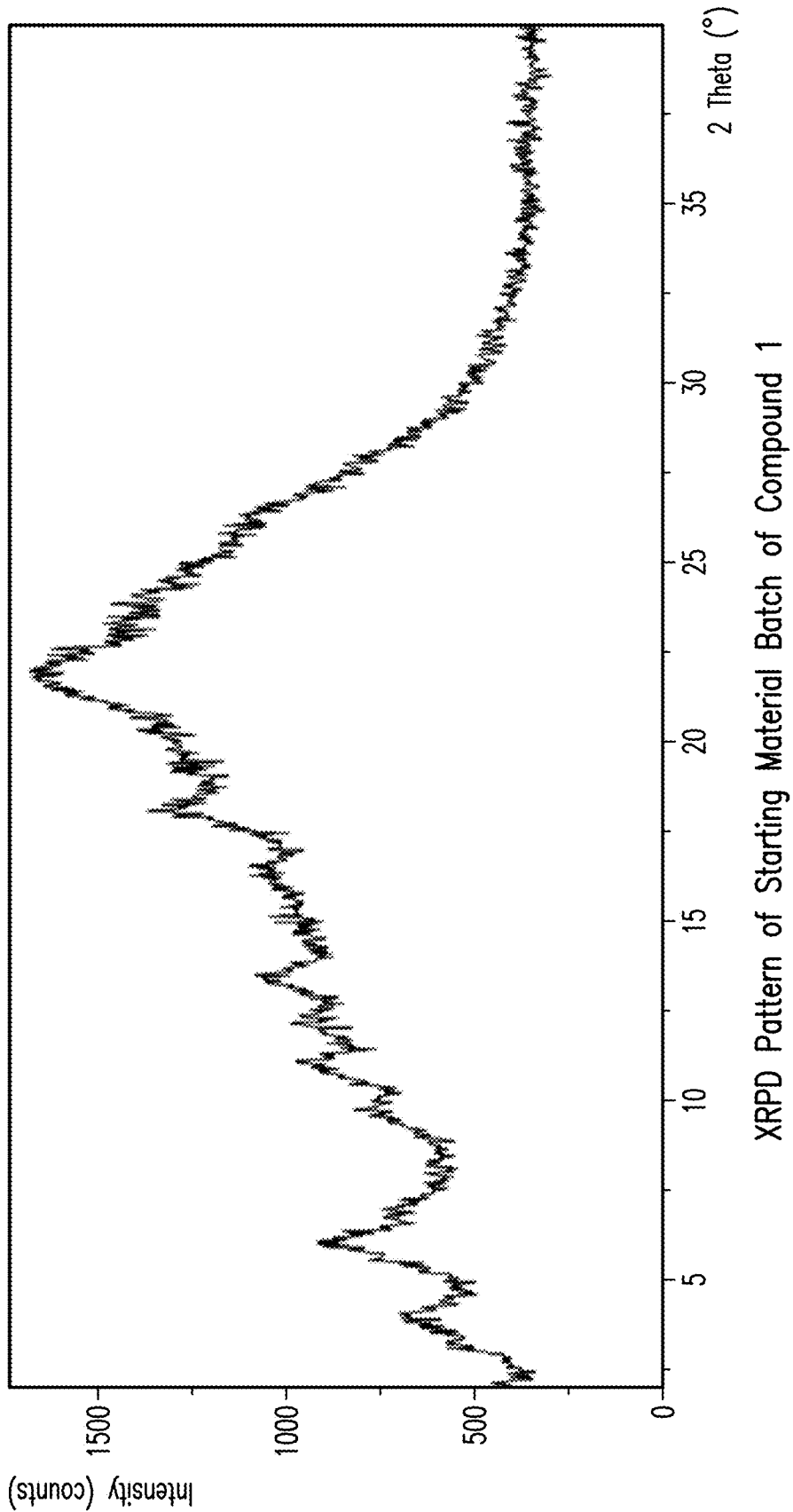

FIG. 34 provides a representative XRPD pattern of the starting material batch of Compound 1 used in crystal form screen.

Figure 35:
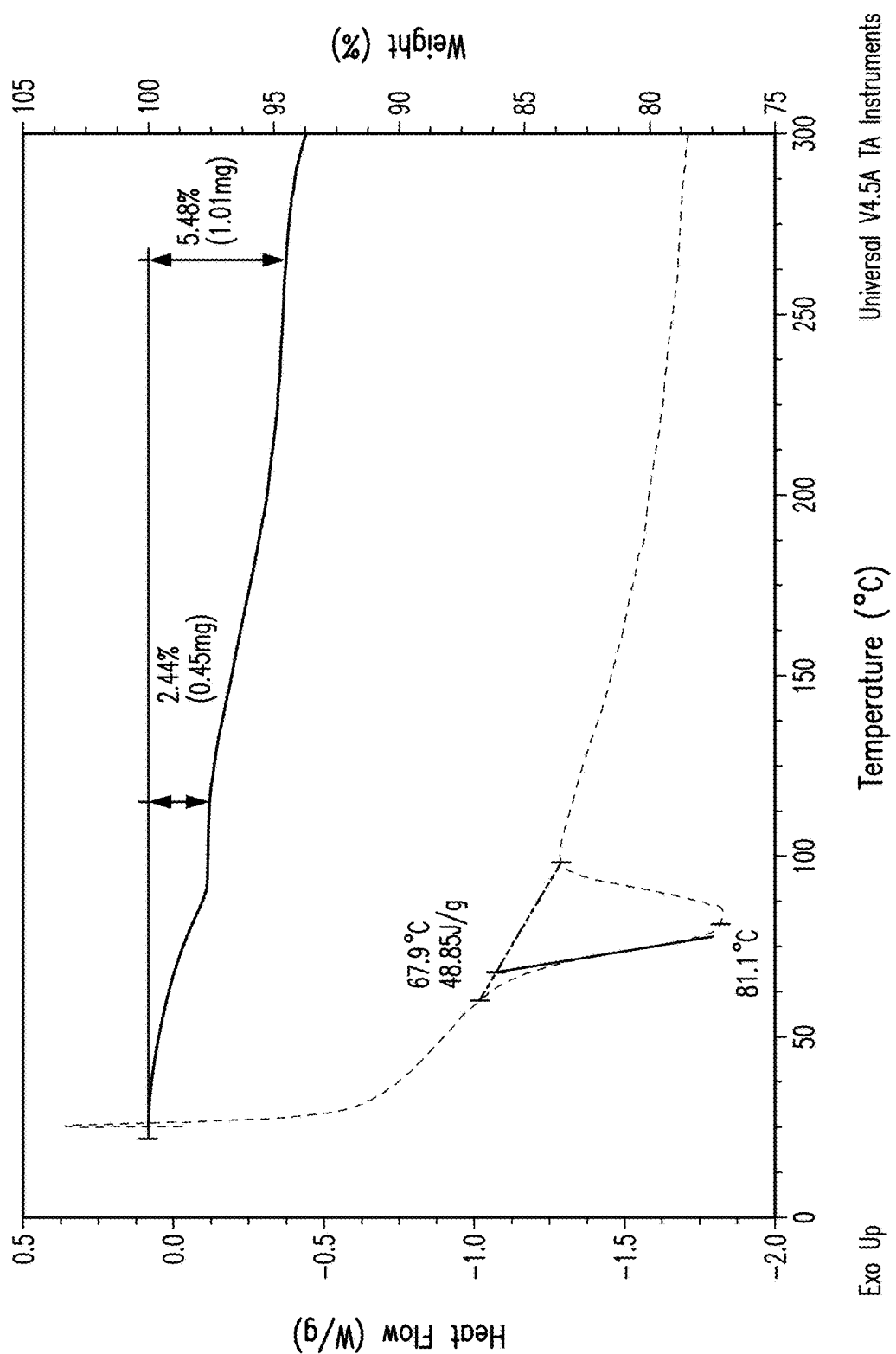

FIG. 35 provides representative DSC and TGA thermograms of the starting material batch of Compound 1 used in crystal form screen.

5. DETAILED DESCRIPTION 5.1 Definitions

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, infrared (IR) or Raman spectroscopy or X-ray powder diffraction (PXRD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), PXRD, single-crystal X-ray diffraction, vibrational spectroscopy, e.g., IR and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of a PXRD peak position may vary by up to ±0.2 degree two theta ($2\theta$) while still describing the particular PXRD peak. In another embodiment, the value of a PXRD peak position may vary by up to ±0.1 degree two theta while still describing the particular PXRD peak.

Unless otherwise specified, the terms "X-ray powder diffraction", "powder X-ray diffraction", "PXRD", and "XRPD" are used interchangeably in this application.

Solid forms may exhibit distinct physical characterization data that are unique to a particular solid form, such as the crystal forms provided herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms provided herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis variation.

As used herein, and unless otherwise specified, a crystalline that is "pure," i.e., substantially free of other crystalline or amorphous solid forms, contains less than about 10% by weight of one or more other crystalline or amorphous solid forms, less than about 5% by weight of one or more other crystalline or amorphous solid forms, less than about 3% by weight of one or more other crystalline or amorphous solid forms, or less than about 1% by weight of one or more other crystalline or amorphous solid forms.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition.

As used herein, and unless otherwise indicated, the term "desolvated solvate" refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

As used herein, and unless otherwise indicated, the term "composition" is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

As used herein, and unless otherwise indicated, the term "solid form" refers to a physical form which is not predominantly in a liquid or a gaseous state. The terms "solid type" and "type" are used interchangeably herein with "solid form". A solid form may be a crystalline form or a mixture thereof. In certain embodiments, a solid form may be a liquid crystal.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23$^{rd}$ ed., 1843-1844 (1995).

As used herein and unless otherwise specified, the term "crystal form" or "crystalline form" refers to a solid form that is crystalline. In certain embodiments, a crystal form of a substance may be substantially free of amorphous solids and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

As used herein and unless otherwise specified, the term "amorphous" or "amorphous solid form" means that the substance, component, or product in question is not substantially crystalline as determined by X-ray diffraction. In particular, the term "amorphous solid" describes a disordered solid form, i.e., a solid form lacking long range crystalline order. In certain embodiments, an amorphous solid form of a substance may be substantially free of other amorphous solid form and/or crystal forms. In certain embodiments, an amorphous solid form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous solid forms and/or crystal forms on a weight basis. In certain embodiments, an amorphous solid form of a substance may be physically and/or chemically pure. In certain embodiments, an amorphous solid form of a substance be about 99%, about 98%, about 97%, about 96%, about 95%, about 94%, about 93%, about 92%, about 91%, or about 90% physically and/or chemically pure.

As used herein, and unless otherwise indicated, the term "tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

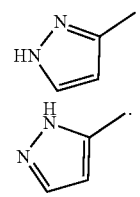

As readily understood by one skilled in the art, a wide variety of functional groups and other structures may exhibit tautomerism.

As used herein, and unless otherwise indicated, the term "zwitterion(s)" means compound(s) containing both a basic moiety, including but not limited to, for example, pyridine and imidazole; and an acidic moiety including but not limited to, for example, a carboxylic acid.

As used herein, the compound "(2Z,5Z)-5-(3-chloro-4-[(2R)-2,3-dihydroxypropoxy]benzylidene)-3-(2-methylphenyl)-2-(propylimino)-1,3-thiazolidin-4-one", the compound "(Z)-5-((Z)-3-chloro-4-((R)-2,3-dihydroxypropoxy)benzylidene)-2-(propylimino)-3-(o-tolyl)thiazolidin-4-one", or Compound 1 has the following structure:

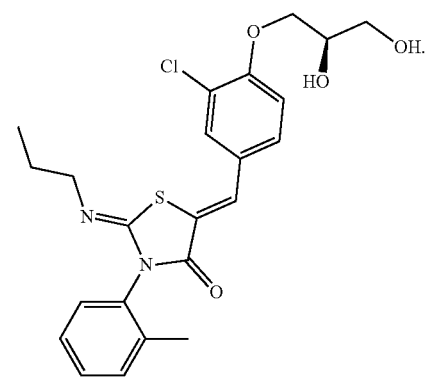 [SMILES: CCC/N=C1\S/C(=C\c2ccc(OC[C@H](O)CO)c(Cl)c2)C(=O)N1c1ccccc1C]

As used herein, and unless otherwise indicated, the term "treating" means an alleviation, in whole or in part, of the disease or disorder, or symptoms associated with the disease or disorder, or slowing, or halting of further progression or worsening of the disease or disorder, or symptoms associated with the disease or disorder.

As used herein, and unless otherwise indicated, the term "preventing" means prevention of the onset, recurrence, or spread of the disease or disorder, or symptoms associated with the disorder or disease, in a patient at risk for developing the disease or disorder.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals. In one embodiment, a subject or patient is a non-human animal, in another embodiment a non-human mammal. In another embodiment, a subject or patient is a human having or at risk for having an autoimmune or chronic inflammatory disease. In certain embodiments, the autoimmune or chronic inflammatory disease is polymyositis, dermatomyositis, lupus nephritis, rheumatoid arthritis, inflammatory bowel disease, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease or multiple sclerosis. In certain embodiments, provided herein are methods for treating a subject suffering from or at risk for having relapsing-remitting multiple sclerosis, primary progressive multiple sclerosis, secondary progressive multiple sclerosis, and relapsing secondary progressive multiple sclerosis. In certain embodiments, a subject or patient is a human having or at risk for having a neurological disorder. In certain embodiments, the neurological disorder is Rett Syndrome. In certain embodiments, a subject or patient is a human having or at risk for having renal or hepatic impairment. In certain embodiments, a subject or patient is a human having or at risk for having a disease or disorder associated with sphingosine 1-phosphate, including but not limited to multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, and Graves' disease. In certain embodiments, a subject or patient is a human having or at risk for having a disease or disorder associated with the interferon alpha receptor 1, including but not limited to psoriasis, ulcerative colitis, systemic lupus, multiple sclerosis, and rheumatoid arthritis. In certain embodiments, a subject or patient is a human having a disease or disorder mediated by lymphocyte interactions, such as, for example, in transplantation, such as acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus.

Unless otherwise specified, to the extent that there is a discrepancy between a depicted chemical structure of a compound provided herein and a chemical name of a compound provided herein, the chemical structure shall control.

5.2 Compound 1

The solid forms, formulations and methods of use provided herein relate to solid forms (e.g., crystalline forms, amorphous forms, polymorphs or mixtures thereof)) comprising Compound 1:

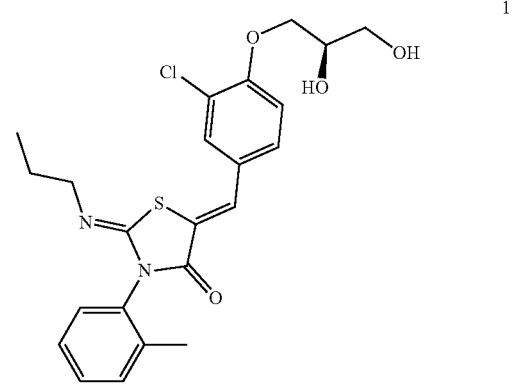 [SMILES: CCC/N=C1\S/C(=C\c2ccc(OC[C@H](O)CO)c(Cl)c2)C(=O)N1c1ccccc1C]

1 having the name (Z)-5-((Z)-3-chloro-4-((R)-2,3-dihydroxypropoxy)benzylidene)-2-(propylimino)-3-(o-tolyl)thiazolidin-4-one. The solid forms provided herein also include solid forms comprising a tautomer of Compound 1. Compound 1 can be prepared by methods known in the art. See, e.g., International Patent Application Publication No. WO 2005/054215.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Forms of Compound 1

In certain embodiments, provided herein are solid forms comprising Compound 1. In certain embodiments, the solid form is crystalline. In certain embodiments, the solid form is a single-component solid form. In certain embodiments, the solid form is a hydrate. In certain embodiments, the solid form is an anhydrate. In certain embodiments, the solid form is a solvate. In certain embodiments, the solid form is non-solvated.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art. While not intending to be bound by any particular theory, certain solid forms provided herein exhibit suitable pharmaceutical properties, e.g., pharmaceutical kinetics, pharmaceutical dynamics, half-life, $C_{max}$, and bioavailability. Such properties can be determined using assays known to the skilled artisan.

The solid forms comprising Compound 1 provided herein (e.g., Form A, Form B, Form C, Form D, Form E, Form F, Form G, Form H, and Form I) may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering or diffraction technique.

The purity of the solid forms provided herein may be determined by standard analytical methods, such as thin layer chromatography (TLC), gel electrophoresis, gas chromatography, high performance liquid chromatography (HPLC), and mass spectrometry.

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ or ±0.1° 2θ (see, United States Pharmacopoeia, page 2228 (2003)).

(a) Methods of Preparing Solid Forms Comprising Compound 1

In certain embodiments, a solid form provided herein is prepared by slurrying Compound 1 in a solvent. In one embodiment, a solid form provided herein is prepared by slurrying Compound 1 in a solvent for a period of time (e.g., about 65 hours) while cycling the temperature (e.g., between about 5° C. and about 40° C.). In certain embodiments, provided herein are methods for making a solid form comprising Compound 1, comprising 1) obtaining a slurry of Compound 1 in a solvent or solvent system; 2) stirring the slurry for a period of time (e.g., about 65 hours) while cycling the temperature (e.g., between about 5° C. and about 40° C.); and 3) collecting solids from the slurry by filtration and optionally drying the collected solids to provide a solid form comprising Compound 1. In certain embodiments, the methods for making a solid form comprising Compound 1 are equilibration experiments, such as slurry experiments. In certain embodiments, the collected solids are dried under vacuum at a certain temperature (e.g., ambient temperature).

In certain embodiments, a solid form provided herein is prepared by slurrying Compound 1 in a solvent though temperature-cycling. In certain embodiments, provided herein are methods for making a solid form comprising Compound 1, comprising 1) obtaining a sample by mixing the solid of Compound 1 with a solvent (e.g., ethanol); 2) stirring the sample for a period of time (e.g., about 60 min) at about 70° C.; 3) ramping the sample from about 70° C. to about 10° C. in about 60 min; 4) holding the sample at about 10° C. for about 180 min; 5) ramping the sample from about 10° C. to about 25° C. in about 60 min; 6) holding the sample at about 25° C. for about 180 min; 7) repeating steps 2) to 6) for two more times; 8) holding the sample at about 25° C. for about 1 day; 9) adding the same solvent to the sample; 10) agitating the sample with a stainless spatula; 11) ramping the sample from about 25° C. to about 70° C. in about 60 min; 12) holding the sample at about 70° C. for about 60 min; 13) ramping the sample from about 70° C. to about 5° C. in about 130 min; 14) holding the sample at about 5° C. for about 180 min; 15) repeating steps 11) to 14) for one more time; 16) holding the sample at about 5° C. for about 1 day; 17) adding Milli-Q water to the sample; 18) agitating the sample with vortex mixer to obtain a free flow suspension; 19) stirring the sample at about 70° C. for about 4 days; 20) isolating the solids through centrifuge tube filter at 5800 RPM for about 20 min; and 21) drying the solids in air for about 4 hours, then drying in vacuum oven at about 45° C. overnight to provide a solid form comprising Compound 1.

In certain embodiments, a solid form provided herein is prepared by rapidly cooling a solution of Compound 1. In one embodiment, a solid form provided herein is prepared by rapidly cooling a saturated solution of Compound 1 from a first temperature (e.g., about 40° C.) to a second temperature (e.g., about 4° C.), and holding at the second temperature for a period of time (e.g., about 6.5 days or about 2 days).

In certain embodiments, a solid form provided herein is prepared by slowly evaporating a solution of Compound 1. In one embodiment, a solid form provided herein is prepared by slowly evaporating a solution of Compound 1 at room temperature for a period of time (e.g., about 11 days). In certain embodiments, provided herein are methods for making a solid form comprising Compound 1, comprising 1) dissolving Compound 1 in a solvent or solvent system to yield a solution; 2) filtering the solution if Compound 1 does not dissolve completely; 3) evaporating the supernatant at a certain temperature (e.g., ambient temperature) over a period of time (e.g., 11 days) to provide a solid form comprising Compound 1.

In certain embodiments, a solid form provided herein is prepared by crystallizing from a solution of Compound 1 in a solvent with the addition of an anti-solvent. In one embodiment, the resulted solution is stirred at room temperature for a period of time (e.g., about 18 hours). In certain embodiments, provided herein are methods for making a solid form comprising Compound 1, comprising 1) obtaining a solution of Compound 1 in a solvent or solvent system at a temperature (e.g., ambient temperature); 2) adding an anti-solvent into the saturated solution at the same temperature; 3) stirring the solution for a period of time (e.g., about 18 hours); 4) cycling the temperature (e.g., between about 40° C. and about 5° C.) for a period of time (e.g., 4 days); 5) isolating the solids to provide a solid form comprising Compound 1.

In certain embodiments, provided herein are methods for making a solid form comprising Compound 1, comprising 1) mixing Compound 1 with a solvent or solvent system; 2) stirring the mixture at a certain temperature for a certain time; 3) filtering the mixture; and 4) drying the resulting solid in a vacuum oven (e.g., at 45° C. overnight) to provide a solid form comprising Compound 1. In certain embodiments, the certain temperature is ambient temperature and the certain time is about one day.

(b) Form A

In certain embodiments, provided herein is Form A of Compound 1.

In one embodiment, Form A is crystalline. In one embodiment, Form A is substantially crystalline. In one embodiment, Form A is moderately crystalline. In one embodiment, Form A is partially crystalline.

In one embodiment, Form A is a solvate of Compound 1. In one embodiment, Form A is an isopropyl acetate solvate of Compound 1. In one embodiment, Form A is an MTBE solvate of Compound 1. In one embodiment, Form A could be isostructural solvates of Compound 1.

A representative XRPD pattern of Form A is provided in FIG. 1.

In one embodiment, provided herein is a solid form comprising Compound 1, characterized by 1, 2, 3, 4, 5, 6, 7, 8, or all of the peaks located at approximately the following positions: 3.2, 4.2, 5.6, 6.3, 10.9, 11.3, 12.3, 13.5, and 22.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by all of the peaks.

In one embodiment, provided herein is a solid form comprising Compound 1, characterized by an XRPD pattern comprising peaks at approximately 3.2, 5.6, and 6.3° 2θ. In one embodiment, the XRPD pattern further comprises peaks at approximately 4.2 and 13.5° 2θ. In one embodiment, the XRPD pattern comprises peaks at approximately 3.2, 4.2, 5.6, 6.3, and 13.5° 2θ, in combination with at least one peak selected from approximately 10.9, 11.3, 12.3, and 22.0° 2θ.

In one embodiment, provided herein is a solid form comprising Compound 1, characterized by an XRPD pattern that matches the XRPD pattern presented in FIG. 1.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form A is provided in FIG. 2. In one embodiment, provided herein is a solid form comprising Compound 1, characterized by an FT-Raman spectrum that matches the FT-Raman spectrum presented in FIG. 2.

Representative differential scanning calorimetry (DSC) and thermal gravimetric analysis (TGA) thermograms of Form A are provided in FIG. 3.

In one embodiment, provided herein is a solid form comprising Compound 1, which exhibits, as characterized by DSC, a thermal event with an onset temperature of about 83° C. In one embodiment, the thermal event also has a peak temperature of about 95° C. In one embodiment, without being limited by any particular theory, the event corresponds to melting and/or desolvation of the solid form. In one embodiment, provided herein is a solid form comprising Compound 1, characterized by a DSC thermogram that matches the DSC thermogram presented in FIG. 3.

In one embodiment, provided herein is a solid form comprising Compound 1, which exhibits a weight loss of about 1.7% upon heating from about 33° C. to about 90° C. In one embodiment, provided herein is a solid form comprising Compound 1, which exhibits a weight loss of about 2.6% upon heating from about 33° C. to about 150° C. In one embodiment, without being limited by any particular theory, the weight loss corresponds to the loss of isopropyl acetate. In one embodiment, provided herein is a solid form comprising Compound 1, characterized by a TGA thermogram that matches the TGA thermogram presented in FIG. 3.

In another embodiment, provided herein is a solid form comprising Compound 1, which exhibits, as characterized by DSC, a thermal event with an onset temperature of about 75° C. In one embodiment, the solid form exhibits a weight loss of about 2.4% upon heating. In one embodiment, without being limited by any particular theory, the weight loss corresponds to the loss of MTBE.

A representative polarized light microscopy (PLM) image of Form A is presented in FIG. 4.

In one embodiment, Form A is prepared by slurrying Compound 1 in a solvent. In one embodiment, Form A is prepared by slurrying Compound 1 in a solvent for a period of time (e.g., about 65 hours) while cycling the temperature (e.g., between about 5° C. and about 40° C.). In one embodiment, provided herein is a process for preparing Form A, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form A of Compound 1. In one embodiment, the solvent is isopropyl acetate, MTBE, hexane, ethyl acetate, or cyclohexane, or a mixture thereof. In one embodiment, the solvent is isopropyl acetate. In one embodiment, the solvent is MTBE. In one embodiment, the solvent is hexane. In one embodiment, the solvent is a mixture of ethyl acetate and cyclohexane (e.g., a 20:80 v/v mixture).

In one embodiment, provided herein is a solid form comprising Form A of Compound 1. In one embodiment, the solid form is substantially free of amorphous Compound 1. In one embodiment, the solid form is substantially free of other crystalline forms of Compound 1. In one embodiment, the solid form is substantially free of Form B, Form C, Form D, Form E, Form F, Form G, Form H, or Form I of Compound 1. In one embodiment, the solid form is substantially free of salts of Compound 1. In one embodiment, the solid form consists essentially of Form A of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form A of Compound 1. In one embodiment, the solid form comprising Form A of Compound 1 is substantially pure.

In one embodiment, provided herein is a solid form comprising Form A of Compound 1 and amorphous Compound 1. In one embodiment, provided herein is a solid form comprising Form A of Compound 1 and one or more other crystalline forms of Compound 1. In one embodiment, provided herein is a solid form comprising Form A of Compound 1 and one or more of Form B, Form C, Form D, Form E, Form F, Form G, Form H, and Form I of Compound 1.

Further properties of the Form A are provided in the Examples section.

All of the combinations of the above embodiments are encompassed by this application.

(c) Form B

In certain embodiments, provided herein is Form B of Compound 1.

In one embodiment, Form B is crystalline. In one embodiment, Form B is substantially crystalline. In one embodiment, Form B is moderately crystalline. In one embodiment, Form B is partially crystalline.

In one embodiment, Form B is a hydrate of Compound 1.

A representative XRPD pattern of Form B is provided in FIG. 5A.

In one embodiment, provided herein is a solid form comprising Compound 1, characterized by 1, 2, 3, 4, 5, 6, 7, or all of the peaks located at approximately the following positions: 6.9, 11.2, 12.5, 16.6, 18.8, 21.3, 23.6, and 25.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by all of the peaks.

In one embodiment, provided herein is a solid form comprising Compound 1, characterized by an XRPD pattern comprising peaks at approximately 6.9, 11.2, and 12.5° 2θ. In one embodiment, the XRPD pattern further comprises peaks at approximately 16.6 and 21.3° 2θ. In one embodiment, the XRPD pattern comprises peaks at approximately 6.9, 11.2, 12.5, 16.6, and 21.3° 2θ, in combination with at least one peak selected from approximately 18.8, 23.6, and 25.9° 2θ.

In one embodiment, provided herein is a solid form comprising Compound 1, characterized by an XRPD pattern that matches the XRPD pattern presented in FIG. 5A.

Another representative XRPD pattern of Form B is provided in FIG. 5B.

In one embodiment, provided herein is a solid form comprising Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 6.3, 6.9, 8.7, 10.3, 11.2, 12.6, 14.9, 16.6, 17.5, 18.9, 19.2, 21.3, 21.9, 22.6, 23.6, 24.5, 24.9, 25.2, 26.0, 27.1, 28.4, 29.2, and 30.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising Compound 1, characterized by an XRPD pattern comprising peaks at approximately 6.9, 11.2, and 12.6° 2θ. In one embodiment, the XRPD pattern further comprises peaks at approximately 16.6 and 18.9° 2θ. In one embodiment, the XRPD pattern comprises peaks at approximately 6.9, 11.2, 12.6, 16.6, and 18.9° 2θ, in combination with at least one peak selected from approximately 14.9, 17.5, 21.3, and 23.6° 2θ.

In one embodiment, provided herein is a solid form comprising Compound 1, characterized by an XRPD pattern that matches the XRPD pattern presented in FIG. 5B.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form B is provided in FIG. 6. In one embodiment, provided herein is a solid form comprising Compound 1, characterized by an FT-Raman spectrum that matches the FT-Raman spectrum presented in FIG. 6.

Representative differential scanning calorimetry (DSC) and thermal gravimetric analysis (TGA) thermograms of Form B are provided in FIG. 7A.

In one embodiment, provided herein is a solid form comprising Compound 1, which exhibits, as characterized by DSC, a first thermal event with an onset temperature of about 50° C., and a second thermal event with an onset temperature of about 93° C. In one embodiment, the first thermal event also has a peak temperature of about 67° C., and the second thermal event also has a peak temperature of about 105° C. In one embodiment, without being limited by any particular theory, the first event corresponds to dehydration of the solid form. In one embodiment, without being limited by any particular theory, the second event corresponds to melting of the dehydrated solid form. In one embodiment, provided herein is a solid form comprising Compound 1, characterized by a DSC thermogram that matches the DSC thermogram presented in FIG. 7A.

In one embodiment, provided herein is a solid form comprising Compound 1, which exhibits a weight loss of about 2.2% upon heating from about 30° C. to about 110° C. In one embodiment, without being limited by any particular theory, the weight loss corresponds to the loss of water. In one embodiment, provided herein is a solid form comprising Compound 1, characterized by a TGA thermogram that matches the TGA thermogram presented in FIG. 7A.

Another representative differential scanning calorimetry (DSC) and thermal gravimetric analysis (TGA) thermograms of Form B are provided in FIG. 7B.

In one embodiment, provided herein is a solid form comprising Compound 1, which exhibits, as characterized by DSC, a first thermal event with a peak temperature of about 58° C., and a second thermal event with an onset temperature of about 105° C. In one embodiment, the second thermal event also has a peak temperature of about 114° C. In one embodiment, provided herein is a solid form comprising Compound 1, characterized by a DSC thermogram that matches the DSC thermogram presented in FIG. 7B.

In one embodiment, provided herein is a solid form comprising Compound 1, which exhibits a weight loss of about 1.8% upon heating from about 28° C. to about 75° C. In one embodiment, without being limited by any particular theory, the weight loss corresponds to the loss of water. In one embodiment, provided herein is a solid form comprising Compound 1, characterized by a TGA thermogram that matches the TGA thermogram presented in FIG. 7B.

Another representative differential scanning calorimetry (DSC) thermogram of Form B is provided in FIG. 7C. In one embodiment, provided herein is a solid form comprising Compound 1, which exhibits, as characterized by DSC, a first thermal event with an onset temperature of about 65° C., and a second thermal event with an onset temperature of about 107° C. In one embodiment, provided herein is a solid form comprising Compound 1, characterized by a DSC thermogram that matches the DSC thermogram presented in FIG. 7C.

A representative polarized light microscopy (PLM) image of Form B is presented in FIG. 8.

In one embodiment, Form B is prepared by slurrying Compound 1 in a solvent. In one embodiment, Form B is prepared by slurrying Compound 1 in a solvent for a period of time (e.g., about 65 hours) while cycling the temperature (e.g., between about 5° C. and about 40° C.). In one embodiment, provided herein is a process for preparing Form B, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form B of Compound 1. In one embodiment, the solvent is water. In one embodiment, the solvent is a mixed solvent containing water. In one embodiment, the solvent is a mixture of N,N-dimethylformamide (DMF) and water (e.g., a 20:80 v/v mixture). In one embodiment, the solvent is a mixture of methanol and water (e.g., a 90:10 v/v mixture). In one embodiment, the solvent is a mixture of acetone and water (e.g., a 80:20 v/v mixture).

In one embodiment, Form B is prepared by rapidly cooling a solution of Compound 1. In one embodiment, Form B is prepared by rapidly cooling a saturated solution of Compound 1 from a first temperature (e.g., about 40° C.) to a second temperature (e.g., about 4° C.), and holding at the second temperature for a period of time (e.g., about 6.5 days). In one embodiment, the solvent is a mixed solvent containing water. In one embodiment, the solvent is a mixture of methanol and water (e.g., a 90:10 v/v mixture). In one embodiment, the solvent is a mixture of 2-propanol and water (e.g., a 90:10 v/v mixture).

In one embodiment, Form B is prepared by slowly evaporating a solution of Compound 1. In one embodiment, Form B is prepared by slowly evaporating a solution of Compound 1 at room temperature for a period of time (e.g., about 11 days). In one embodiment, the solvent is methanol. In one embodiment, the solvent is a mixed solvent containing water. In one embodiment, the solvent is a mixture of acetonitrile and water (e.g., a 90:10 v/v mixture). In one embodiment, the solvent is a mixture of acetone and water (e.g., a 90:10 v/v mixture, or a 80:20 v/v mixture). In one embodiment, the solvent is a mixture of 2-propanol and water (e.g., a 90:10 v/v mixture).

In one embodiment, provided herein is a process for preparing Form B, comprising: 1) obtaining a slurry of Compound 1 in a solvent; 2) stirring the slurry (e.g., at 500 RPM or 600 RPM) at ambient temperature for a period of time (e.g., overnight); and 3) collecting solids from the slurry by filtration (e.g., via centrifuge tube filter) and optionally drying the collected solids to provide Form B of Compound 1. In one embodiment, the solvent is a mixture of ethanol and water (e.g., a 50:50 v/v mixture).

In one embodiment, provided herein is a solid form comprising Form B of Compound 1. In one embodiment, the solid form is substantially free of amorphous Compound 1. In one embodiment, the solid form is substantially free of other crystalline forms of Compound 1. In one embodiment, the solid form is substantially free of Form A, Form C, Form D, Form E, Form F, Form G, Form H, or Form I of Compound 1. In one embodiment, the solid form is substantially free of salts of Compound 1. In one embodiment, the solid form consists essentially of Form B of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form B of Compound 1. In one embodiment, the solid form comprising Form B of Compound 1 is substantially pure.

In one embodiment, provided herein is a solid form comprising Form B of Compound 1 and amorphous Compound 1. In one embodiment, provided herein is a solid form comprising Form B of Compound 1 and one or more other crystalline forms of Compound 1. In one embodiment, provided herein is a solid form comprising Form B of Compound 1 and one or more of Form A, Form C, Form D, Form E, Form F, Form G, Form H, and Form I of Compound 1.

Further properties of the Form B are provided in the Examples section.

All of the combinations of the above embodiments are encompassed by this application.

(d) Form C

In certain embodiments, provided herein is Form C of Compound 1.

In one embodiment, Form C is crystalline. In one embodiment, Form C is substantially crystalline. In one embodiment, Form C is moderately crystalline. In one embodiment, Form C is partially crystalline.

In one embodiment, Form C is a hydrate of Compound 1.

A representative XRPD pattern of Form C is provided in FIG. 9.

In one embodiment, provided herein is a solid form comprising Compound 1, characterized by 1, 2, 3, 4, 5, 6, 7, 8, 9, 10, 11, 12, 13, 14, 15, 16, 17, 18, or all of the peaks located at approximately the following positions: 4.3, 6.4, 6.7, 7.2, 8.7, 10.4, 11.2, 12.9, 13.8, 14.9, 16.4, 16.7, 17.6, 18.9, 21.4, 23.7, 25.8, 27.2, and 28.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising Compound 1, characterized by an XRPD pattern comprising peaks at approximately 4.3, 6.7, and 11.2° 2θ. In one embodiment, the XRPD pattern further comprises peaks at approximately 8.7, 10.4 and 14.9° 2θ. In one embodiment, the XRPD pattern comprises peaks at approximately 4.3, 6.7, 8.7, 10.4, 11.2, and 14.9° 2θ, in combination with at least one peak selected from approximately 6.4, 7.2, 16.7, and 18.9° 2θ.

In one embodiment, provided herein is a solid form comprising Compound 1, characterized by an XRPD pattern comprising peaks at approximately 4.3, 6.7, and 11.2° 2θ. In one embodiment, the XRPD pattern further comprises peaks at approximately 14.9 and 18.9° 2θ. In one embodiment, the XRPD pattern comprises peaks at approximately 4.3, 6.7, 11.2, 14.9, and 18.9° 2θ, in combination with at least one peak selected from approximately 6.4, 7.2, 8.7, 10.4, and 16.7° 2θ.

In one embodiment, provided herein is a solid form comprising Compound 1, characterized by an XRPD pattern comprising peaks at approximately 6.4, 10.4, and 16.7° 2θ.

In one embodiment, the XRPD pattern further comprises peaks at approximately 6.7 and 14.9° 2θ.

In one embodiment, provided herein is a solid form comprising Compound 1, characterized by an XRPD pattern that matches the XRPD pattern presented in FIG. 9.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form C is provided in FIG. 10. In one embodiment, provided herein is a solid form comprising Compound 1, characterized by an FT-Raman spectrum that matches the FT-Raman spectrum presented in FIG. 10.

Representative differential scanning calorimetry (DSC) and thermal gravimetric analysis (TGA) thermograms of Form C are provided in FIG. 11.

In one embodiment, provided herein is a solid form comprising Compound 1, which exhibits, as characterized by DSC, a first thermal event with an onset temperature of about 69° C., and a second thermal event with an onset temperature of about 107° C. In one embodiment, the first thermal event also has a peak temperature of about 72° C., and the second thermal event also has a peak temperature of about 117° C. In one embodiment, without being limited by any particular theory, the first event corresponds to dehydration of the solid form. In one embodiment, without being limited by any particular theory, the second event corresponds to melting of the solid form. In one embodiment, provided herein is a solid form comprising Compound 1, characterized by a DSC thermogram that matches the DSC thermogram presented in FIG. 11.

In one embodiment, provided herein is a solid form comprising Compound 1, which exhibits a weight loss of about 2.1% upon heating from about 36° C. to about 150° C. In one embodiment, without being limited by any particular theory, the weight loss corresponds to the loss of water and trace amount of dichloromethane. In one embodiment, provided herein is a solid form comprising Compound 1, characterized by a TGA thermogram that matches the TGA thermogram presented in FIG. 11.

In another embodiment, provided herein is a solid form comprising Compound 1, which exhibits a weight loss of about 0.7% upon heating. In one embodiment, without being limited by any particular theory, the weight loss corresponds to the loss of water.

A representative polarized light microscopy (PLM) image of Form C is presented in FIG. 12.

In one embodiment, Form C is prepared by slurrying Compound 1 in a solvent. In one embodiment, Form C is prepared by slurrying Compound 1 in a solvent for a period of time (e.g., about 65 hours) while cycling the temperature (e.g., between about 5° C. and about 40° C.). In one embodiment, provided herein is a process for preparing Form C, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form C of Compound 1. In one embodiment, the solvent is methanol. In one embodiment, the solvent is dichloromethane.

In one embodiment, Form C is prepared by rapidly cooling a solution of Compound 1. In one embodiment, Form C is prepared by rapidly cooling a saturated solution of Compound 1 from a first temperature (e.g., about 40° C.) to a second temperature (e.g., about 4° C.), and holding at the second temperature for a period of time (e.g., about 2 days, or about 6.5 days). In one embodiment, the solvent is acetonitrile. In one embodiment, the solvent is dichloromethane.

In one embodiment, provided herein is a solid form comprising Form C of Compound 1. In one embodiment, the solid form is substantially free of amorphous Compound 1. In one embodiment, the solid form is substantially free of other crystalline forms of Compound 1. In one embodiment, the solid form is substantially free of Form A, Form B, Form D, Form E, Form F, Form G, Form H, or Form I of Compound 1. In one embodiment, the solid form is substantially free of salts of Compound 1. In one embodiment, the solid form consists essentially of Form C of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form C of Compound 1. In one embodiment, the solid form comprising Form C of Compound 1 is substantially pure.

In one embodiment, provided herein is a solid form comprising Form C of Compound 1 and amorphous Compound 1. In one embodiment, provided herein is a solid form comprising Form C of Compound 1 and one or more other crystalline forms of Compound 1. In one embodiment, provided herein is a solid form comprising Form C of Compound 1 and one or more of Form A, Form B, Form D, Form E, Form F, Form G, Form H, and Form I of Compound 1.

Further properties of the Form C are provided in the Examples section.

All of the combinations of the above embodiments are encompassed by this application.

(e) Form D

In certain embodiments, provided herein is Form D of Compound 1.

In one embodiment, Form D is crystalline. In one embodiment, Form D is substantially crystalline. In one embodiment, Form D is moderately crystalline. In one embodiment, Form D is partially crystalline.

In one embodiment, Form D is a solvate of Compound 1. In one embodiment, Form D is a hydrate of Compound 1. In one embodiment, Form D is a cyclohexane solvate of Compound 1. In one embodiment, Form D is a 2-propanol solvate of Compound 1. In one embodiment, Form D is a water and cyclohexane mixed solvate of Compound 1. In one embodiment, Form D is a water and 2-propanol mixed solvate of Compound 1. In one embodiment, Form D could be isostructural solvates of Compound 1.

A representative XRPD pattern of Form D is provided in FIG. 13.

In one embodiment, provided herein is a solid form comprising Compound 1, characterized by 1, 2, 3, 4, 5, 6, 7, 8, 9, 10, 11, 12, 13, 14, 15, 16, 17, 18, 19, or all of the peaks located at approximately the following positions: 4.0, 4.6, 6.9, 7.5, 11.1, 11.8, 12.9, 15.0, 16.6, 18.5, 19.6, 20.4, 21.4, 22.4, 23.5, 24.1, 25.2, 25.9, 26.7, and 28.3° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising Compound 1, characterized by an XRPD pattern comprising peaks at approximately 4.0, 4.6, and 6.9° 2θ. In one embodiment, the XRPD pattern further comprises peaks at approximately 11.1, 11.8, and 18.5° 2θ. In one embodiment, the XRPD pattern comprises peaks at approximately 4.0, 4.6, 6.9, 11.1, 11.8, and 18.5° 2θ, in combination with at least one peak selected from approximately 7.5, 15.0, 16.6, and 23.5° 2θ.

In one embodiment, provided herein is a solid form comprising Compound 1, characterized by an XRPD pattern comprising peaks at approximately 4.6, 11.8, and 18.5° 2θ. In one embodiment, the XRPD pattern further comprises peaks at approximately 7.5 and 16.6° 2θ. In one embodiment, the XRPD pattern comprises peaks at approximately 4.6, 7.5, 11.8, 16.6, and 18.5° 2θ, in combination with at least one peak selected from approximately 4.0, 6.9, 11.1, 15.0, and 23.5° 2θ.

In one embodiment, provided herein is a solid form comprising Compound 1, characterized by an XRPD pattern that matches the XRPD pattern presented in FIG. 13.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form D is provided in FIG. 14. In one embodiment, provided herein is a solid form comprising Compound 1, characterized by an FT-Raman spectrum that matches the FT-Raman spectrum presented in FIG. 14.

Representative differential scanning calorimetry (DSC) and thermal gravimetric analysis (TGA) thermograms of Form D are provided in FIG. 15.

In one embodiment, provided herein is a solid form comprising Compound 1, which exhibits, as characterized by DSC, a thermal event with an onset temperature of about 85° C. In one embodiment, the thermal event also has a peak temperature of about 94° C. In one embodiment, without being limited by any particular theory, the event corresponds to melting and/or desolvation of the solid form. In one embodiment, provided herein is a solid form comprising Compound 1, characterized by a DSC thermogram that matches the DSC thermogram presented in FIG. 15.

In one embodiment, provided herein is a solid form comprising Compound 1, which exhibits a weight loss of about 5.2% upon heating from about 29° C. to about 102° C., and a weight loss of about 3.6% upon heating from about 102° C. to about 181° C. In one embodiment, without being limited by any particular theory, the weight losses correspond to the losses of water and cyclohexane. In one embodiment, provided herein is a solid form comprising Compound 1, characterized by a TGA thermogram that matches the TGA thermogram presented in FIG. 15.

In another embodiment, provided herein is a solid form comprising Compound 1, which exhibits, as characterized by DSC, a thermal event with an onset temperature of about 82° C. In one embodiment, the solid form exhibits a weight loss of about 3.0% upon heating. In one embodiment, without being limited by any particular theory, the weight loss corresponds to the loss of water and 2-propanol.

A representative polarized light microscopy (PLM) image of Form D is presented in FIG. 16.

In one embodiment, Form D is prepared by slurrying Compound 1 in a solvent. In one embodiment, Form D is prepared by slurrying Compound 1 in a solvent for a period of time (e.g., about 65 hours) while cycling the temperature (e.g., between about 5° C. and about 40° C.). In one embodiment, provided herein is a process for preparing Form D, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form D of Compound 1. In one embodiment, the solvent is 1-propanol, 2-propanol, ethanol, cyclohexane, or water, or a mixture thereof. In one embodiment, the solvent is 1-propanol. In one embodiment, the solvent is 2-propanol. In one embodiment, the solvent is a mixture of 2-propanol and cyclohexane (e.g., a 20:80 v/v mixture). In one embodiment, the solvent is a mixture of ethanol and water (e.g., a 20:80 v/v mixture).

In one embodiment, Form D is prepared by slowly evaporating a solution of Compound 1. In one embodiment, Form D is prepared by slowly evaporating a solution of Compound 1 at room temperature for a period of time (e.g., about 11 days). In one embodiment, the solvent is 2-propanol.

In one embodiment, provided herein is a solid form comprising Form D of Compound 1. In one embodiment, the solid form is substantially free of amorphous Compound 1. In one embodiment, the solid form is substantially free of other crystalline forms of Compound 1. In one embodiment, the solid form is substantially free of Form A, Form B, Form C, Form E, Form F, Form G, Form H, or Form I of Compound 1. In one embodiment, the solid form is substantially free of salts of Compound 1. In one embodiment, the solid form consists essentially of Form D of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form D of Compound 1. In one embodiment, the solid form comprising Form D of Compound 1 is substantially pure.

In one embodiment, provided herein is a solid form comprising Form D of Compound 1 and amorphous Compound 1. In one embodiment, provided herein is a solid form comprising Form D of Compound 1 and one or more other crystalline forms of Compound 1. In one embodiment, provided herein is a solid form comprising Form D of Compound 1 and one or more of Form A, Form B, Form C, Form E, Form F, Form G, Form H, and Form I of Compound 1.

Further properties of the Form D are provided in the Examples section.

All of the combinations of the above embodiments are encompassed by this application.

(f) Form E

In certain embodiments, provided herein is Form E of Compound 1.

In one embodiment, Form E is crystalline. In one embodiment, Form E is substantially crystalline. In one embodiment, Form E is moderately crystalline. In one embodiment, Form E is partially crystalline.

In one embodiment, Form E is a non-solvated form of Compound 1.

A representative XRPD pattern of Form E is provided in FIG. 17.

In one embodiment, provided herein is a solid form comprising Compound 1, characterized by 1, 2, 3, 4, 5, 6, 7, 8, 9, 10, 11, 12, 13, 14, 15, 16, 17, 18, or all of the peaks located at approximately the following positions: 5.2, 8.5, 10.5, 12.3, 12.8, 13.8, 16.9, 17.5, 20.8, 21.2, 21.8, 22.9, 23.5, 25.1, 25.7, 27.0, 28.7, 33.0, and 35.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising Compound 1, characterized by an XRPD pattern comprising peaks at approximately 8.5, 12.3, and 16.9° 2θ. In one embodiment, the XRPD pattern further comprises peaks at approximately 5.2, 10.5, and 22.9° 2θ. In one embodiment, the XRPD pattern comprises peaks at approximately 5.2, 8.5, 10.5, 12.3, 16.9, and 22.9° 2θ, in combination with at least one peak selected from approximately 13.8, 17.5, 21.2, and 23.5° 2θ.

In one embodiment, provided herein is a solid form comprising Compound 1, characterized by an XRPD pattern comprising peaks at approximately 5.2, 10.5, and 22.9° 2θ. In one embodiment, the XRPD pattern further comprises peaks at approximately 12.3 and 16.9° 2θ. In one embodiment, the XRPD pattern comprises peaks at approximately 5.2, 10.5, 12.3, 16.9, and 22.9° 2θ, in combination with at least one peak selected from approximately 8.5, 13.8, 17.5, 21.2, and 23.5° 2θ.

In one embodiment, provided herein is a solid form comprising Compound 1, characterized by an XRPD pattern that matches the XRPD pattern presented in FIG. 17.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form E is provided in FIG. 18. In one embodiment, provided herein is a solid form comprising Compound 1, characterized by an FT-Raman spectrum that matches the FT-Raman spectrum presented in FIG. 18.

Representative differential scanning calorimetry (DSC) and thermal gravimetric analysis (TGA) thermograms of Form E are provided in FIG. 19.

In one embodiment, provided herein is a solid form comprising Compound 1, which exhibits, as characterized by DSC, a thermal event with an onset temperature of about 83° C. In one embodiment, the thermal event also has a peak temperature of about 91° C. In one embodiment, without being limited by any particular theory, the event corresponds to melting of the solid form. In one embodiment, provided herein is a solid form comprising Compound 1, characterized by a DSC thermogram that matches the DSC thermogram presented in FIG. 19.

In one embodiment, provided herein is a solid form comprising Compound 1, which exhibits a weight loss of about 0.4% upon heating from about 32° C. to about 110° C. In one embodiment, without being limited by any particular theory, the weight loss corresponds to the loss of trace amount of 1-butanol. In one embodiment, provided herein is a solid form comprising Compound 1, characterized by a TGA thermogram that matches the TGA thermogram presented in FIG. 19.

In another embodiment, provided herein is a solid form comprising Compound 1, which exhibits, as characterized by DSC, a first thermal event with an onset temperature of about 89° C., and a second thermal event with an onset temperature of about 106° C. In one embodiment, the solid form exhibits a weight loss of about 0.8% upon heating. In one embodiment, without being limited by any particular theory, the weight loss corresponds to the loss of trace amount of isopropyl ethyl ether.

A representative polarized light microscopy (PLM) image of Form E is presented in FIG. 20.

In one embodiment, Form E is prepared by slurrying Compound 1 in a solvent. In one embodiment, Form E is prepared by slurrying Compound 1 in a solvent for a period of time (e.g., about 65 hours) while cycling the temperature (e.g., between about 5° C. and about 40° C.). In one embodiment, provided herein is a process for preparing Form E, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form E of Compound 1. In one embodiment, the solvent is nitromethane, 4-methyl-2-pentanone, 1-butanol, acetonitrile, or isopropyl ethyl ether, or a mixture thereof. In one embodiment, the solvent is nitromethane. In one embodiment, the solvent is 4-methyl-2-pentanone. In one embodiment, the solvent is 1-butanol. In one embodiment, the solvent is a mixture of acetonitrile and isopropyl ethyl ether (e.g., a 20:80 v/v mixture).

In one embodiment, Form E is prepared by rapidly cooling a solution of Compound 1. In one embodiment, Form E is prepared by rapidly cooling a saturated solution of Compound 1 from a first temperature (e.g., about 40° C.) to a second temperature (e.g., about 4° C.), and holding at the second temperature for a period of time (e.g., about 6.5 days). In one embodiment, the solvent is anisole, ethanol, or water, or a mixture thereof. In one embodiment, the solvent is anisole. In one embodiment, the solvent is a mixture of ethanol and water (e.g., a 20:80 v/v mixture).

In one embodiment, Form E is prepared by slowly evaporating a solution of Compound 1. In one embodiment, Form E is prepared by slowly evaporating a solution of Compound 1 at room temperature for a period of time (e.g., about 11 days). In one embodiment, the solvent is isopropyl acetate.

In one embodiment, provided herein is a solid form comprising Form E of Compound 1. In one embodiment, the solid form is substantially free of amorphous Compound 1. In one embodiment, the solid form is substantially free of other crystalline forms of Compound 1. In one embodiment, the solid form is substantially free of Form A, Form B, Form C, Form D, Form F, Form G, Form H, or Form I of Compound 1. In one embodiment, the solid form is substantially free of salts of Compound 1. In one embodiment, the solid form consists essentially of Form E of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form E of Compound 1. In one embodiment, the solid form comprising Form E of Compound 1 is substantially pure.

In one embodiment, provided herein is a solid form comprising Form E of Compound 1 and amorphous Compound 1. In one embodiment, provided herein is a solid form comprising Form E of Compound 1 and one or more other crystalline forms of Compound 1. In one embodiment, provided herein is a solid form comprising Form E of Compound 1 and one or more of Form A, Form B, Form C, Form D, Form F, Form G, Form H, and Form I of Compound 1.

Further properties of the Form E are provided in the Examples section.

All of the combinations of the above embodiments are encompassed by this application.

(g) Form F

In certain embodiments, provided herein is Form F of Compound 1.

In one embodiment, Form F is crystalline. In one embodiment, Form F is substantially crystalline. In one embodiment, Form F is moderately crystalline. In one embodiment, Form F is partially crystalline.

In one embodiment, Form F is a solvate of Compound 1. In one embodiment, Form F is a toluene solvate of Compound 1. In one embodiment, Form F could be isostructural solvates of Compound 1.

A representative XRPD pattern of Form F is provided in FIG. 21.

In one embodiment, provided herein is a solid form comprising Compound 1, characterized by 1, 2, 3, 4, 5, 6, 7, or all of the peaks located at approximately the following positions: 3.8, 5.4, 6.1, 7.0, 10.2, 10.8, 13.6, and 14.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by all of the peaks.

In one embodiment, provided herein is a solid form comprising Compound 1, characterized by an XRPD pattern comprising peaks at approximately 3.8, 6.1, and 13.6° 2θ. In one embodiment, the XRPD pattern further comprises peaks at approximately 7.0 and 14.6° 2θ. In one embodiment, the XRPD pattern comprises peaks at approximately 3.8, 6.1, 7.0, 13.6, and 14.6° 2θ, in combination with at least one peak selected from approximately 5.4, 10.2, and 10.8° 2θ.

In one embodiment, provided herein is a solid form comprising Compound 1, characterized by an XRPD pattern comprising peaks at approximately 3.8, 6.1, and 7.0° 2θ. In one embodiment, the XRPD pattern further comprises peaks at approximately 10.2 and 10.8° 2θ. In one embodiment, the XRPD pattern comprises peaks at approximately 3.8, 6.1, 7.0, 10.2, and 10.8° 2θ, in combination with at least one peak selected from approximately 5.4, 13.6, and 14.6° 2θ.

In one embodiment, provided herein is a solid form comprising Compound 1, characterized by an XRPD pattern that matches the XRPD pattern presented in FIG. 21.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form F is provided in FIG. 22. In one embodiment, provided herein is a solid form comprising Compound 1, characterized by an FT-Raman spectrum that matches the FT-Raman spectrum presented in FIG. 22.

Representative differential scanning calorimetry (DSC) and thermal gravimetric analysis (TGA) thermograms of Form F are provided in FIG. 23.

In one embodiment, provided herein is a solid form comprising Compound 1, which exhibits, as characterized by DSC, a thermal event with an onset temperature of about 86° C. In one embodiment, the thermal event also has a peak temperature of about 98° C. In one embodiment, without being limited by any particular theory, the event corresponds to melting and/or desolvation of the solid form. In one embodiment, provided herein is a solid form comprising Compound 1, characterized by a DSC thermogram that matches the DSC thermogram presented in FIG. 23.

In one embodiment, provided herein is a solid form comprising Compound 1, which exhibits a weight loss of about 1.1% upon heating from about 34° C. to about 125° C. In one embodiment, without being limited by any particular theory, the weight loss corresponds to the loss of toluene. In one embodiment, provided herein is a solid form comprising Compound 1, characterized by a TGA thermogram that matches the TGA thermogram presented in FIG. 23.

A representative polarized light microscopy (PLM) image of Form F is presented in FIG. 24.

In one embodiment, Form F is prepared by slurrying Compound 1 in a solvent. In one embodiment, Form F is prepared by slurrying Compound 1 in a solvent for a period of time (e.g., about 65 hours) while cycling the temperature (e.g., between about 5° C. and about 40° C.). In one embodiment, provided herein is a process for preparing Form F, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form F of Compound 1. In one embodiment, the solvent is 2-methoxyethanol, isopropyl ether, methyl acetate, heptane, ethyl acetate, chlorobenzene, cyclohexane, toluene, 1-methoxy-2-propanol, anisole, cumene, or 4-methyl-2-pentanone, or a mixture thereof. In one embodiment, the solvent is a mixture of 2-methoxyethanol and isopropyl ether (e.g., a 20:80 v/v mixture). In one embodiment, the solvent is a mixture of methyl acetate and heptane (e.g., a 20:80 v/v mixture). In one embodiment, the solvent is ethyl acetate. In one embodiment, the solvent is a mixture of chlorobenzene and cyclohexane (e.g., a 20:80 v/v mixture). In one embodiment, the solvent is toluene. In one embodiment, the solvent is a mixture of 1-methoxy-2-propanol and isopropyl ether (e.g., a 20:80 v/v mixture). In one embodiment, the solvent is anisole. In one embodiment, the solvent is cumene. In one embodiment, the solvent is a mixture of 4-methyl-2-pentanone and heptane (e.g., a 20:80 v/v mixture).

In one embodiment, provided herein is a solid form comprising Form F of Compound 1. In one embodiment, the solid form is substantially free of amorphous Compound 1. In one embodiment, the solid form is substantially free of other crystalline forms of Compound 1. In one embodiment, the solid form is substantially free of Form A, Form B, Form C, Form D, Form E, Form G, Form H, or Form I of Compound 1. In one embodiment, the solid form is substantially free of salts of Compound 1. In one embodiment, the solid form consists essentially of Form F of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form F of Compound 1. In one embodiment, the solid form comprising Form F of Compound 1 is substantially pure.

In one embodiment, provided herein is a solid form comprising Form F of Compound 1 and amorphous Compound 1. In one embodiment, provided herein is a solid form comprising Form F of Compound 1 and one or more other crystalline forms of Compound 1. In one embodiment, provided herein is a solid form comprising Form F of Compound 1 and one or more of Form A, Form B, Form C, Form D, Form E, Form G, Form H, and Form I of Compound 1.

Further properties of the Form F are provided in the Examples section.

All of the combinations of the above embodiments are encompassed by this application.

(h) Form G

In certain embodiments, provided herein is Form G of Compound 1.

In one embodiment, Form G is crystalline. In one embodiment, Form G is substantially crystalline. In one embodiment, Form G is moderately crystalline. In one embodiment, Form G is partially crystalline.

In one embodiment, Form G is a solvate of Compound 1. In one embodiment, Form G is a 1-butanol solvate of Compound 1.

A representative XRPD pattern of Form G is provided in FIG. 25.

In one embodiment, provided herein is a solid form comprising Compound 1, characterized by 1, 2, 3, 4, 5, 6, or all of the peaks located at approximately the following positions: 4.5, 6.4, 7.3, 10.4, 13.3, and 22.4° 2θ. In one embodiment, the solid form is characterized by 3 of the peaks. In one embodiment, the solid form is characterized by 5 of the peaks. In one embodiment, the solid form is characterized by all of the peaks.

In one embodiment, provided herein is a solid form comprising Compound 1, characterized by an XRPD pattern comprising peaks at approximately 4.5, 6.4, and 10.4° 2θ. In one embodiment, the XRPD pattern further comprises peaks at approximately 7.3 and 22.4° 2θ. In one embodiment, the XRPD pattern comprises peaks at approximately 4.5, 6.4, 7.3, 10.4, 13.3, and 22.4° 2θ.

In one embodiment, provided herein is a solid form comprising Compound 1, characterized by an XRPD pattern comprising peaks at approximately 6.4, 10.4, and 22.4° 2θ. In one embodiment, the XRPD pattern further comprises peaks at approximately 4.5 and 7.3° 2θ.

In one embodiment, provided herein is a solid form comprising Compound 1, characterized by an XRPD pattern that matches the XRPD pattern presented in FIG. 25.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form G is provided in FIG. 26. In one embodiment, provided herein is a solid form comprising Compound 1, characterized by an FT-Raman spectrum that matches the FT-Raman spectrum presented in FIG. 26.

Representative differential scanning calorimetry (DSC) and thermal gravimetric analysis (TGA) thermograms of Form G are provided in FIG. 27.

In one embodiment, provided herein is a solid form comprising Compound 1, which exhibits, as characterized by DSC, a first thermal event with an onset temperature of about 54° C., and a second thermal event with an onset temperature of about 85° C. In one embodiment, the first thermal event also has a peak temperature of about 66° C., and the second thermal event also has a peak temperature of about 95° C. In one embodiment, without being limited by any particular theory, the first event corresponds to melting of the solid form. In one embodiment, provided herein is a solid form comprising Compound 1, characterized by a DSC thermogram that matches the DSC thermogram presented in FIG. 27.

In one embodiment, provided herein is a solid form comprising Compound 1, which exhibits a weight loss of about 2.5% upon heating from about 31° C. to about 100° C. In one embodiment, without being limited by any particular theory, the weight loss corresponds to the loss of 1-butanol. In one embodiment, provided herein is a solid form comprising Compound 1, characterized by a TGA thermogram that matches the TGA thermogram presented in FIG. 27.

A representative polarized light microscopy (PLM) image of Form G is presented in FIG. 28.

In one embodiment, Form G is prepared by rapidly cooling a solution of Compound 1. In one embodiment, Form G is prepared by rapidly cooling a saturated solution of Compound 1 from a first temperature (e.g., about 40° C.) to a second temperature (e.g., about 4° C.), and holding at the second temperature for a period of time (e.g., about 6.5 days). In one embodiment, the solvent is 1-butanol.

In one embodiment, provided herein is a solid form comprising Form G of Compound 1. In one embodiment, the solid form is substantially free of amorphous Compound 1. In one embodiment, the solid form is substantially free of other crystalline forms of Compound 1. In one embodiment, the solid form is substantially free of Form A, Form B, Form C, Form D, Form E, Form F, Form H, or Form I of Compound 1. In one embodiment, the solid form is substantially free of salts of Compound 1. In one embodiment, the solid form consists essentially of Form G of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form G of Compound 1. In one embodiment, the solid form comprising Form G of Compound 1 is substantially pure.

In one embodiment, provided herein is a solid form comprising Form G of Compound 1 and amorphous Compound 1. In one embodiment, provided herein is a solid form comprising Form G of Compound 1 and one or more other crystalline forms of Compound 1. In one embodiment, provided herein is a solid form comprising Form G of Compound 1 and one or more of Form A, Form B, Form C, Form D, Form E, Form F, Form H, and Form I of Compound 1.

Further properties of the Form G are provided in the Examples section.

All of the combinations of the above embodiments are encompassed by this application.

(i) Form H

In certain embodiments, provided herein is Form H of Compound 1.

In one embodiment, Form H is crystalline. In one embodiment, Form H is substantially crystalline. In one embodiment, Form H is moderately crystalline. In one embodiment, Form H is partially crystalline.

In one embodiment, Form H is a non-solvated form of Compound 1.

A representative XRPD pattern of Form H is provided in FIG. 29.

In one embodiment, provided herein is a solid form comprising Compound 1, characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 10.5, 11.1, 11.4, 11.7, 12.8, 13.6, 13.9, 16.4, 17.3, 18.0, 19.0, 20.9, 22.3, 23.5, 24.1, 25.8, 27.4, 27.8, 28.8, 29.3, 29.7, 30.7, 31.8, and 33.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising Compound 1, characterized by an XRPD pattern comprising peaks at approximately 10.5, 20.9, and 22.3° 2θ. In one embodiment, the XRPD pattern further comprises peaks at approximately 11.1, 13.6, and 23.5° 2θ. In one embodiment, the XRPD pattern comprises peaks at approximately 10.5, 11.1, 13.6, 20.9, 22.3, and 23.5° 2θ, in combination with at least one peak selected from approximately 11.4, 13.9, 16.4, and 25.8° 2θ.

In one embodiment, provided herein is a solid form comprising Compound 1, characterized by an XRPD pattern comprising peaks at approximately 10.5, 11.7, 20.9, and 22.3° 2θ. In one embodiment, the XRPD pattern further comprises peaks at approximately 11.1, 13.6, and 23.5° 2θ. In one embodiment, the XRPD pattern comprises peaks at approximately 10.5, 11.1, 11.7, 13.6, 20.9, 22.3, and 23.5° 2θ, in combination with at least one peak selected from approximately 11.4, 13.9, 16.4, and 25.8° 2θ.

In one embodiment, provided herein is a solid form comprising Compound 1, characterized by an XRPD pattern comprising peaks at approximately 10.5, 12.8, 20.9, and 22.3° 2θ. In one embodiment, the XRPD pattern further comprises peaks at approximately 11.1, 13.6, and 23.5° 2θ. In one embodiment, the XRPD pattern comprises peaks at approximately 10.5, 11.1, 12.8, 13.6, 20.9, 22.3, and 23.5° 2θ, in combination with at least one peak selected from approximately 11.4, 13.9, 16.4, and 25.8° 2θ.

In one embodiment, provided herein is a solid form comprising Compound 1, characterized by an XRPD pattern comprising peaks at approximately 10.5, 17.3, 20.9, and 22.3° 2θ. In one embodiment, the XRPD pattern further comprises peaks at approximately 11.1, 13.6, and 23.5° 2θ. In one embodiment, the XRPD pattern comprises peaks at approximately 10.5, 11.1, 13.6, 17.3, 20.9, 22.3, and 23.5° 2θ, in combination with at least one peak selected from approximately 11.4, 13.9, 16.4, and 25.8° 2θ.

In one embodiment, provided herein is a solid form comprising Compound 1, characterized by an XRPD pattern comprising peaks at approximately 11.7, 12.8, and 17.3° 2θ. In one embodiment, the XRPD pattern further comprises peaks at approximately 10.5, 20.9, and 22.3° 2θ. In one embodiment, the XRPD pattern further comprises peaks at approximately 11.1, 13.6, and 23.5° 2θ.

In one embodiment, provided herein is a solid form comprising Compound 1, characterized by an XRPD pattern that matches the XRPD pattern presented in FIG. 29.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

A representative FT-Raman spectrum of Form H is provided in FIG. 30. In one embodiment, provided herein is a solid form comprising Compound 1, characterized by an FT-Raman spectrum that matches the FT-Raman spectrum presented in FIG. 30.

Representative differential scanning calorimetry (DSC) and thermal gravimetric analysis (TGA) thermograms of Form H are provided in FIG. 31.

In one embodiment, provided herein is a solid form comprising Compound 1, which exhibits, as characterized by DSC, a thermal event with an onset temperature of about 128° C. In one embodiment, the thermal event also has a peak temperature of about 132° C. In one embodiment, without being limited by any particular theory, the event corresponds to melting of the solid form. In one embodiment, provided herein is a solid form comprising Compound 1, characterized by a DSC thermogram that matches the DSC thermogram presented in FIG. 31.

In one embodiment, provided herein is a solid form comprising Compound 1, which exhibits a weight loss of about 0.1% upon heating from about 33° C. to about 113° C. In one embodiment, provided herein is a solid form comprising Compound 1, characterized by a TGA thermogram that matches the TGA thermogram presented in FIG. 31.

A representative polarized light microscopy (PLM) image of Form H is presented in FIG. 32.

In one embodiment, Form H is prepared by slurrying Compound 1 in a solvent. In one embodiment, Form H is prepared by slurrying Compound 1 in a solvent for a period of time (e.g., about 65 hours) while cycling the temperature (e.g., between about 5° C. and about 40° C.). In one embodiment, provided herein is a process for preparing Form H, comprising: 1) obtaining a slurry of Compound 1 in a solvent; 2) stirring the slurry for a period of time (e.g., about 65 hours) while cycling the temperature (e.g., between about 5° C. and about 40° C.); and 3) collecting solids from the slurry by filtration and optionally drying the collected solids to provide Form H of Compound 1. In one embodiment, the solvent is a mixture of acetonitrile and isopropyl ethyl ether (e.g., a 20:80 v/v mixture).

In one embodiment, Form H is prepared by slurrying Compound 1 in a solvent though temperature-cycling. In one embodiment, provided herein is a method for preparing Form H, comprising 1) obtaining a sample by mixing the solid of Compound 1 with a solvent (e.g., ethanol); 2) stirring the sample for a period of time (e.g., about 60 min) at about 70° C.; 3) ramping the sample from about 70° C. to about 10° C. in about 60 min; 4) holding the sample at about 10° C. for about 180 min; 5) ramping the sample from about 10° C. to about 25° C. in about 60 min; 6) holding the sample at about 25° C. for about 180 min; 7) repeating steps 2) to 6) for two more times; 8) holding the sample at about 25° C. for about 1 day; 9) adding the same solvent to the sample; 10) agitating the sample with a stainless spatula; 11) ramping the sample from about 25° C. to about 70° C. in about 60 min; 12) holding the sample at about 70° C. for about 60 min; 13) ramping the sample from about 70° C. to about 5° C. in about 130 min; 14) holding the sample at about 5° C. for about 180 min; 15) repeating steps 11) to 14) for one more time; 16) holding the sample at about 5° C. for about 1 day; 17) adding Milli-Q water to the sample; 18) agitating the sample with vortex mixer to obtain a free flow suspension; 19) stirring the sample at about 70° C. for about 4 days; 20) isolating the solids through centrifuge tube filter at 5800 RPM for about 20 min; and 21) drying the solids in air for about 4 hours, then drying in vacuum oven at about 45° C. overnight to provide a solid form comprising Compound 1.

In one embodiment, Form H is prepared by crystallizing a solution of Compound 1 in a solvent with the addition of an anti-solvent. In one embodiment, the resulted solution is stirred at room temperature for a period of time (e.g., about 18 hours). In one embodiment, the resulted solution is temperature-cycled (e.g., between about 5° C. and about 40° C.) for a period of time (e.g., 4 days). In one embodiment, the solvent is tetrahydrofuran, ethanol, methyl acetate, ethyl acetate, isopropyl acetate, or acetonitrile. In one embodiment, the anti-solvent is heptane, diisopropyl ether, cyclohexane, or water. In one embodiment, the solvent is tetrahydrofuran, and the anti-solvent is heptane. In one embodiment, the solvent is tetrahydrofuran, and the anti-solvent is diisopropyl ether. In one embodiment, the solvent is ethanol, and the anti-solvent is water. In one embodiment, the solvent is methyl acetate, and the anti-solvent is cyclohexane. In one embodiment, the solvent is ethyl acetate, and the anti-solvent is heptane. In one embodiment, the solvent is ethyl acetate, and the anti-solvent is diisopropyl ether. In one embodiment, the solvent is isopropyl acetate, and the anti-solvent is cyclohexane. In one embodiment, the solvent is acetonitrile, and the anti-solvent is water.

In one embodiment, provided herein is a solid form comprising Form H of Compound 1. In one embodiment, the solid form is substantially free of amorphous Compound 1. In one embodiment, the solid form is substantially free of other crystalline forms of Compound 1. In one embodiment, the solid form is substantially free of Form A, Form B, Form C, Form D, Form E, Form F, Form G, or Form I of Compound 1. In one embodiment, the solid form is substantially free of salts of Compound 1. In one embodiment, the solid form consists essentially of Form H of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form H of Compound 1. In one embodiment, the solid form comprising Form H of Compound 1 is substantially pure.

In one embodiment, provided herein is a solid form comprising Form H of Compound 1 and amorphous Compound 1. In one embodiment, provided herein is a solid form comprising Form H of Compound 1 and one or more other crystalline forms of Compound 1. In one embodiment, provided herein is a solid form comprising Form H of Compound 1 and one or more of Form A, Form B, Form C, Form D, Form E, Form F, Form G, and Form I of Compound 1.

Further properties of the Form H are provided in the Examples section.

All of the combinations of the above embodiments are encompassed by this application.

(j) Form I

In certain embodiments, provided herein is Form I of Compound 1.

In one embodiment, Form I is crystalline. In one embodiment, Form I is substantially crystalline. In one embodiment, Form I is moderately crystalline. In one embodiment, Form I is partially crystalline.

A representative XRPD pattern of Form I is provided in FIG. 33.

In one embodiment, provided herein is a solid form comprising Compound 1, characterized by 1, 2, 3, 4, 5, 6, 7, 8, 9, 10, or all of the peaks located at approximately the following positions: 6.8, 8.8, 11.5, 12.7, 15.2, 16.7, 17.8, 19.1, 21.3, 24.7, and 25.7° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by all of the peaks.

In one embodiment, provided herein is a solid form comprising Compound 1, characterized by an XRPD pattern comprising peaks at approximately 6.8, 12.7, and 16.7° 2θ. In one embodiment, the XRPD pattern further comprises peaks at approximately 11.5 and 15.2° 2θ. In one embodiment, the XRPD pattern comprises peaks at approximately 6.8, 11.5, 12.7, 15.2, and 16.7° 2θ, in combination with at least one peak selected from approximately 17.8, 19.1, 21.3, 24.7, and 25.7° 2θ.

In one embodiment, provided herein is a solid form comprising Compound 1, characterized by an XRPD pattern comprising peaks at approximately 6.8, 12.7, and 16.7° 2θ. In one embodiment, the XRPD pattern further comprises peaks at approximately 11.5 and 17.8° 2θ. In one embodiment, the XRPD pattern comprises peaks at approximately 6.8, 11.5, 12.7, 16.7, and 17.8° 2θ, in combination with at least one peak selected from approximately 15.2, 19.1, 21.3, 24.7, and 25.7° 2θ.

In one embodiment, provided herein is a solid form comprising Compound 1, characterized by an XRPD pattern comprising peaks at approximately 15.2, 16.7, and 17.8° 2θ. In one embodiment, the XRPD pattern further comprises peaks at approximately 12.7, 19.1, and 25.7° 2θ. In one embodiment, the XRPD pattern comprises peaks at approximately 12.7, 15.2, 16.7, 17.8, 19.1, 25.7° 2θ, in combination with at least one peak selected from approximately 6.8, 11.5, 21.3, and 24.7° 2θ.

In one embodiment, provided herein is a solid form comprising Compound 1, characterized by an XRPD pattern that matches the XRPD pattern presented in FIG. 33.

In one embodiment, the XRPD patterns are obtained using Cu Kα radiation. In one embodiment, the term "approximately" as used in connection with an XRPD peak location means a variation of ±0.2° 2θ. In one embodiment, the term "approximately" as used in connection with an XRPD peak location means a variation of ±0.1° 2θ. As used herein, when a term "approximately" is used in connection with multiple XRPD peak locations, the term "approximately" applies to all of the XRPD peak locations.

In one embodiment, Form I is prepared by heating a solid form of Compound 1 from about 27° C. to about 115° C. at a heating rate of 5° C./min. In one embodiment, the heating is done inside a DSC-XRPD sample cell. In one embodiment, the solid form of Compound 1 is Form B.

In one embodiment, provided herein is a solid form comprising Form I of Compound 1. In one embodiment, the solid form is substantially free of amorphous Compound 1.

In one embodiment, the solid form is substantially free of other crystalline forms of Compound 1. In one embodiment, the solid form is substantially free of Form A, Form B, Form C, Form D, Form E, Form F, Form G, or Form H of Compound 1. In one embodiment, the solid form is substantially free of salts of Compound 1. In one embodiment, the solid form consists essentially of Form I of Compound 1. In one embodiment, the solid form comprises no less than about 95%, no less than about 96%, no less than about 97%, no less than about 98%, no less than about 98.5%, no less than about 99%, no less than about 99.5%, or no less than about 99.8% of Form I of Compound 1. In one embodiment, the solid form comprising Form I of Compound 1 is substantially pure.

In one embodiment, provided herein is a solid form comprising Form I of Compound 1 and amorphous Compound 1. In one embodiment, provided herein is a solid form comprising Form I of Compound 1 and one or more other crystalline forms of Compound 1. In one embodiment, provided herein is a solid form comprising Form I of Compound 1 and one or more of Form A, Form B, Form C, Form D, Form E, Form F, Form G, and Form H of Compound 1.

Further properties of the Form I are provided in the Examples section.

All of the combinations of the above embodiments are encompassed by this application.

5.4 Methods of Use

The solid forms and the pharmaceutical compositions comprising Compound 1 provided herein can be used in all the methods provided herein. The solid forms and the pharmaceutical compositions comprising Compound 1 provided herein can be used in the treatment of all diseases, disorders or conditions provided herein.

Provided herein are methods for treating a subject suffering from or at risk for having a disease or disorder that is associated with an activated immune system, wherein the method comprises administering to said subject a solid form comprising Compound 1 provided herein or a pharmaceutical composition thereof. In one embodiment, the disease or disorder can be treated and/or prevented with a selective $S1P_1$ receptor agonist.

In one embodiment, the disease or disorder is selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardiosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

Provided herein are methods for treating a subject suffering from or at risk for having a disease or disorder, wherein the method comprises administering to said subject a solid form comprising Compound 1 provided herein or a pharmaceutical composition thereof, and wherein the disease or disorder is selected from the group consisting of rejection of transplanted organs or tissues such as kidney, liver, heart, lung, pancreas, cornea, and skin; graft-versus-host disease, e.g., brought about by stem cell transplantation; autoimmune syndromes including rheumatoid arthritis, multiple sclerosis, myasthenia gravis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; pollen allergies; type I diabetes; post-infectious autoimmune diseases including rheumatic fever and post-infectious glomerulonephritis; solid cancers; and tumor metastasis, e.g., metastasis of carcinoma.

Provided herein are methods for treating a subject suffering from or at risk for having an autoimmune disease or chronic inflammatory disorder, wherein the method comprises administering to said subject a solid form comprising Compound 1 provided herein or a pharmaceutical composition thereof. In certain embodiments, the autoimmune or chronic inflammatory disorder is polymyositis, dermatomyositis, lupus nephritis, rheumatoid arthritis, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease, or multiple sclerosis.

In one embodiment, provided herein is a method of treating multiple sclerosis, wherein the method comprises administering to a patient in need thereof a solid form comprising Compound 1 provided herein or a pharmaceutical composition thereof. In one embodiment, the solid form is selected from the group consisting of Form A, Form B, Form C, Form D, Form E, Form F, Form G, Form H, or Form I. In one embodiment, provided herein is a method for treating multiple sclerosis, comprising administering to a subject Form A provided herein. In one embodiment, provided herein is a method for treating multiple sclerosis, comprising administering to a subject Form B provided herein. In one embodiment, provided herein is a method for treating multiple sclerosis, comprising administering to a subject Form C provided herein. In one embodiment, provided herein is a method for treating multiple sclerosis, comprising administering to a subject Form D provided herein. In one embodiment, provided herein is a method for treating multiple sclerosis, comprising administering to a subject Form E provided herein. In one embodiment, provided herein is a method for treating multiple sclerosis, comprising administering to a subject Form F provided herein. In one embodiment, provided herein is a method for treating multiple sclerosis, comprising administering to a subject Form G provided herein. In one embodiment, provided herein is a method for treating multiple sclerosis, comprising administering to a subject Form H provided herein. In one embodiment, provided herein is a method for treating multiple sclerosis, comprising administering to a subject Form I provided herein. In one embodiment, the multiple sclerosis is relapsing-remitting multiple sclerosis, primary progressive multiple sclerosis, secondary progressive multiple sclerosis, or relapsing secondary progressive multiple sclerosis. In one embodiment, the multiple sclerosis is relapsing multiple sclerosis. In one embodiment, the multiple sclerosis is relapsing-remitting multiple sclerosis.

In one embodiment, provided herein is a method of treating psoriasis, wherein the method comprises administering to a patient in need thereof a solid form comprising Compound 1 provided herein or a pharmaceutical composition thereof. In one embodiment, the solid form is selected from the group consisting of Form A, Form B, Form C, Form D, Form E, Form F, Form G, Form H, or Form I. In one embodiment, provided herein is a method for treating psoriasis, comprising administering to a subject Form A provided herein. In one embodiment, provided herein is a method for treating psoriasis, comprising administering to a subject Form B provided herein. In one embodiment, provided herein is a method for treating psoriasis, comprising administering to a subject Form C provided herein. In one embodiment, provided herein is a method for treating psoriasis, comprising administering to a subject Form D provided herein. In one embodiment, provided herein is a method for treating psoriasis, comprising administering to a subject Form E provided herein. In one embodiment, provided herein is a method for treating psoriasis, comprising administering to a subject Form F provided herein. In one embodiment, provided herein is a method for treating psoriasis, comprising administering to a subject Form G provided herein. In one embodiment, provided herein is a method for treating psoriasis, comprising administering to a subject Form H provided herein. In one embodiment, provided herein is a method for treating psoriasis, comprising administering to a subject Form I provided herein. In one embodiment, the psoriasis is chronic plaque psoriasis. In one embodiment, the psoriasis is moderate to severe chronic plaque psoriasis.

In one embodiment, provided herein is a method of treating polymyositis, wherein the method comprises administering to a patient in need thereof a solid form comprising Compound 1 provided herein or a pharmaceutical composition thereof. In one embodiment, the solid form is selected from the group consisting of Form A, Form B, Form C, Form D, Form E, Form F, Form G, Form H, or Form I. In one embodiment, provided herein is a method for treating polymyositis, comprising administering to a subject Form A provided herein. In one embodiment, provided herein is a method for treating polymyositis, comprising administering to a subject Form B provided herein. In one embodiment, provided herein is a method for treating polymyositis, comprising administering to a subject Form C provided herein. In one embodiment, provided herein is a method for treating polymyositis, comprising administering to a subject Form D provided herein. In one embodiment, provided herein is a method for treating polymyositis, comprising administering to a subject Form E provided herein. In one embodiment, provided herein is a method for treating polymyositis, comprising administering to a subject Form F provided herein. In one embodiment, provided herein is a method for treating polymyositis, comprising administering to a subject Form G provided herein. In one embodiment, provided herein is a method for treating polymyositis, comprising administering to a subject Form H provided herein. In one embodiment, provided herein is a method for treating polymyositis, comprising administering to a subject Form I provided herein.

In one embodiment, provided herein is a method of treating graft versus host disease, wherein the method comprises administering to a patient in need thereof a solid form comprising Compound 1 provided herein or a pharmaceutical composition thereof. In one embodiment, the solid form is selected from the group consisting of Form A, Form B, Form C, Form D, Form E, Form F, Form G, Form H, or Form I. In one embodiment, provided herein is a method for treating graft versus host disease, comprising administering to a subject Form A provided herein. In one embodiment, provided herein is a method for treating graft versus host disease, comprising administering to a subject Form B provided herein. In one embodiment, provided herein is a method for treating graft versus host disease, comprising administering to a subject Form C provided herein. In one embodiment, provided herein is a method for treating graft versus host disease, comprising administering to a subject Form D provided herein. In one embodiment, provided herein is a method for treating graft versus host disease, comprising administering to a subject Form E provided herein. In one embodiment, provided herein is a method for treating graft versus host disease, comprising administering to a subject Form F provided herein. In one embodiment, provided herein is a method for treating graft versus host disease, comprising administering to a subject Form G provided herein. In one embodiment, provided herein is a method for treating graft versus host disease, comprising administering to a subject Form H provided herein. In one embodiment, provided herein is a method for treating graft versus host disease, comprising administering to a subject Form I provided herein. In one embodiment, the graft versus host disease is symptomatic chronic GVHD.

In another embodiment, provided herein are methods for treating a subject suffering from or at risk for having a neurological disorder, wherein the method comprises administering to said subject a solid form comprising Compound 1 provided herein or a pharmaceutical composition thereof. In one embodiment, the neurological disorder is Rett Syndrome. In one embodiment, the solid form is selected from the group consisting of Form A, Form B, Form C, Form D, Form E, Form F, Form G, Form H, or Form I.

In another embodiment, provided herein are methods for treating a subject suffering from or at risk for renal or hepatic impairment, wherein the method comprises administering to said subject a solid form comprising Compound 1 provided herein or a pharmaceutical composition thereof. In one embodiment, the solid form is selected from the group consisting of Form A, Form B, Form C, Form D, Form E, Form F, Form G, Form H, or Form I.

In another embodiment, provided herein are methods for treating a subject suffering from or at risk for a disease or disorder mediated by lymphocyte interactions, wherein the method comprises administering to said subject a solid form comprising Compound 1 provided herein or a pharmaceutical composition thereof. In certain embodiments, the disease or disorder mediated by lymphocyte interactions is, for example, in transplantation, acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus. In one embodiment, the solid form is selected from the group consisting of Form A, Form B, Form C, Form D, Form E, Form F, Form G, Form H, or Form I.

In another embodiment, provided herein are methods for the treatment of a disease or disorder associated with sphingosine 1-phosphate and/or sphingosine 1-phosphate receptor, wherein the method comprises administering to said subject a solid form comprising Compound 1 provided herein or a pharmaceutical composition thereof. In certain embodiments, the disease or disorder associated with sphingosine 1-phosphate is multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, or Graves' disease. In one embodiment, the solid form is selected from the group consisting of Form A, Form B, Form C, Form D, Form E, Form F, Form G, Form H, or Form I.

In another embodiment, provided herein are methods for the treatment of a disease or disorder associated with the interferon alpha receptor 1, wherein the method comprises administering to said subject a solid form comprising Compound 1 or a pharmaceutical composition thereof. In certain embodiments, the disease or disorder associated with the interferon alpha receptor is psoriasis, ulcerative colitis, systemic lupus, multiple sclerosis, or rheumatoid arthritis. In one embodiment, the solid form is selected from the group consisting of Form A, Form B, Form C, Form D, Form E, Form F, Form G, Form H, or Form I.

In certain embodiments, the methods provided herein comprise administering a solid form comprising Compound 1 or a pharmaceutical composition thereof, in combination with one or more additional therapeutic agents. In one embodiment, the additional therapeutic agents can be selected from the group comprising or consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors.

In one embodiment, the additional therapeutic agent is an immunosuppressant agent. In one embodiment, the additional therapeutic agent is selected from the group consisting of cyclosporin, daclizumab, basiliximab, everolimus, tacrolimus (FK506), azathiopirene, leflunomide, and 15-deoxyspergualin.

In one embodiment, the additional therapeutic agent is selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl) ethyl methyl (2E)but-2-ene-1,4-dioate, or a pharmaceutically acceptable salt thereof.

5.5 Pharmaceutical Compositions

Solid forms comprising Compound 1 provided herein are useful for the preparation of pharmaceutical compositions, comprising an effective amount of a solid form comprising Compound 1 and a pharmaceutically acceptable vehicle, carrier, diluent, or excipient, or a mixture thereof. In certain embodiments, the pharmaceutically acceptable carrier is hydroxypropyl methylcellulose. In some embodiments, the pharmaceutical compositions described herein are suitable for oral, parenteral, mucosal, transdermal or topical administration.

5.6 Oral Administration

The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose); waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1% to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The solid forms and the pharmaceutical compositions comprising Compound 1 provided herein can be formulated as an oral dosage form. In certain embodiments the oral dosage form comprises one or more of Form A, Form B, Form C, Form D, Form E, Form F, Form G, Form H, or Form I. In certain embodiments the oral dosage form comprises at least 0.001 mg, at least 0.005 mg, at least 0.01 mg, at least 0.05 mg, at least 0.1 mg, at least 0.5 mg, at least 1 mg, at least 2 mg, at least 5 mg, at least 10 mg, at least 20 mg, at least 30 mg, at least 40 mg, or at least 50 mg of Form A, Form B, Form C, Form D, Form E, Form F, Form G, Form H, or Form I. In certain embodiments the oral dosage form comprises about 1 mg, about 2 mg, about 5 mg, about 10 mg, about 20 mg, about 30 mg, about 40 mg, or about 50 mg of Form A, Form B, Form C, Form D, Form E, Form F, Form G, Form H, or Form I. In one embodiment, the oral dosage form comprises about 20 mg of Form A, Form B, Form C, Form D, Form E, Form F, Form G, Form H, or Form I.

5.7 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

5.8 Dosage

In certain embodiments, a dose of Compound 1 used in the methods provided herein is between about 0.5 mg and about 1000 mg per day. In certain embodiments, the dose is between about 1 mg and about 500 mg per day. In certain embodiments, the dose is between about 5 mg and about 200 mg per day.

In certain embodiments, a maintenance dose for Compound 1 used in the methods provided herein is about 10 mg or about 20 mg orally once daily. In certain embodiments, a maintenance dose for Compound 1 is about 20 mg orally once daily. In certain embodiments, the maintenance dose of Compound 1 is 20 mg once daily. In certain embodiments, the maintenance dose of Compound 1 is 20 mg administered as a monotherapy.

In certain embodiments, the Compound 1 can be administered orally once daily a dose of 10 mg for 7 days followed by 20 mg on day 8.

In certain embodiments, the dosing regimen can comprise administration of: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by: (a) a maintenance dose of 10 mg of Compound 1 administered orally once daily from day 12 onwards; or (b) 10 mg of Compound 1 administered orally once daily for 2, 3 or 4 days (i.e., on days 12 and 13; days 12, 13, and 14; or days 12, 13, 14, and 15), especially for 3 days (i.e., on days 12, 13, and 14), followed by a maintenance dose of 20 mg of Compound 1 to be administered orally once daily (i.e., from the day following the day of the last administration of the 10 mg dose onwards).

In certain embodiments, the dosing regimen can comprise administration of: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by 10 mg of Compound 1 administered orally once daily for 2, 3 or 4 days, especially for 3 days; followed by the maintenance dose of 20 mg of Compound 1 administered orally once daily.

In certain embodiments, 10 mg of Compound 1 can be administered orally once daily on days 12, 13, and 14; followed by a maintenance dose of 20 mg of Compound 1 administered orally once daily from day 15 onwards.

In certain embodiments, the dosing regimen can comprise administration of: 2 mg of Compound 1 on days 1 and 2; 3 mg of Compound 1 on days 3 and 4; 4 mg of Compound 1 on days 5 and 6; 5 mg of Compound 1 on day 7; 6 mg of Compound 1 on day 8; 7 mg of Compound 1 on day 9; 8 mg of Compound 1 on day 10; and 9 mg of Compound 1 on day 11; followed by the maintenance dose of 10 mg of Compound 1 administered orally once daily from day 12 onwards.

For clarity reasons, it is noted that the once daily oral doses referred to herein i) refer to the amount of Compound 1 in their free form. In case that for example a pharmaceutically acceptable salt of Compound 1 is used, the amounts given above will need to be adapted accordingly.

6. EXAMPLES

The following Examples are presented by way of illustration, not limitation.

6.1 Analytical Methods

FT-Raman Spectroscopy. Raman spectra were collected with a Nicolet NXR9650 or NXR 960 spectrometer (Thermo Electron) equipped with 1064 nm Nd:YVO$_4$ excitation laser, InGaAs detector, and a MicroStage. All spectra were acquired at 4 cm$^{-1}$ resolution, 64-500 scans, using Happ-Genzel apodization function and 2-level zero-filling.

Polarized-Light Microscopy (PLM). The photomicrographs were collected using Olympus BX51 polarized-light microscope equipped with Olympus DP70 camera.

Powder X-Ray Diffraction (PXRD). PXRD diffractograms were acquired on PANalytical X'Pert Pro diffractometer using Ni-filtered Cu Kα (45 kV/40 mA) radiation and a step size of 0.02° 2θ and X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers. PXRD diffractograms were analyzed using X'Pert Data Viewer version 1.2.0.25 software or X'Pert HighScore Plus version 3.0.0.

Powder X-Ray Diffraction (PXRD). PXRD patterns were also obtained on a Rigaku SmartLab Guidance diffractometer with Cu-Kα radiation and D/teX Ultra detector. The powder samples were deposited on a zero-background polished silicon sample holder and were spun during measurement. Measurements were performed as follows: 40 kV/44 mA tube power, 0.02° 2θ step size, 5° 2θ/min scan rate, and 3-40° 2θ scan range. Data were processed using Rigaku PDXL2 software.

Differential Scanning calorimetry (DSC). DSC was conducted with a TA Instruments Q2000 differential scanning calorimeter equipped with an autosampler and a refrigerated cooling system under 40 mL/min N₂ purge. DSC thermograms were obtained at 10 or 15° C./min in crimped Al pans, unless otherwise noted.

Thermogravimetric Analysis (TGA). TGA thermograms were obtained with a TA Instruments Q5000 thermogravimetric analyzer under 40 mL/min N₂ purge at 10 or 15° C./min in Al pans, unless otherwise noted.

Thermogravimetric Analysis with IR Off-Gas Detection (TGA-IR). TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N₂ flow and heating rate of 15° C./min in Al pans. IR spectra were collected at 4 cm$^{-1}$ resolution and 32 scans at each time point.

6.2 Crystal Form Screen

Compound 1 can be prepared by methods known in the art. See, e.g., International Patent Application Publication No. WO 2005/054215.

By DSC, the starting material had an onset of melting with desolvation of approximately 68° C. TGA-IR identified ethyl acetate as the solvent evolving during heating. TGA indicated a weight loss of 2.4% from RT to 115° C. with additional weight loss above 115° C. due to further desolvation and/or thermal decomposition. The PXRD is presented in FIG. 34, and the DSC/TGA is presented in FIG. 35.

Modes of Crystallization

The crystal-form screen involved a total of 60 solvents and solvent systems and four modes of crystallization:
1. Temperature-cycled (TC) ripening of Compound 1 slurries between 5-40° C. for 65 hours.
2. Rapidly cooling (RC) clarified saturated solutions of Compound 1 from 40° C. to 4° C. and holding at 4° C. for 6.5 days, except for sample #6 that was held at 4° C. for 2 days.
3. Slow evaporation (EV) of Compound 1 solutions at RT for 11 days. For sample vials with residual liquid remaining but no visible solids, evaporation was discontinued after 11 days.
4. Solvent-Antisolvent with stirring (SS-SAS) at RT for 18 hours. Any sample vial where dried contents were poorly crystalline or amorphous or no solids were present were subjected to TC (40 to 5° C.) for 4 days.

Sample Analysis

All solid outputs from the screen were isolated, dried at ambient conditions with vacuum drying for 4 hours and analyzed by FT-Raman spectroscopy. The samples were then sorted into different forms based on Raman and PXRD spectral matches. Representative samples from each form were further analyzed by additional techniques (DSC, TGA, PLM, etc.) as appropriate and as sample quantity permitted. These data were used to support the form assignment.

Results

The crystal-form screen involved 156 TC, RC, EV, and SS-SAS experiments. As shown in Table 1, a total of 41 crystalline solids and 27 amorphous solids were isolated from TC, RC, and EV experiments. As shown in Table 2, an additional 8 crystalline solids were isolated from the SS-SAS experiments.

A summary of the outcomes of the screening study are shown in Table 1 and Table 2.

TABLE 1

Summary of TC, RC, and EV Results

| No. | Solvent | TC | RC | EV |
|---|---|---|---|---|
| 1 | Water | Form B | No solid | No solid |
| 2 | Methanol | Form C | No solid | Form B |
| 3 | 2-Methoxyethanol: Isopropyl ether (20:80) | Form F | No solid | Amorphous |
| 4 | 1-Propanol | Form D | Amorphous | No solid |
| 5 | Nitromethane | Form E | Amorphous | No solid |
| 6 | Acetonitrile | No solid | Form C | No solid |
| 7 | Dimethylsulfoxide: t-Butyl methyl ether (20:80) | No solid | No solid | No solid |
| 8 | Acetone | No solid | No solid | Amorphous |
| 9 | 2-Butanone | No solid | No solid | Amorphous |
| 10 | Dichloromethane | Form C | Form C | No solid |
| 11 | Methyl acetate: Heptane (20:80) | Form F | No solid | No solid |
| 12 | 4-Methyl-2-pentanone | Form E | Amorphous | No solid |
| 13 | Chloroform | No solid | No solid | Amorphous |
| 14 | Ethyl acetate | Form F | No solid | No solid |
| 15 | Chlorobenzene: Cyclohexane (20:80) | Form F | No solid | No solid |
| 16 | Tetrahydrofuran | No solid | No solid | Amorphous |
| 17 | 1,4-Dioxane | No solid | Amorphous | No solid |
| 18 | Isopropyl ether | Amorphous | No solid | Amorphous |
| 19 | Toluene | Form F | No solid | Amorphous |
| 20 | Cyclohexane | Amorphous | No solid | No solid |
| 21 | Heptane | Amorphous | No solid | No solid |
| 22 | 1-Butanol | Form E | Form G | No solid |
| 23 | 2-Propanol | Form D | No solid | Form D |
| 24 | Trifluoroethanol: Isopropyl ether (20:80) | Amorphous | No solid | Amorphous |
| 25 | Dimethyl carbonate | No solid | Amorphous | No solid |
| 26 | t-Butyl methyl ether | Form A | No solid | Amorphous |
| 27 | Isopropyl acetate | Form A | No solid | Form E |
| 28 | Ethanol | Amorphous | Amorphous | No solid |
| 29 | 1-Methoxy-2-propanol: Isopropyl ether (20:80) | Form F | No solid | Amorphous |
| 30 | Cyclohexanone | No solid | No solid | No solid |
| 31 | N,N-Dimethylformamide: Water (20:80) | Form B | No solid | No solid |
| 32 | 2-Methoxyethyl ether: Heptane (20:80) | Amorphous | No solid | Amorphous |
| 33 | hexane | Form A | No solid | No solid |
| 34 | Acetic Acid | No solid | No solid | No solid |
| 35 | anisole | Form F | Form E | No solid |
| 36 | Cumene | Form F | No solid | No solid |
| 37 | IPA: Cyclohexane (20:80) | Form D | No solid | Amorphous |
| 38 | Methanol: Water (90:10) | Form B | Form B | No solid |
| 39 | Acetonitrile: Water (90:10) | No solid | No solid | Form B |
| 40 | Acetone: Water (90:10) | No solid | No solid | Form B |
| 41 | Tetrahydrofuran: Water (90:10) | No solid | No solid | Amorphous |
| 42 | 1,4-Dioxane: Water (90:10) | No solid | No solid | Amorphous |
| 43 | 2-propanol: Water (90:10) | No solid | Form B | Form B |
| 44 | Acetone: Water (80:20) | Form B | No solid | Form B |
| 45 | Ethanol: Water (20:80) | Form D | Form E | No solid |
| 46 | Ethyl acetate: Cyclohexane (20:80) | Form A | No solid | No solid |
| 47 | Acetonitrile: Isopropyl ethyl ether (20:80) | Form E (1x scale); Form H (2x scale) | Amorphous | No solid |
| 48 | 4-Methyl-2-pentanone: Heptane (20:80) | Form F | No solid | No solid |

TABLE 2

Summary of SS-SAS Results

| # | Solvent | Anti-solvent | SS-SAS |
|---|---|---|---|
| 1 | Tetrahydrofuran | Heptane | Form H |
| 2 | Tetrahydrofuran | Diisopropyl ether | Form H |

TABLE 2-continued

Summary of SS-SAS Results

| # | Solvent | Anti-solvent | SS-SAS |
|---|---------|--------------|--------|
| 3 | 2-Propanol | t-butyl methyl ether | No solid |
| 4 | Ethanol | Water | Form H |
| 5 | Methyl acetate | Cyclohexane | Form H |
| 6 | Methyl acetate | t-butyl methyl ether | No solid |
| 7 | Ethyl acetate | Heptane | Form H |
| 8 | Ethyl acetate | Diisopropyl ether | Form H |
| 9 | Isopropyl acetate | Cyclohexane | Form H |
| 10 | Acetonitrile | t-butyl methyl ether | No solid |
| 11 | Acetonitrile | Water | Form H |
| 12 | Methanol | t-butyl methyl ether | No solid |

6.3 Description of Crystal Forms

Form A

Form A is represented by the TC sample from isopropyl acetate (Batch TC-27). The solid was composed of small irregular-shaped particles. The DSC onset of melt/desolvation of this sample was approximately 83° C. TGA-IR detected the evolution of isopropyl acetate upon heating. The PXRD is presented in FIG. 1, the Raman spectrum is presented in FIG. 2, the DSC/TGA is presented in FIG. 3, and the PLM is presented in FIG. 4.

Form B

Form B is represented by the TC sample from water (Batch TC-01). The solid was composed of small irregular-shaped particles. The DSC exhibited two separated endothermic events. The first event had an onset of approximately 50° C. and the second event (likely due to the melt) had an onset of approximately 93° C. TGA-IR shows loss of water upon heating. The PXRD is presented in FIG. 5A, the Raman spectrum is presented in FIG. 6, the DSC/TGA is presented in FIG. 7A, and the PLM is presented in FIG. 8.

In another experiment, Form B was prepared according to the following procedure: The starting material batch of Compound 1 was mixed with ethanol and water (50/50 v/v). The mixture was stirred at ambient temperature at 500 RPM overnight. The suspension was filtered via 0.22 μm Nylon-membraned centrifuge tube filter at 14000 RPM for 8 min. The solids were dried in vacuum oven at 45° C. overnight. The solids were analyzed by XRPD, DSC, TGA and Raman. The PXRD is presented in FIG. 5B, and the DSC/TGA is presented in FIG. 7B.

An alternative experiment produced another batch according to the following procedure: The starting material batch of Compound 1 was mixed with ethanol and water (50/50 v/v). The mixture was stirred at ambient temperature at 600 RPM overnight. The suspension was filtered via 0.45 μm Nylon-membraned centrifuge tube filter at 5800 RPM for 10 min, then transferred to 0.22 μm Nylon-membraned centrifuge tube filter and filtered at 14000 RPM for 15 min. The solids were dried in vacuum oven at 45° C. for 3 days. The solids were analyzed by XRPD (which is the same as FIG. 5B). This batch was used to generate Form I in DSC-XRD experiment.

A representative Form B sample from an EV experiment from acetone:water (80:20 v/v, Batch EV-44) exhibited two separate endothermic events with onsets of ~65° C. and ~107° C., respectively, by DSC. The DSC thermogram is presented in FIG. 7C.

Form C

Form C is represented by the TC sample from dichloromethane (Batch TC-10). The solid was composed of small irregular-shaped particles and larger agglomerated particles. The DSC exhibited two separated endothermic events. The first event had an onset at ~69° C. and the second event had an onset of ~107° C. TGA-IR detected trace dichloromethane upon heating. The PXRD is presented in FIG. 9, the Raman spectrum is presented in FIG. 10, the DSC/TGA is presented in FIG. 11, and the PLM is presented in FIG. 12.

Form D

Form D is represented by the TC sample from 2-propanol (Batch TC-37). The solid was composed of small irregular-shaped particles and larger agglomerated particles. The DSC onset of this sample was approximately 85° C. TGA-IR detected the evolution of water and cyclohexane upon heating. The PXRD is presented in FIG. 13, the Raman spectrum is presented in FIG. 14, the DSC/TGA is presented in FIG. 15, and the PLM is presented in FIG. 16.

Form E

Form E is represented by the TC sample from 1-butanol (Batch TC-22). The solid was composed of small irregular-shaped particles. The DSC onset of this sample was approximately 83° C. The weight loss up to 110° C. by TGA was less than 0.4% suggesting Form E is likely a non-solvated form. TGA-IR detected evolution of trace 1-butanol upon heating. The PXRD is presented in FIG. 17, the Raman spectrum is presented in FIG. 18, the DSC/TGA is presented in FIG. 19, and the PLM is presented in FIG. 20.

Form F

Form F is represented by the TC sample from toluene (Batch TC-19). The solid was composed of small irregular-shaped particles and larger agglomerated particles. The DSC onset of this sample was approximately 86° C. TGA-IR detected the evolution of toluene upon heating. The PXRD is presented in FIG. 21, the Raman spectrum is presented in FIG. 22, the DSC/TGA is presented in FIG. 23, and the PLM is presented in FIG. 24.

Form G

Form G is represented by the RC sample from 1-butanol (Batch RC-22). The solid was composed of small irregular-shaped particles. The DSC exhibited two separated endothermic events. The first event had an onset of approximately 54° C. and the second event had an onset of approximately 85° C. TGA-IR detection the evolution of 1-butanol upon heating. The PXRD is presented in FIG. 25, the Raman spectrum is presented in FIG. 26, the DSC/TGA is presented in FIG. 27, and the PLM is presented in FIG. 28.

Form H

Form H was not observed in the original set of TC experiments (1× scale). Form H was produced by the TC sample in acetonitrile:isopropyl ethyl ether (20:80 v/v, at 2× scale). Form H was also observed in 8 SS-SAS experiments. The solid was composed of small irregular-shaped particles. The DSC onset of melt of this sample was approximately 128° C. The weight loss up to about 113° C. by TGA was less than 0.1% suggesting Form H is a non-solvated form. The PXRD is presented in FIG. 29, the Raman spectrum is presented in FIG. 30, the DSC/TGA is presented in FIG. 31, and the PLM is presented in FIG. 32.

Form I

Form I was prepared by heating Form B of Compound 1 from about 27° C. to about 115° C. at a heating rate of 5° C./min inside a DSC-XRPD sample cell. The XRPD is presented in FIG. 33.

6.4 Evaluation of Solid Forms (a) Solubility Measurements

A weighed sample of each of Form A, Form B, Form C, Form D, Form E, Form F, Form H, and Form I is treated with aliquots of the test solvent at ambient temperature or elevated temperature. Complete dissolution of the test material is determined by visual inspection. Solubility is estimated based on the total solvent used to provide complete dissolution of the sample. The actual solubility may be greater than the value calculated because of the use of solvent aliquots that were too large or due to a slow rate of dissolution.

(b) Stability Measurements

Stability of each of Form A, Form B, Form C, Form D, Form E, Form F, Form H, and Form I is determined by exposing the sample to a 40° C./75% relative humidity (RH) environment for four weeks or 11% RH at ambient temperature for four days.

6.5 Biological Evaluation (a) S1P1 Assays

The compounds are useful in the treatment of a variety of S1P1 receptor-mediated clinical conditions, including auto-immune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas. Therefore, the compounds of the invention may be assayed for their ability to modulate the S1P1 receptor activity. See Colandrea, *Biorg. Med. Chem. Lett.* 2006, 16(11):2905-2908.

(i) In Vitro Binding Assay

The solid forms described herein (e.g., Form A, Form B, Form C, Form D, Form E, Form F, Form H, and Form I) are evaluated using a [$^{35}$S]-GTPgammaS binding assay to monitor dose-dependent selectivity against S1P1 receptors. The assay is completed with sample solid forms subjected to an eight-point, four-fold dose response curve with starting concentration of 10 µM. Selectivity is determined upon initial addition of solid forms followed by an incubation period. Following compound incubation, bounded [$^{35}$S]-GTPgammaS is determined by filtration and scintillation counting. Percentage activation and inhibition values are determined relative to the reference agonist at S1P1.

(ii) In Vivo Blood Lymphocyte Depletion Assay

In addition to their S1P1 binding properties, modulators of the S1P1 receptor also have accelerating lymphocyte homing properties. These properties may be measured using a blood lymphocyte depletion assay. The solid forms described herein (e.g., Form A, Form B, Form C, Form D, Form E, Form F, Form H, and Form I) are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

(b) In Vitro Metabolic Disposition in Liver Microsomal Fractions

The stability of each of Form A, Form B, Form C, Form D, Form E, Form F, Form H, and Form I is determined according to standard procedures known in the art. For example, stability of each of Form A, Form B, Form C, Form D, Form E, Form F, Form H, and Form I is established by an in vitro assay. An in vitro hepatic microsome stability assay measures the stability of one or more subject compounds when reacting with mouse, rat or human microsomes.

Incubations with liver microsomes are conducted in a final volume of 0.1 mL per incubation time point. 10 µM of the subject compound from a stock solution in DMSO (final DMSO concentration of 0.1%) is incubated at 37° C. from 0-60 min with pooled microsomal protein (1.0 mg/mL), suspended in incubation buffer (0.1 M potassium phosphate, pH 7.4, 5 mM MgCl$_2$, and 0.1 mM EDTA). The microsomal reaction is initiated by the addition of NADPH (3 mM final concentration). Incubations with (a) no protein or (b) no NADPH serve as controls. Reactions are terminated by the addition of 0.2 mL of stop solution (acetonitrile). The samples are vortex-mixed for 30 sec and then centrifuged at 10,000×g for 10 min. The supernatant is dried using a Labconco CentriVap concentrator and the dry residue reconstituted in water, transferred to an HPLC glass vial and analyzed by HPLC-UV. The disappearance of the subject compound is used to evaluate the in vitro metabolism thereof.

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A solid form comprising Compound 1:

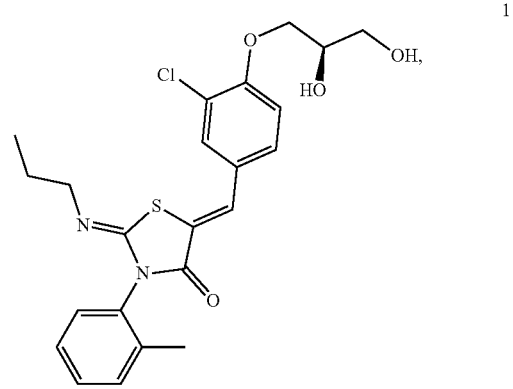 [SMILES: CCC/N=C1\S/C(=C\c2ccc(OC[C@H](O)CO)c(Cl)c2)C(=O)N1c1ccccc1C]

wherein the solid form is selected from the group consisting of:
- Form C characterized by an XRPD pattern comprising peaks at 4.3, 6.7, 8.7, 10.4, 11.2, and 14.9° 2θ±0.2° 2θ as obtained using Cu Kα radiation,
- Form E characterized by an XRPD pattern comprising peaks at 8.5, 12.3, and 16.9° 2θ±0.2° 2θ as obtained using Cu Kα radiation,
- Form G characterized by an XRPD pattern comprising peaks at 4.5, 6.4, and 10.4° 2θ±0.2° 2θ as obtained using Cu Kα radiation, and
- Form I characterized by an XRPD pattern comprising peaks at 6.8, 12.7, and 16.7° 2θ±0.2° 2θ as obtained using Cu Kα radiation.

2. The solid form of claim 1, wherein the solid form is Form C characterized by an XRPD pattern comprising peaks at 4.3, 6.7, 8.7, 10.4, 11.2, and 14.9° 2θ±0.2° 2θ as obtained using Cu Kα radiation.

3. The solid form of claim 2, wherein the solid form is characterized by an XRPD pattern that matches the XRPD pattern presented in FIG. 9.

4. The solid form of claim 1, wherein the solid form is Form E characterized by an XRPD pattern comprising peaks at 8.5, 12.3, and 16.9° 2θ±0.2° 2θ as obtained using Cu Kα radiation.

5. The solid form of claim 4, wherein the XRPD pattern further comprises peaks at 5.2, 10.5, and 22.9° 2θ±0.2° 2θ.

6. The solid form of claim 4, which is characterized by an XRPD pattern that matches the XRPD pattern presented in FIG. 17.

7. The solid form of claim 1, wherein the solid form is Form G characterized by an XRPD pattern comprising peaks at 4.5, 6.4, and 10.4° 2θ±0.2° 2θ as obtained using Cu Kα radiation.

8. The solid form of claim 7, wherein the XRPD pattern further comprises peaks at 7.3 and 22.4° 2θ±0.2° 2θ.

9. The solid form of claim 1, wherein the solid form is Form I characterized by an XRPD pattern comprising peaks at 6.8, 12.7, and 16.7° 2θ±0.2° 2θ as obtained using Cu Kα radiation.

10. The solid form of claim 9, wherein the XRPD pattern further comprises peaks at 11.5 and 15.2° 2θ±0.2° 2θ.

11. The solid form of claim 9, which is characterized by an XRPD pattern that matches the XRPD pattern presented in FIG. 33.

12. A pharmaceutical composition comprising any one of the solid forms of claim 1, and a pharmaceutically acceptable excipient or carrier.

13. A pharmaceutical composition comprising two or more of the solid forms of claim 1, and a pharmaceutically acceptable excipient or carrier.

14. The pharmaceutical composition of claim 12, further comprising an amorphous form of Compound 1:

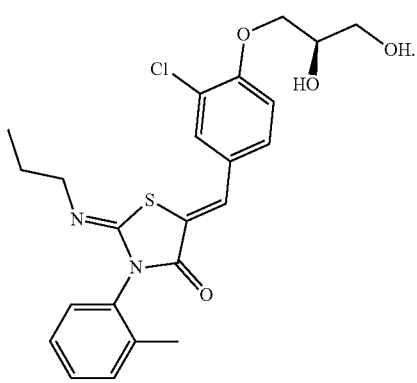 [SMILES: CCC/N=C1\S/C(=C\c2ccc(OC[C@H](O)CO)c(Cl)c2)C(=O)N1c1ccccc1C]

15. The pharmaceutical composition of claim 12, which is a single unit dosage form.

16. The pharmaceutical composition of claim 12, which is a tablet.

17. The pharmaceutical composition of claim 12, which is a capsule.

18. A method of treating multiple sclerosis, comprising administering to a patient in need thereof a therapeutically effective amount of any one of the solid forms of claim 1.

19. A method of treating psoriasis, comprising administering to a patient in need thereof a therapeutically effective amount of any one of the solid forms of claim 1.

20. A method of treating polymyositis, comprising administering to a patient in need thereof a therapeutically effective amount of any one of the solid forms of claim 1.

* * * * *